(12) United States Patent
Meng et al.

(10) Patent No.: US 7,157,604 B2
(45) Date of Patent: Jan. 2, 2007

(54) SELECTIVE ESTROGEN RECEPTOR MODULATORS

(75) Inventors: Dongfang Meng, Westfield, NJ (US); Dann LeRoy Parker, Jr., Edison, NJ (US); Robert R. Wilkening, Maplewood, NJ (US); Ronald W. Ratcliffe, Matawan, NJ (US)

(73) Assignee: Merck & Co., Inc., Rahway, NJ (US)

( * ) Notice: Subject to any disclaimer, the term of this patent is extended or adjusted under 35 U.S.C. 154(b) by 179 days.

(21) Appl. No.: 10/486,005

(22) PCT Filed: Aug. 9, 2002

(86) PCT No.: PCT/US02/25377

§ 371 (c)(1), (2), (4) Date: Feb. 3, 2004

(87) PCT Pub. No.: WO03/015761

PCT Pub. Date: Feb. 27, 2003

(65) Prior Publication Data

US 2004/0210080 A1 Oct. 21, 2004

Related U.S. Application Data

(60) Provisional application No. 60/311,925, filed on Aug. 13, 2001.

(51) Int. Cl.
| | |
|---|---|
| *C07C 211/45* | (2006.01) |
| *C07C 233/15* | (2006.01) |
| *C07C 233/25* | (2006.01) |
| *C07C 233/33* | (2006.01) |
| *C07D 307/46* | (2006.01) |

(52) U.S. Cl. .................... 564/308; 564/222; 549/496; 514/471; 514/630; 514/647

(58) Field of Classification Search .................... None
See application file for complete search history.

(56) References Cited

U.S. PATENT DOCUMENTS 4,731,471 A 3/1988 Cragoe, Jr. et al.

FOREIGN PATENT DOCUMENTS

| WO | WO 01/72713 | 10/2001 |
|---|---|---|
| WO | WO 01/82923 | 11/2001 |
| WO | WO 02/16316 | 2/2002 |
| WO | WO 02/41835 | 5/2002 |

OTHER PUBLICATIONS

Database CASPLUS on STN, Acc. No. 2001:816451, Parker et al., WO 2001082923 (Nov. 8, 2001) (abstract).*

* cited by examiner

*Primary Examiner*—Brian Davis
(74) *Attorney, Agent, or Firm*—Nicole M. Beeler; Mark R. Daniel

(57) ABSTRACT

The present invention relates to compounds and derivatives thereof, their synthesis, and their use as estrogen receptor modulators. The compounds of the instant invention are ligands for estrogen receptors and as such may be useful for treatment or prevention of a variety of conditions related to estrogen functioning including: bone loss, bone fractures, osteoporosis, cartilage degeneration, endometriosis, uterine fibroid disease, hot flashes, increased levels of LDL cholesterol, cardiovascular disease, impairment of cognitive functioning, cerebral degenerative disorders, restenosis, gynecomastia, vascular smooth muscle cell proliferation, obesity, incontinence, and cancer, in particular of the breast, uterus and prostate.

22 Claims, No Drawings

SELECTIVE ESTROGEN RECEPTOR MODULATORS

PRIORITY CLAIM

This application is a §371 National Stage application of PCT/US02/25377, filed on Aug. 09, 2002, which claims priority from the U.S. Provisional Application No. 60/311,925, filed on Aug. 13, 2001, now expired.

BACKGROUND OF THE INVENTION

Naturally occurring and synthetic estrogens have broad therapeutic utility, including: relief of menopausal symptoms, treatment of acne, treatment of dysmenorrhea and dysfunctional uterine bleeding, treatment of osteoporosis, treatment of hirsutism, treatment of prostatic cancer, treatment of hot flashes and prevention of cardiovascular disease. Because estrogen is very therapeutically valuable, there has been great interest in discovering compounds that mimic estrogen-like behavior in estrogen responsive tissues.

For example, estrogen-like compounds would be beneficial in the treatment and prevention of bone loss. Bone loss occurs in a wide range of subjects, including women that are post-menopausal or have had a hysterectomy, patients who were or are currently being treated with corticosteroids, and patient's having gonadal dysgenesis. The current major bone diseases of public concern are osteoporosis, hypercalcemia of malignancy, osteopenia due to bone metastases, periodontal disease, hyperparathyroidism, periarticular erosions in rheumatoid arthritis, Paget's disease, immobilization-induced osteopenia, and glucocorticoid-induced osteoporosis. All of these conditions are characterized by bone loss, resulting from an imbalance between bone resorption, i.e. breakdown, and bone formation, which continues throughout life at the rate of about 14% per year on the average. However, the rate of bone turnover differs from site to site, for example, it is higher in the trabecular bone of the vertebrae and the alveolar bone in the jaws than in the cortices of the long bones. The potential for bone loss is directly related to turnover and can amount to over 5% per year in vertebrae immediately following menopause, a condition which leads to increased fracture risk.

In the U.S., there are currently about 20 million people with detectable fractures of the vertebrae due to osteoporosis. In addition, there are about 250,000 hip fractures per year attributed to osteoporosis. This clinical situation is associated with a 12% mortality rate within the first two years, while 30% of the patients require nursing home care after the fracture.

Osteoporosis affects approximately 20 to 25 million postmenopausal women in the U.S. alone. It has been theorized that the rapid loss of bone mass in these women is due to the cessation of estrogen production of the ovaries. Since studies have shown that estrogen slows the reduction of bone mass due to osteoporosis, estrogen replacement therapy is a recognized treatment for post-menopausal osteoporosis.

In addition to bone mass, estrogen appears to have an effect on the biosynthesis of cholesterol and cardiovascular health. Statistically, the rate of occurrence of cardiovascular disease is roughly equal in postmenopausal women and men; however, premenopausal women have a much lower incidence of cardiovascular disease than men. Because postmenopausal women are estrogen deficient, it is believed that estrogen plays a beneficial role in preventing cardiovascular disease. The mechanism is not well understood, but evidence indicates that estrogen can upregulate the low density lipid (LDL) cholesterol receptors in the liver to remove excess cholesterol.

Postmenopausal women given estrogen replacement therapy experience a return of lipid levels to concentrations comparable to levels associated with the premenopausal state. Thus, estrogen replacement therapy could be an effective treatment for such disease. However, the side effects associated with long term estrogen use limit the use of this alternative.

Also, the estrogen receptor ligands of the present invention can have utility as an anti-depressant, especially when the depression results from an estrogen deficiency.

In models, estrogen has been shown to have beneficial effects on cognitive functioning, such as relieveing anxiety and depression and treating and/or preventing Alzheimer's disease. Estrogen affects the central nervous system by increasing cholinergic functioning, neurotrophin and neurotrophin receptor expression. Estrogen also increases glutamergic synaptic transmission, alters amyloid precursor protein processing and provides neuroprotection. Thus, the estrogen receptor modulators of the present invention could be beneficial for improving cognitive functioning.

The estrogen receptor has been found to have two forms: ERα and ERβ. Ligands bind differently to these two forms, and each form has a different tissue specificity to binding ligands. Thus, it is possible to have compounds that are selective for ERα or ERβ, and therefore confer a degree of tissue specificity to a particular ligand.

Specifically, estrogen receptor beta (ERβ) selective agonists would be useful in the treatment of anxiety and/or depressive illness, as either a single agent or in combination with other agents. Clinical studies have demonstrated the efficacy of the natural estrogen, 17β-estradiol, for the treatment of various forms of depressive illness, see Schmidt P J, Nieman L, Danaceau M A, Tobin M B, Roca C A, Murphy J H, Rubinow D R. Estrogen replacement in perimenopause-related depression: a preliminary report. *Am J Obstet Gynecol* 183:414–20, 2000; and Soares C N, Almeida O P, Joffe H, Cohen L S. Efficacy of estradiol for the treatment of depressive disorders in perimenopausal women: a double-blind, randomized, placebo-controlled trial. *Arch Gen Psychiatry*. 58:537–8, 2001; which are hereby incorporated by reference. Bethea et al (Lu N Z, Shlaes T A, Gundlah C, Dziennis S E, Lyle R E, Bethea C L. Ovarian steroid action on tryptophan hydroxylase protein and serotonin compared to localization of ovarian steroid receptors in midbrain of guinea pigs. *Endocrine* 11:257–67, 1999, which is hereby incorporated by reference) have suggested that the anti-depressant activity of estrogen may be mediated via regulation of serotonin synthesis in the serotonin containing cells concentrated in the dorsal raphe nucleus.

It is believed by some in the field that the physiological responses to estrogen are generally mediated via a series of biochemical events initiated by a selective, high affinity interaction between estrogen and an estrogen receptor. There are two estrogen receptors, ERα and ERβ, and there is co-localization of ERβ (and not ERα) in the serotonin containing cells of the rodent raphe nucleus. Using ERβ selective compounds, estrogen increases transcription of the tryptophan hydroxylase gene (TPH, the key enzyme in serotonin synthesis) via an ERβ mediated event. Potential ERβ selective agonists can be tested in a rodent model of depression by methods familiar to those skilled in the art, for example in a forced swim assay. Likewise, potential ERβ selective agonists can be tested in a rodent model of anxiety by methods familiar to those skilled in the art, for example a guinea pig pup vocalization assay and the resident intruder assay.

Other disease states that affect postmenopausal women include estrogen-dependent breast cancer and uterine cancer. Anti-estrogen compounds, such as tamoxifen, have commonly been used as chemotherapy to treat breast cancer patients. Tamoxifen, a dual antagonist and agonist of estrogen receptors, is beneficial in treating estrogen-dependent breast cancer. However, treatment with tamoxifen is less than ideal because tamoxifen's agonist behavior enhances its unwanted estrogenic side effects. For example, tamoxifen and other compounds that agonize estrogen receptors tend to increase cancer cell production in the uterus. A better therapy for such cancers would be an anti-estrogen compound that has negligible or nonexistent agonist properties.

Although estrogen can be beneficial for treating pathologies such as bone loss, increased lipid levels, and cancer, long-term estrogen therapy has been implicated in a variety of disorders, including an increase in the risk of uterine and endometrial cancers. These and other side effects of estrogen replacement therapy are not acceptable to many women, thus limiting its use.

Alternative regimens, such as a combined progestogen and estrogen dose, have been suggested in an attempt to lessen the risk of cancer. However, such regimens cause the patient to experience withdrawal bleeding, which is unacceptable to many older women. Furthermore, combining estrogen with progestogen reduces the beneficial cholesterol-lowering effect of estrogen therapy. In addition, the long term effects of progestogen treatment are unknown.

In addition to post-menopausal women, men suffering from prostatic cancer can also benefit from anti-estrogen compounds. Prostatic cancer is often endocrine-sensitive; androgen stimulation fosters tumor growth, while androgen suppression retards tumor growth. The administration of estrogen is helpful in the treatment and control of prostatic cancer because estrogen administration lowers the level of gonadotropin and, consequently, androgen levels.

What is needed in the art are compounds that can produce the same positive responses as estrogen replacement therapy without the negative side effects. Also needed are estrogen-like compounds that exert selective effects on different tissues of the body.

The compounds of the instant invention are ligands for estrogen receptors and as such may be useful for treatment or prevention of a variety of conditions related to estrogen functioning including: bone loss, bone fractures, osteoporosis, metastatic bone disease, Paget's disease, periodontal disease, cartilage degeneration, endometriosis, uterine fibroid disease, hot flashes, increased levels of LDL cholesterol, cardiovascular disease, impairment of cognitive functioning, cerebral degenerative disorders, restenosis, gynecomastia, vascular smooth muscle cell proliferation, obesity, incontinence, anxiety, depression resulting from an estrogen deficiency, and cancer, in particular of the breast, uterus and prostate.

SUMMARY OF THE INVENTION

The present invention relates to compounds that are capable of treating and/or preventing a variety of conditions related to estrogen functioning. One embodiment of the present invention is illustrated by a compound of Formula I, and the pharmaceutically acceptable salts and stereoisomers thereof:

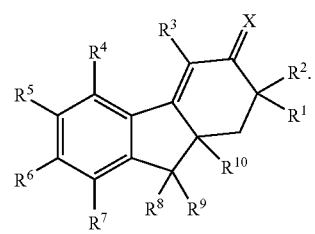

DETAILED DESCRIPTION OF THE INVENTION

The present invention relates to compounds useful as estrogen receptor modulators. Compounds of the present invention are described by the following chemical formula:

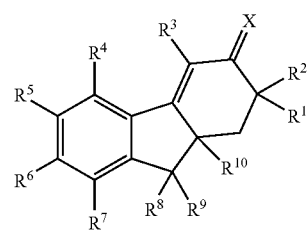

wherein X is selected from the group consisting of: O, N—$OR^a$, N—$NR^aR^b$ and $C_{1-6}$ alkylidene, wherein said alkylidene group is unsubstituted or substituted with a group selected from hydroxy, amino, O($C_{1-4}$alkyl), NH($C_{1-4}$alkyl), or N($C_{1-4}$alkyl)$_2$;

$R^1$ is selected from the group consisting of hydrogen, $C_{1-6}$alkyl, $C_{2-6}$alkenyl, and $C_{2-6}$alkynyl, wherein said alkyl, alkenyl and alkynyl groups are either unsubstituted or substituted with a group selected from $OR^c$, $SR^c$, $NR^bR^c$, C(=O)$R^c$, C(=O)$CH_2OH$, or phenyl, wherein said phenyl group can either be unsubstituted or substituted with 1–3 substituents independently selected from the group consisting of $C_{1-4}$alkyl, OH, O($C_{1-4}$alkyl), $NH_2$, NH($C_{1-4}$alkyl), N($C_{1-4}$alkyl)$_2$, halo, CN, $NO_2$, $CO_2H$, $CO_2$($C_{1-4}$alkyl), C(O)H, and C(O)($C_{1-4}$alkyl);

$R^2$ is selected from the group consisting of hydrogen, hydroxy, iodo, O(C(=O))$R^c$, C(=O)$R^c$, $CO_2R^c$, $C_{1-6}$alkyl, $C_{2-6}$alkenyl, and $C_{2-6}$alkynyl, wherein said alkyl, alkenyl and alkynyl groups are either unsubstituted or substituted with a group selected from $OR^c$, $SR^c$, $NR^bR^c$, C(=O)$R^c$, C(=O)$CH_2OH$, or phenyl, wherein said phenyl group can either be unsubstituted or substituted with 1–3 substituents independently selected from the group consisting of $C_{1-4}$alkyl, OH, O($C_{1-4}$alkyl), $NH_2$, NH($C_{1-4}$alkyl), N($C_{1-4}$alkyl)$_2$, halo, CN, $NO_2$, $CO_2H$, $CO_2$($C_{1-4}$alkyl), C(O)H, and C(O)($C_{1-4}$alkyl);

or $R^1$ and $R^2$, when taken together with the carbon atom to which they are attached, form a carbonyl group;

or $R^1$ and $R^2$, when taken together, form a $C_{1-6}$alkylidene group, wherein said alkylidene group is either unsubstituted or substituted with a group selected from the group consisting of hydroxy, O($C_{1-4}$alkyl), N($C_{1-4}$alkyl)$_2$, and phenyl, wherein said phenyl group can either be unsubstituted or substituted with 1–3 substituents independently selected from the group consisting of $C_{1-4}$alkyl, OH, O($C_{1-4}$alkyl), $NH_2$, NH($C_{1-4}$alkyl), N($C_{1-4}$alkyl)$_2$, halo, CN, $NO_2$, $CO_2H$, $CO_2$($C_{1-4}$alkyl), C(O)H, and C(O)($C_{1-4}$alkyl);

$R^3$ is selected from the group consisting of hydrogen, fluoro, chloro, bromo, iodo, cyano, nitro, $NR^aR^c$, $OR^a$, C(=O)$R^a$, $CO_2R^c$, $CONR^aR^c$, $SR^a$, S(=O)$R^a$, $SO_2R^a$, $C_{1-10}$alkyl, $C_{2-10}$alkenyl, $C_{2-10}$alkynyl, $C_{3-7}$cycloalkyl, $C_{5-7}$cycloalkenyl, 4–7 membered heterocycloalkyl, (cycloalkyl)alkyl, (cycloalkenyl)alkyl, (heterocycloalkyl)alkyl, aryl, heteroaryl, arylalkyl, and (heteroaryl)alkyl, wherein said alkyl, alkenyl, alkynyl, cycloalkyl, cycloalkenyl, heterocycloalkyl, aryl and heteroaryl groups are either unsubstituted or independently substituted with 1, 2 or 3 groups selected from fluoro, chloro, bromo, iodo, cyano, oxo, $OR^a$, $NR^aR^c$, O(C=O)$R^a$, O(C=O)$NR^aR^c$, $NR^a$(C=O)$R^c$, $NR^a$(C=O)$OR^c$, C(=O)$R^a$, $CO_2R^a$, $CONR^aR^c$, $CSNR^aR^c$, $SR^a$, S(O)$R^a$, $SO_2R^a$, $SO_2NR^aR^c$, $YR^d$, and $ZYR^d$;

$R^4$ and $R^5$ are each independently selected from the group consisting of hydrogen, hydroxy, amino, methyl, $CF_3$, fluoro, chloro, and bromo;

$R^6$ is selected from the group consisting of $NH_2$, NH(C=O)$R^e$, and NH(C=O)$OR^e$;

$R^7$ is selected from the group consisting of hydrogen, $OR^b$, $NR^bR^c$, fluoro, chloro, bromo, iodo, cyano, nitro, $C_{1-6}$alkyl, $C_{2-6}$alenyl, $CF_3$, and $CBF_2$;

$R^8$ and $R^9$ are each independently selected from the group consisting of hydrogen, fluoro, chloro, $C_{1-6}$alkyl, $C_{2-6}$alkenyl, and $C_{2-6}$alkynyl, or $R^8$ and $R^9$, when taken together with the carbon atom to which they are attached, form a 3–5 membered cycloalkyl ring, or $R^8$ and $R^9$, when taken together with the carbon atom to which they are attached, form a carbonyl group;

$R^{10}$ is selected from the group consisting of hydrogen, $C_{1-10}$alkyl, $C_{2-10}$alkenyl, $C_{2-10}$alkynyl, $C_{3-6}$cycloalkyl, $C_{4-6}$cycloalkenyl, (cycloalkyl)alkyl, (cycloalkyl)alkenyl, (cycloalkenyl)alkyl, aryl, heteroaryl, arylalkyl and (heteroaryl)alkyl, wherein said alkyl, alkenyl, alkynyl, cycloalkyl, cycloalkenyl, (cycloalkyl)alkyl, (cycloalkyl)alkenyl, (cycloalkenyl)alkyl, aryl, heteroaryl, arylalkyl and (heteroaryl)alkyl groups can be optionally substituted with a group selected from bromo, iodo, $OR^b$, $SR^b$, C(=O)$R^b$, 1–3 $C_{1-3}$alkyl, 1–3 chloro, or 1–5 fluoro, or $R^{10}$ and $R^1$, when taken together with the three intervening carbon atoms to which they are attached, form a 5–6 membered cycloalkyl or cycloalkenyl ring which can be optionally substituted with 1–3 groups independently selected from oxo, hydroxy, fluoro, $C_{1-6}$alkyl, $C_{2-6}$alkenyl, $C_{2-6}$alkynyl, $C_{1-6}$alkylidenyl, $C_{3-6}$cycloalkyl, (cycloalkyl)alkyl, phenyl, or phenylalkyl, wherein said alkyl, alkenyl, alkynyl, alkylidenyl, cycloalkyl, (cycloalkyl)alkyl, phenyl, and phenylalkyl groups can be optionally substituted with a group selected from chloro, bromo, iodo, $OR^b$, $SR^b$, $C_{1-3}$alkyl, C(=O)$R^b$, or 1–5 fluoro;

$R^a$ is selected from the group consisting of hydrogen, $C_{1-10}$alkyl, and phenyl, wherein said alkyl group can be optionally substituted with a group selected from hydroxy, amino, O($C_{1-4}$alkyl), NH($C_{1-4}$alkyl), N($C_{1-4}$alkyl)$_2$, phenyl, or 1–5 fluoro, and wherein said phenyl groups can either be unsubstituted or substituted with 1–3 substituents independently selected from the group consisting of $C_{1-4}$alkyl, OH, O($C_{1-4}$alkyl), $NH_2$, NH($C_{1-4}$alkyl), N($C_{1-4}$alkyl)$_2$, halo, CN, $NO_2$, $CO_2H$, $CO_2$($C_{1-4}$alkyl), C(O)H, and C(O)($C_{1-4}$alkyl);

$R^b$ is selected from the group consisting of hydrogen, $C_{1-10}$alkyl, benzyl and phenyl, wherein said phenyl group can either be unsubstituted or substituted with 1–3 substituents independently selected from the group consisting of $C_{1-4}$alkyl, OH, O($C_{1-4}$alkyl), $NH_2$, NH($C_{1-4}$alkyl), N($C_{1-4}$alkyl)$_2$, halo, CN, $NO_2$, $CO_2H$, $CO_2$($C_{1-4}$alkyl), C(O)H, and C(O)($C_{1-4}$alkyl);

$R^c$ is selected from the group consisting of hydrogen, $C_{1-10}$alkyl and phenyl, wherein said phenyl group can either be unsubstituted or substituted with 1–3 substituents independently selected from the group consisting of $C_{1-4}$alkyl, OH, O($C_{1-4}$alkyl), $NH_2$, NH($C_{1-4}$alkyl), N($C_{1-4}$alkyl)$_2$, halo, CN, $NO_2$, $CO_2H$, $CO_2$($C_{1-4}$alkyl), C(O)H, and C(O)($C_{1-4}$alkyl);

or $R^a$ and $R^c$, whether or not on the same atom, can be taken together with any attached and intervening atoms to form a 4–7 membered ring;

$R^d$ is selected from the group consisting of $NR^bR^c$, $OR^a$, $CO_2R^a$, O(C=O)$R^a$, CN, $NR^c$(C=O)$R^b$, $CONR^aR^c$, $SO_2NR^aR^c$, and a 4–9 membered mono- or bi-cyclic N-heterocycloalkyl ring that can be optonally substituted with 1–3 $C_{1-3}$alkyl and can be optionally interrupted by O, S, $NR^c$, or C=O;

$R^e$ is selected from the group consisting of hydrogen, $C_{1-6}$alkyl, $C_{2-6}$alkenyl, phenyl, and phenylalkyl, wherein said alkyl, alkenyl, or phenyl group can either be unsubstituted or substituted with 1–3 substituents independently selected from the group consisting of $C_{1-3}$alkyl, OH, O($C_{1-4}$alkyl), $NH_2$, NH($C_{1-4}$alkyl), N($C_{1-4}$alkyl)$_2$, halo, CN, $NO_2$, $CO_2H$, $CO_2$($C_{1-4}$alkyl), C(O)H, and C(O)($C_{1-4}$alkyl);

Y is selected from the group consisting of $CR^bR^c$, $C_{2-6}$alkylene and $C_{2-6}$alkenylene, wherein said alkylene and alkenylene linkers can be optionally interrupted by O, S, or $NR^c$;

Z is selected from the group consisting of O, S, $NR^c$, C=O, O(C=O), (C=O)O, $NR^c$(C=O) or (C=O)$NR^c$;

and the pharmaceutically acceptable salts thereof.

In the compounds of the present invention, X is preferably selected from the group consisting of O and N—$OR^a$. More preferably, X is selected from the group consisting of O, N—OH and N—$OCH_3$.

In the compounds of the present invention, $R^1$ is preferably selected from the group consisting of hydrogen and $C_{1-6}$alkyl, wherein said alkyl group is either unsubstituted or substituted with a group selected from $OR^c$ or C(=O)$R^c$.

In the compounds of the present invention, $R^2$ is preferably selected from the group consisting of hydrogen, hydroxy, iodo, and $C_{1-6}$alkyl, wherein said alkyl group is either unsubstituted or substituted with a group selected from $OR^c$ or C(=O)$R^c$.

In the compounds of the present invention, $R^3$ is preferably selected from the group consisting of chloro, bromo, iodo, cyano, nitro, C(=O)$R^a$, $C_{1-10}$alkyl, $C_{2-10}$alkenyl, aryl and heteroaryl, wherein said alkyl, alkenyl, aryl and heteroaryl groups are either unsubstituted or independently substituted with 1, 2 or 3 groups selected from fluoro, chloro, bromo, iodo, cyano, $OR^a$, $NR^aR^c$, C(=O)$R^a$, $CO_2R^c$, $NR^a$C(=O)$R^c$, $CONR^aR^c$, $CSNR^aR^c$, $SR^a$, $YR^d$, and $ZYR^d$.

In the compounds of the present invention, $R^3$ is more preferably selected from the group consisting of chloro, bromo, iodo, cyano, nitro, C(=O)$R^a$, $C_{1-10}$alkyl, aryl and heteroaryl, wherein said alkyl, aryl and heteroaryl groups are either unsubstituted or independently substituted with 1, 2 or 3 groups selected from fluoro, $NR^aR^c$, $OR^a$, $YR^d$, and $ZYR^d$.

In the compounds of the present invention, $R^4$ and $R^5$ are each independently preferably selected from the group consisting of hydrogen, fluoro, and hydroxy;

In the compounds of the present invention, $R^4$ is more preferably selected from the group consisting of hydrogen and fluoro.

In the compounds of the present invention, $R^5$ is more preferably selected from the group consisting of hydrogen and fluoro.

In the compounds of the present invention, $R^6$ is preferably selected from the group consisting of $NH_2$ and $NH(C=O)R^e$.

In the compounds of the present invention, $R^6$ is more preferably selected from the group consisting of $NH_2$ and $NH(C=O)CH_3$.

In the compounds of the present invention, $R^7$ is preferably selected from the group consisting of hydrogen, $NR^bR^c$, fluoro, chloro, bromo, iodo, cyano, nitro, $C_{1-6}$alkyl, and $CF_3$.

In the compounds of the present invention, $R^7$ is more preferably selected from the group consisting of hydrogen, $NH_2$, fluoro, chloro, bromo, cyano, nitro, and $CH_3$.

In the compounds of the present invention, $R^8$ and $R^9$ are each independently preferably selected from the group consisting of hydrogen and $C_{1-6}$alkyl, or $R^8$ and $R^9$, when taken together with the carbon atom to which they are attached, form a carbonyl group.

In the compounds of the present invention, $R^{10}$ is preferably selected from the group consisting of $C_{1-10}$alkyl, $C_{2-10}$alkenyl, $C_{3-6}$cycloalkyl, (cycloalkyl)alkyl, and phenyl, wherein said alkyl, alkenyl, cycloalkyl, (cycloalkyl)alkyl, and phenyl groups can be optionally substituted with a group selected from bromo, $SR^b$, $C(=O)R^b$, 1–3 chloro, or 1–5 fluoro, or $R^{10}$ and $R^1$, when taken together with the three intervening carbon atoms to which they are attached, form a 5–6 membered cycloalkyl ring which can be optionally substituted with $C_{1-6}$alkyl, wherein said alkyl group can be optionally substituted with 1–5 fluoro.

Nonlimiting examples of the present invention include, but are not limited to:

7,8-diamino-9a-butyl-6-fluoro-4-methyl-1,2,9,9a-tetrahydro-3H-fluoren-3-one;
7-amino-9a-butyl-6-fluoro-4-nitro-1,2,9,9a-tetrahydro-3H-fluoren-3-one;
4-acetyl-7-amino-8-bromo-9a-butyl-6-fluoro-1,2,9,9a-tetrahydro-3H-fluoren-3-one;
7-amino-4,6-dibromo-9a-butyl-1,2,9,9a-tetrahydro-3H-fluoren-3-one;
7-amino-4,8-dibromo-9a-butyl-1,2,9,9a-tetrahydro-3H-fluoren-3-one;
7-amino-4-bromo-9a-butyl-8-chloro-6-fluoro-1,2,9,9a-tetrahydro-3H-fluoren-3-one;
7-amino-9a-butyl-4,8-dichloro-6-fluoro-1,2,9,9a-tetrahydro-3H-fluoren-3-one;
7-amino-9a-butyl-8-chloro-6-fluoroiodo-1,2,9,9a-tetrahydro-3H-fluoren-3-one;
7-amino-9a-butyl-8-chloro-6-fluoro-4-(2-furyl)-1,2,9,9a-tetrahydro-3H-fluoren-3-one;
7-amino-4,8-dibromo-9a-butyl-6-fluoro-1,2,9,9a-tetrahydro-3H-fluoren-3-one;
7-amino-9a-butyl-6-fluoro-4-methyl-1,2,9,9a-tetrahydro-3H-fluoren-3-one;
7-amino-8-bromo-9a-butyl-6-fluoro-4-methyl-1,2,9,9a-tetrahydro-3H-fluoren-3-one;
7-amino-9a-butyl-6-fluoro-4-methyl-8-nitro-1,2,9,9a-tetrahydro-3H-fluoren-3-one;
7-amino-4-bromo-9a-butyl-6-fluoro-1,2,9,9a-tetrahydro-3H-fluoren-3-one;
7-amino-4-bromo-9a-butyl-6,8-difluoro-1,2,9,9a-tetrahydro-3H-fluoren-3-one;
7-amino-9a-butyl-6,8-difluoro-4-(trifluoromethyl)-1,2,9,9a-tetrahydro-3H-fluoren-3-one;
7-amino-9a-butyl-4-ethyl-6,8-difluoro-1,2,9,9a-tetrahydro-3H-fluoren-3-one;
7-amino-4-bromo-9a-butyl-6-fluoro-8-methyl-1,2,9,9a-tetrahydro-3H-fluoren-3-one;
7-amino-4-bromo-9a-butyl-1,2,9,9a-tetrahydro-3H-fluoren-3-one;
7-amino-4-bromo-8-methyl-9a-propyl-1,2,9,9a-tetrahydro-3H-fluoren-3-one;
7-amino-4-bromo-9a-butyl-8-methyl-1,2,9,9a-tetrahydro-3H-fluoren-3-one;
7-amino-9a-butyl-8-methyl-4-trifluoromethyl-1,2,9,9a-tetrahydro-3H-fluoren-3-one;
7-amino-8-bromo-9a-ethyl-4-methyl-1,2,9,9a-tetrahydro-3H-fluoren-3-one;
7-amino-8-cyano-9a-ethyl-4-methyl-1,2,9,9a-tetrahydro-3H-fluoren-3-one;
7-amino-4,8-dibromo-9a-ethyl-1,2,9,9a-tetrahydro-3H-fluoren-3-one;
7-amino-4,9a-diethyl-6-fluoro-1,2,9,9a-tetrahydro-3H-fluoren-3-one;
7-amino-4-bromo-9a-ethyl-6-fluoro-1,2,9,9a-tetrahydro-3H-fluoren-3-one;
7-amino-9a-butyl-4-ethyl-6-fluoro-1,2,9,9a-tetrahydro-3H-fluoren-3-one;
7-amino-4,9a-diethyl-6-fluoro-8-methyl-1,2,9,9a-tetrahydro-3H-fluoren-3-one;
7-amino-4-chloro-9a-ethyl-6-fluoro-8-methyl-1,2,9,9a-tetrahydro-3H-fluoren-3-one;
7-amino-4-bromo-9a-ethyl-6-fluoro-8-methyl-1,2,9,9a-tetrahydro-3H-fluoren-3-one;
7-amino-9a-butyl-6-fluoro-4,8-dimethyl-1,2,9,9a-tetrahydro-3H-fluoren-3-one;
7-amino-9a-butyl-4-ethyl-6-fluoro-8-methyl-1,2,9,9a-tetrahydro-3H-fluoren-3-one;
7-amino-9a-butylchloro-6-fluoro-8-methyl-1,2,9,9a-tetrahydro-3H-fluoren-3-one;
7-amino-9a-butyl-4-cyano-6-fluoro-8-methyl-1,2,9,9a-tetrahydro-3H-fluoren-3-one;
7-amino-9a-butyl-8-methyl-6-fluoro-4-trifluoromethyl-1,2,9,9a-tetrahydro-3H-fluoren-3-one;
7-amino-9a-ethyl-6,8-difluoromethyl-1,2,9,9a-tetrahydro-3H-fluoren-3-one;
7-amino-4,9a-diethyl-6,8-difluoro-1,2,9,9a-tetrahydro-3H-fluoren-3-one;
7-amino-4-bromo-9a-ethyl-6,8-difluoro-1,2,9,9a-tetrahydro-3H-fluoren-3-one;
7-amino-9a-ethyl-6,8-difluoro-4-trifluoromethyl-1,2,9,9a-tetrahydro-3H-fluoren-3-one;
7-amino-9a-butyl-6,8-difluoro-4-methyl-1,2,9;9a-tetrahydro-3H-fluoren-3-one;
7-amino-8-chloro-9a-ethyl-6-fluoro-4-methyl-1,2,9,9a-tetrahydro-3H-fluoren-3-one;
7-amino-8-chloro-4,9a-diethyl-6-fluoro-1,2,9,9a-tetrahydro-3H-fluoren-3-one;
7-amino-4,8-dichloro-9a-ethyl-6-fluoro-1,2,9,9a-tetrahydro-3H-fluoren-3-one;
7-amino-4-bromo-8-chloro-9a-ethyl-6-fluoro-1,2,9,9a-tetrahydro-3H-fluoren-3-one;

7-amino-8-chloro-9a-ethyl-6-fluoro-4-iodo-1,2,9,9a-tetrahydro-3H-fluoren-3-one;
7-amino-8-chloro-9a-ethyl-6-fluoro-4-(2-furyl)-1,2,9,9a-tetrahydro-3H-fluoren-3-one;
7-amino-8-chloro-6-fluoro-4-methyl-9a-propyl-1,2,9,9a-tetrahydro-3H-fluoren-3-one;
7-amino-8-chloro-4-ethyl-6-fluoro-9a-propyl-1,2,9,9a-tetrahydro-3H-fluoren-3-one;
7-amino-4,8-dichloro-6-fluoro-9a-propyl-1,2,9,9a-tetrahydro-3H-fluoren-3-one;
7-amino-4-bromo-8-chloro-6-fluoro-9a-propyl-1,2,9,9a-tetrahydro-3H-fluoren-3-one;
7-amino-8-chloro-6-fluoro-4-iodo-9a-propyl-1,2,9,9a-tetrahydro-3H-fluoren-3-one;
7-amino-8-chloro-6-fluoro-4-(2-furyl)-9a-propyl-1,2,9,9a-tetrahydro-3H-fluoren-3-one;
7-amino-9a-butyl-8-chloro-6-fluoro-4-methyl-1,2,9,9a-tetrahydro-3H-fluoren-3-one;
7-amino-9a-butyl-8-chloro-4-ethyl-6-fluoro-1,2,9,9a-tetrahydro-3H-fluoren-3-one;
4-acetyl-7-amino-9a-butyl-8-chloro-6-fluoro-1,2,9,9a-tetrahydro-3H-fluoren-3-one;
7-amino-8-bromo-9a-ethyl-6-fluoro-4-methyl-1,2,9,9a-tetrahydro-3H-fluoren-3-one;
7-amino-8-bromo-4,9a-diethyl-6-fluoro-1,2,9,9a-tetrahydro-3H-fluoren-3-one;
7-amino-4,8-dibromo-9a-ethyl-6-fluoro-1,2,9,9a-tetrahydro-3H-fluoren-3-one;
7-amino-8-bromo-9a-butyl-4-ethyl-6-fluoro-1,2,9,9a-tetrahydro-3H-fluoren-3-one;
7-amino-9a-ethyl-6-fluoro-4-methyl-8-nitro-1,2,9,9a-tetrahydro-3H-fluoren-3-one;
7-amino-4,9a-diethyl-6-fluoro-8-nitro-1,2,9,9a-tetrahydro-3H-fluoren-3-one;
7-amino-9a-butyl-4-ethyl-6-fluoro-8-nitro-1,2,9,9a-tetrahydro-3H-fluoren-3-one;
7,8-diamino-9a-butyl-4-ethyl-6-fluoro-1,2,9,9a-tetrahydro-3H-fluoren-3-one;

and the pharmaceutically acceptable salts thereof.

Also included within the scope of the present invention is a pharmaceutical composition which is comprised of a compound of Formula I as described above and a pharmaceutically acceptable carrier. The invention is also contemplated to encompass a pharmaceutical composition which is comprised of a pharmaceutically acceptable carrier and any of the compounds specifically disclosed in the present application. The present invention also relates to methods for making the pharmaceutical compositions of the present invention. The present invention is also related to processes and intermediates useful for making the compounds and pharmaceutical compositions of the present invention. These and other aspects of the invention will be apparent from the teachings contained herein.

Utilities

The compounds of the present invention are selective modulators of estrogen receptors and are therefore useful to treat or prevent a variety of diseases and conditions related to estrogen receptor functioning in mammals, preferably humans.

A variety of diseases and conditions related to estrogen receptor functioning includes, but is not limited to, bone loss, bone fractures, osteoporosis, metastatic bone disease, Paget's disease, periodontal disease, cartilage degeneration, endometriosis, uterine fibroid disease, hot flashes, increased levels of IDL cholesterol, cardiovascular disease, impairment of cognitive functioning, cerebral degenerative disorders, restenosis, gynecomastia, vascular smooth muscle cell proliferation, obesity, incontinence, anxiety, depression resulting from an estrogen deficiency, and cancer, in particular of the breast, uterus and prostate. In treating such conditions with the instantly claimed compounds, the required therapeutic amount will vary according to the specific disease and is readily ascertainable by those skilled in the art. Although both treatment and prevention are contemplated by the scope of the invention, the treatment of these conditions is the preferred use.

The present invention also relates to methods for eliciting an estrogen receptor modulating effect in a mammal in need thereof by administering the compounds and pharmaceutical compositions of the present invention.

The present invention also relates to methods for eliciting an estrogen receptor antagonizing effect in a mammal in need thereof by administering the compounds and pharmaceutical compositions of the present invention. The estrogen receptor antagonizing effect can be either an ERα antagonizing effect, an ERβ antagonizing effect or a mixed ERα and ERβ antagonizing effect.

The present invention also relates to methods for eliciting an estrogen receptor agonizing effect in a mammal in need thereof by administering the compounds and pharmaceutical compositions of the present invention. The estrogen receptor agonizing effect can be either an Eα agonizing effect, an ERβ agonizing effect or a mixed ERα and ERβ agonizing effect. A preferred method of the present invention is eliciting an ERβ agonizing effect.

The present invention also relates to methods for treating or preventing disorders related to estrogen functioning, bone loss, bone fractures, osteoporosis, metastatic bone disease, Paget's disease, periodontal disease, cartilage degeneration, endometriosis, uterine fibroid disease, hot flashes, increased levels of LDL cholesterol, cardiovascular disease, impairment of cognitive functioning, cerebral degenerative disorders, restenosis, gynecomastia, vascular smooth muscle cell proliferation, obesity, incontinence, anxiety, depression resulting from an estrogen deficiency, and cancer, in particular of the breast, uterus and prostate in a mammal in need thereof by administering the compounds and pharmaceutical compositions of the present invention. Exemplifying the invention is a method of treating or preventing depression. Exemplifying the invention is a method of treating or preventing anxiety. Exemplifying the invention is a method of treating or preventing hot flashes. Exemplifying the invention is a method of treating or preventing cancer. Exemplifying the invention is a method of treating or preventing cardiovascular disease.

An embodiment of the invention is a method for treating or preventing cancer, especially of the breast, uterus or prostate, in a mammal in need thereof by administering the compounds and pharmaceutical compositions of the present invention. The utility of SERMs for the treatment of breast, uterine or prostate cancer is known in the literature, see T. J. Powles, "Breast cancer prevention," Oncologist 2002; 7(1): 60–4; Park, W. C. and Jordan, V. C., "Selective estrogen receptor modulators (SERMS) and their roles in breast cancer prevention." Trends Mol Med. 2002 Febuary; 8(2): 82–8; Wolff, A. C. et al, "Use of SERMs for the adjuvant therapy of early-stage breast cancer," Ann N Y Acad Sci. 2001 December; 949:80–8; Steiner, M. S. et al., "Selective estrogen receptor modulators for the chemoprevention of prostate cancer," Urology 2001 April; 57(4 Suppl 1):68–72.

Another embodiment of the invention is a method of treating or preventing metastatic bone disease in a mammal in need thereof by administering to the mammal a therapeutically effective amount of any of the compounds or pharmaceutical compositions described above. The utility of SERMS in the treatment of metastatic bone disease is known in the literature, see, Campisi, C. et al., "Complete resoultion of breast cancer bone metastasis through the use of beta-interferon and tamoxifen," Eur J Gynaecol Oncol 1993;14 (6):479–83.

Another embodiment of the invention is a method of treating or preventing gynecomastia in a mammal in need thereof by administering to the mammal a therapeutically effective amount of any of the compounds or pharmaceutical compositions described above. The utility of SERMS in the treatment of gynecomastia is known in the literature, see, Ribeiro, G. and Swindell R., "Adjuvant tamoxifen for male breast cancer." Br J Cancer 1992; 65:252–254; Donegan, W., "Cancer of the Male Breast," JGSM Vol. 3, Issue 4, 2000.

Another embodiment of the invention is a method of treating or preventing post-menopausal osteoporosis, glucocorticoid osteoporosis, hypercalcemia of malignancy, bone loss and bone fractures in a mammal in need thereof by administering to the mammal a therapeutically effective amount of any of the compounds or pharmaceutical compositions described above. The utility of SERMs to treat or prevent osteoporosis, hypercalcemia of malignancy, bone loss or bone fractures is known in the literature, see Jordan, V. C. et al., "Selective estrogen receptor modulation and reduction in risk of breast cancer, osteoporosis and coronary heart disease," Natl Cancer Inst October 2001;93(19):1449–57; Bjarnason, N H et al., "Six and twelve month changes in bone turnover are realted to reduction in vertebral fracture risk during 3 years of raloxifene treatment in postemenopausal osteoporosis," Osteoporosis Int 2001; 12(11):922–3; Fentiman I. S., "Tamoxifen protects against steroid-induced bone loss," Eur J Cancer 28:684–685 (1992); Rodan, G. A. et al., "Therapeutic Approaches to Bone Diseases," Science Vol 289, 1 Sep. 2000.

Another embodiment of the invention is a method of treating of preventing periodontal disease or tooth loss in a mammal in need thereof by administering to the mammal a therapeutically effective amount of any of the compounds or pharmaceutical compositions described above. The use of SERMs to treat periodontal disease or tooth loss in a mammal is known in the literature, see Rodan, G. A. et al., "Therapeutic Approaches to Bone Diseases," Science Vol 289, 1 Sep. 2000 pp. 1508–14.

Another embodiment of the invention is a method of treating of preventing Paget's disease in a mammal in need thereof by administering to the mammal a therapeutically effective amount of any of the compounds or pharmaceutical compositions described above. The use of SERMs to treat Paget's disease in a mammal is known in the literature, see Rodan, G. A. et al., "Therapeutic Approaches to Bone Diseases," Science Vol 289, 1 Sep. 2000 pp. 1508–14.

Another embodiment of the invention is a method of treating or preventing uterine fibroid disease in a mammal in need thereof by administering to the mammal a therapeutically effective amount of any of the compounds or pharmaceutical compositions described above. The use of SERMS to treat uterine fibroids, or uterine leiomyomas, is known in the literature, see Palomba, S., et al, "Effects of raloxifene treatment on uterine leiomyomas in postmenopausal women," Fertil Steril. 2001 July; 76(1):38–43.

Another embodiment of the invention is a method of treating or preventing obesity in a mammal in need thereof by administering to the mammal a therapeutically effective amount of any of the compounds or pharmaceutical compositions described above. The use of SERMs to treat obesity is known in the literature, see Picard, F. et al., "Effects of the estrogen antagonist EM-652. HCl on energy balance and lipid metabolism in ovariectomized rats," Int J Obes Relat Metab Disord. 2000 July; 24(7):830–40.

Another embodiment of the invention is a method of treating or preventing cartilage degeneration, rheumatoid arthritis or osteoarthritis in a mammal in need thereof by administering to the mammal a therapeutically effective amount of any of the compounds or pharmaceutical compositions described above. The use of SERMs to treat cartilage degeneration, rheumatoid arthritis or osteoarhritis is known in the literature, see Badger, A. M. et al., "Idoxifene, a novel selective estrogen receptor modulator, is effective in a rat model of adjuvant-induced arthritis." J Pharmacol Exp Ther. 1999 December; 291(3):1380–6.

Another embodiment of the invention is a method of treating or preventing endometriosis in a mammal in need thereof by administering to the mammal a therapeutically effective amount of any of the compounds or pharmaceutical compositions described above. The use of SERMs to treat endometriosis is known in the art, see Steven R. Goldstein, "The Effect of SERMs on the Endometrium," Annals of the New York Academy of Sciences 949:237–242 (2001).

Another embodiment of the invention is a method of treating or preventing urinary incontinence in a mammal in need thereof by administering to the mammal a therapeutically effective amount of any of the compounds or pharmaceutical compositions described above. The use of SERMs to treat urinary incontinence is known in the art, see, Goldstein, S. R., "Raloxifene effect on frequency of surgery for pelvic floor relaxation," Obstet Gynecol. 2001 July; 98(1):91–6.

Another embodiment of the invention is a method of treating or preventing cardiovascular disease, restenosis, lowering levels of LDL cholesterol and inhibiting vascular smooth muscle cell proliferation in a mammal in need thereof by administering to the mammal a therapeutically effective amount of any of the compounds or pharmaceutical compositions described above. The utility of SERMs in treating or preventing cardiovascular disease, restenosis, lowering levels of LDL cholesterol and inhibiting vascular smooth muscle cell proliferation is known in the art, see Nuttall, M E et al, "Idoxifene: a novel selective estrogen receptor modulator prevents bone loss and lowers cholesterol levels in ovariectomized rats and decreases uterine weight in intact rats," Endocrinology December 1998;139 (12):5224–34; Jordan, V. C. et al., "Selective estrogen receptor modulation and reduction in risk of breast cancer, osteoporosis and coronary heart disease," Natl Cancer Inst October 2001; 93(19):1449–57; Guzzo J A., "Selective estrogen receptor modulators—a new age of estrogens in cardiovascular disease?," Clin Cardiol 2000 January; 23(1): 15–7; Simoncini T, Genazzani A R., "Direct vascular effects of estrogens and selective estrogen receptor modulators," Curr Opin Obstet Gynecol 2000 June; 12(3):181–7.

Another embodiment of the invention is a method of treating or preventing the impairment of cognitive functioning or cerebral degenerative disorders in a mammal in need thereof by administering to the mammal a therapeutically effective amount of any of the compounds or pharmaceutical compositions described above. The utility of SERMs to prevent the impairment of cognitive functioning is known in the art, see Yaffe, K., K. Krueger, S. Sarkar, et al. 2001. Cognitive function in postmenopausal women treated with raloxifene. N. Eng. J. Med. 344:1207–1213.

Another embodiment of the invention is a method of treating or preventing depression in a mammal in need thereof by administering to the mammal a therapeutically effective amount of any of the compounds or pharmaceutical compositions described above. The utility of estrogens to prevent depression has been described in the art, see Carranza-Liram S., Valentino-Figueroa M L, "Estrogen therapy for depression in postmenopausal women." Int J Gynnaecol Obstet 1999 April; 65(1):35–8.

Another embodiment of the invention is a method of treating or preventing anxiety in a mammal in need thereof by administering to the mammal a therapeutically effective amount of any of the compounds or pharmaceutical compositions described above. The contribution of estrogen receptors in the modulation of emotional processes, such as anxiety has been described in the art, see Krezel, W., et al., "Increased anxiety and synaptic plasticity in estrogen receptor beta-deficient mice." Proc Natl Acad Sci USA 2001 Oct. 9; 98 (21): 12278–82.

Exemplifying the invention is the use of any of the compounds described above in the preparation of a medicament for the treatment and/or prevention of osteoporosis in a mammal in need thereof. Still further exemplifying the invention is the use of any of the compounds described above in the preparation of a medicament for the treatment and/or prevention of:bone loss, bone resorption, bone fractures, metastatic bone disease and/or disorders related to estrogen functioning.

The compounds of this invention may be administered to mammals, preferably humans, either alone or, preferably, in combination with pharmaceutically acceptable carriers or diluents, optionally with known adjuvants, such as alum, in a pharmaceutical composition, according to standard pharmaceutical practice. The compounds can be administered orally or parenterally, including the intravenous, intramuscular, intraperitoneal, subcutaneous, rectal and topical routes of administration.

In the case of tablets for oral use, carriers which are commonly used include lactose and corn starch, and lubricating agents, such as magnesium stearate, are commonly added. For oral administration in capsule form, useful diluents include lactose and dried corn starch. For oral use of a therapeutic compound according to this invention, the selected compound may be administered, for example, in the form of tablets or capsules, or as an aqueous solution or suspension. For oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamide-phenol, polyhydroxy-ethylaspartamide-phenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polyactic and polyglycolic acid, polyepsilon caprolactone, polyhydroxy butyric acid, polyorthoesters, polyacetals, polydihydropyrans, polycyanoacrylates and crosslinked or amphipathic block copolymers of hydrogels.

The instant compounds are also useful in combination with known agents useful for treating or preventing bone loss, bone fractures, osteoporosis, metastatic bone disease, Paget's disease, periodontal disease, cartilage degeneration, endometriosis, uterine fibroid disease, hot flashes, increased levels of LDL cholesterol, cardiovascular disease, impairment of cognitive functioning, cerebral degenerative disorders, restenosis, gynecomastia, vascular smooth muscle cell proliferation, obesity, incontinence, anxiety, depression resulting from an estrogen deficiency, and cancer, in particular of the breast, uterus and prostate. Combinations of the presently disclosed compounds with other agents useful in treating or preventing the disorders disclosed herein are within the scope of the invention. A person of ordinary skill in the art would be able to discern which combinations of agents would be useful based on the particular characteristics of the drugs and the disease involved. Such agents include the following: an organic bisphosphonate; a cathepsin K inhibitor; an estrogen or an estrogen receptor modulator; an androgen receptor modulator; an inhibitor of osteoclast proton ATPase; an inhibitor of HMG-CoA reductase; an integrin receptor antagonist; an osteoblast anabolic agent, such as PTH; calcitonin; Vitamin D or a synthetic Vitamin D analogue; selective serotonin reuptake inhibitors (SSRIs); and the pharmaceutically acceptable salts and mixtures thereof. A preferred combination is a compound of the present invention and an organic bisphosphonate. Another preferred combination is a compound of the present invention and a cathepsin K inhibitor. Another preferred combination is a compound of the present invention and an estrogen. Another preferred combination is a compound of the present invention and an androgen receptor modulator. Another preferred combination is a compound of the present invention and an osteoblast anabolic agent.

"Organic bisphosphonate" includes, but is not limited to, compounds of the chemical formula

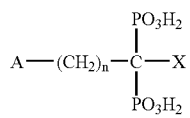

wherein n is an integer from 0 to 7 and wherein A and X are independently selected from the group consisting of H, OH, halogen, $NH_2$, SH, phenyl, $C_{1-30}$alkyl, $C_{3-30}$ branched or cycloalkyl, bicyclic ring structure containing two or three N, $C_{1-30}$ substituted alkyl, $C_{1-10}$alkyl substituted $NH_2$, $C_{3-10}$ branched or cycloalkyl substituted $NH_2$, $C_{1-10}$alkyl substituted $NH_2$, $C_{1-10}$alkoxy, $C_{1-10}$alkyl substituted thio, thiophenyl, halophenylthio, $C_{1-10}$alkyl substituted phenyl, pyridyl, furanyl, pyrrolidinyl, imidazolyl, imidazopyridinyl, and benzyl, such that both A and X are not selected from H or OH when n is 0; or A and X are taken together with the carbon atom or atoms to which they are attached to form a $C_{3-10}$ ring.

In the foregoing chemical formula, the alkyl groups can be straight, branched, or cyclic, provided sufficient atoms are selected for the chemical formula. The $C_{1-30}$ substituted alkyl can include a wide variety of substituents, nonlimiting examples which include those selected from the group consisting of phenyl, pyridyl, furanyl, pyrrolidinyl, imidazonyl, $NH_2$, $C_{1-10}$alkyl or diallyl substituted $NH_2$, OH, SH, and $C_{1-10}$alkoxy.

The foregoing chemical formula is also intended to encompass complex carbocyclic, aromatic and hetero atom structures for the A and/or X substituents, nonlimiting examples of which include naphthyl, quinolyl, isoquinolyl, adamantyl, and chlorophenylthio.

Pharmaceutically acceptable salts and derivatives of the bisphosphonates are also useful herein. Non-limiting examples of salts include those selected from the group consisting alkali metal, alkaline metal, ammonium, and mono-, di-, tri-, or tetra-$C_{1-30}$alkyl-substituted ammonium. Preferred salts are those selected from the group consisting of sodium, potassium, calcium, magnesium, and ammonium salts. More preferred are sodium salts. Non-limiting examples of derivatives include those selected from the group consisting of esters, hydrates, and amides.

It should be noted that the terms "bisphosphonate" and "bisphosphonates", as used herein in referring to the therapeutic agents of the present invention are meant to also encompass diphosphonates, biphosphonic acids, and diphosphonic acids, as well as salts and derivatives of these materials. The use of a specific nomenclature in referring to the bisphosphonate or bisphosphonates is not meant to limit the scope of the present invention, unless specifically indicated.

Nonlimiting examples of bisphosphonates include alendronate, cimadronate, clodronate, etidronate, ibandronate, incadronate, minodronate, neridronate, olpadronate, pamidronate, piridronate, risedronate, tiludronate, and zolendronate, and pharmaceutically acceptable salts and esters thereof. A particularly preferred bisphosphonate is alendronate, especially a sodium, potassium, calcium, magnesium or ammonium salt of alendronic acid. Exemplifying the preferred bisphosphonate is a sodium salt of alendronic acid, especially a hydrated sodium salt of alendronic acid. The salt can be hydrated with a whole number of moles of water or non whole numbers of moles of water. Further exemplifying the preferred bisphosphonate is a hydrated sodium salt of alendronic acid, especially when the hydrated salt is alendronate monosodium trihydrate.

The precise dosage of the organic bisphosphonate will vary with the dosing schedule, the particular bisphosphonate chosen, the age, size, sex and condition of the mammal or human, the nature and severity of the disorder to be treated, and other relevant medical and physical factors. For humans, an effective oral dose of bisphosphonate is typically from about 1.5 to about 6000 µg/kg body weight and preferably about 10 to about 2000 µg/kg of body weight. In alternative dosing regimens, the bisphosphonate can be administered at intervals other than daily, for example once-weekly dosing, twice-weekly dosing, biweekly dosing, and twice-monthly dosing. In a once weekly dosing regimen, alendronate monosodium trihydrate would be administered at dosages of 35 mg/week or 70 mg/week. The bisphosphonates may also be administered monthly, ever six months, yearly or even less frequently, see WO 01/97788 (published Dec. 27, 2001) and WO 01/89494 (published Nov. 29, 2001).

"Estrogen" includes, but is not limited to naturally occurring estrogens [7-estradiol ($E_2$), estrone ($E_1$), and estriol ($E_3$)], synthetic conjugated estrogens, oral contraceptives and sulfated estrogens. See, Gruber C J, Tschugguel W, Schneeberger C, Huber J C., "Production and actions of estrogens" N Engl J Med 2002 Jan. 31; 346(5):340–52.

"Estrogen receptor modulators" refers to compounds which interfere or inhibit the binding of estrogen to the receptor, regardless of mechanism. Examples of estrogen receptor modulators include, but are not limited to, estrogen, progestogen, estradiol, droloxifene, raloxifene, lasofoxifene, TSE-424, tamoxifen, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenyl-hydrazone, and SH646.

"Cathepsin K inhibitors" refers to compounds which interfere with the activity of the cysteine protease cathepsin K. Nonlimiting examples of cathepsin K inhibitors can be found in PCT publications WO 00/55126 to Axys Pharmaceuticals and WO 01/49288 to Merck Frosst Canada & Co. and Axys Pharmaceuticals.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"An inhibitor of osteoclast proton ATPase" refers to an inhibitor of the proton ATPase, which is found on the apical membrane of the osteoclast, and has been reported to play a significant role in the bone resorption process. This proton pump represents an attractive target for the design of inhibitors of bone resorption which are potentially useful for the treatment and prevention of osteoporosis and related metabolic diseases. See C. Farina et al., "Selective inhibitors of the osteoclast vacuolar proton ATPase as novel bone antiresorptive agents," DDT, 4:163–172 (1999)), which is hereby incorporated by reference in its entirety.

"HMG-CoA reductase inhibitors" refers to inhibitors of 3-hydroxy-3-methylglutaryl-CoA reductase. Compounds which have inhibitory activity for HMG-CoA reductase can be readily identified by using assays well-known in the art. For example, see the assays described or cited in U.S. Pat. No. 4,231,938 at col. 6, and WO 84/02131 at pp. 30–33. The terms "HMG-CoA reductase inhibitor" and "inhibitor of HMG-CoA reductase" have the same meaning when used herein.

Examples of HMG-CoA reductase inhibitors that may be used include but are not limited to lovastatin (MEVACOR® see U.S. Pat. Nos. 4,231,938, 4,294,926 and 4,319,039), simvastatin (ZOCOR®; see U.S. Pat. Nos. 4,444,784, 4,820,850 and 4,916,239), pravastatin (PRAVACHOL® see U.S. Pat. Nos. 4,346,227, 4,537,859, 4,410,629, 5,030,447 and 5,180,589), fluvastatin (LESCOL®; see U.S. Pat. Nos. 5,354,772, 4,911,165, 4,929,437, 5,189,164, 5,118,853, 5,290,946 and 5,356,896), atorvastatin (LIPITOR® see U.S. Pat. Nos. 5,273,995, 4,681,893, 5,489,691 and 5,342,952) and cerivastatin (also known as rivastatin and BAYCHOL®; see U.S. Pat. No. 5,177,080). The structural formulas of these and additional HMG-CoA reductase inhibitors that may be used in the instant methods are described at page 87 of M. Yalpani, "Cholesterol Lowering Drugs", *Chemistry & Industry*, pp. 85–89 (5 Feb. 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefor the use of such salts, esters, open-acid and lactone forms is included within the scope of this invention. An illustration of the lactone portion and its corresponding open-acid form is shown below as structures I and II.

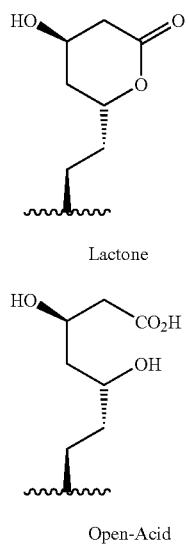

Lactone

Open-Acid

In HMG-CoA reductase inhibitors where an open-acid form can exist, salt and ester forms may preferably be formed from the open-acid, and all such forms are included within the meaning of the term "HMG-CoA reductase inhibitor" as used herein. Preferably, the HMG-CoA reductase inhibitor is selected from lovastatin and simvastatin, and most preferably simvastatin. Herein, the term "pharmaceutically acceptable salts" with respect to the HMG-CoA reductase inhibitor shall mean non-toxic salts of the compounds employed in this invention which are generally prepared by reacting the free acid with a suitable organic or inorganic base, particularly those formed from cations such as sodium, potassium, aluminum, calcium, lithium, magnesium, zinc and tetramethylammonium, as well as those salts formed from amines such as ammonia, ethylenediamine, N-methylglucamine, lysine, arginine, ornithine, choline, N,N'-dibenzylethylenediamine, chloroprocaine, diethanolamine, procaine, N-benzylphenethylamine, 1-p-chlorobenzyl-2-pyrrolidine-1'-yl-methylbenz-imidazole, diethylamine, piperazine, and tris(hydroxymethyl) aminomethane. Further examples of salt forms of HMG-CoA reductase inhibitors may include, but are not limited to, acetate, benzenesulfonate, benzoate, bicarbonate, bisulfate, bitartrate, borate, bromide, calcium edetate, camnsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylsulfate, mucate, napsylate, nitrate, oleate, oxalate, pamaote, palmitate, panthothenate, phosphate/diphosphate, polygalacturonate, salicylate, stearate, subacetate, succinate, tannate, tartrate, teoclate, tosylate, triethiodide, and valerate.

Ester derivatives of the described HMG-CoA reductase inhibitor compounds may act as prodrugs which, when absorbed into the bloodstream of a warm-blooded animal, may cleave in such a manner as to release the drug form and permit the drug to afford improved therapeutic efficacy.

As used above, "integrin receptor antagonists" refers to compounds which selectively antagonize, inhibit or counteract binding of a physiological ligand to the $\alpha_v\beta_3$ integrin, to compounds which selectively antagonize, inhibit or counter-act binding of a physiological ligand to the $\alpha_v\beta5$ integrin, to compounds which antagonize, inhibit or counteract binding of a physiological ligand to both the $\alpha_v\beta_3$ integrin and the $\alpha_v\beta_5$ integrin, and to compounds which antagonize, inhibit or counteract the activity of the particular integrin(s) expressed on capillary endothelial cells. The term also refers to antagonists of the $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins. The term also refers to antagonists of any combination of $\alpha_v\beta_3$, $\alpha_v\beta_5$, $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins. H. N. Lode and coworkers in PNAS USA 96:1591–1596 (1999) have observed synergistic effects between an antiangiogenic ccv integrin antagonist and a tumor-specific antibody-cytokine (interleukin-2) fusion protein in the eradication of spontaneous tumor metastases. Their results suggested this combination as having potential for the treatment of cancer and metastatic tumor growth. $\alpha_v\beta_3$ integrin receptor antagonists inhibit bone resorption through a new mechanism distinct from that of all currently available drugs. Integrins are heterodimeric transmembrane adhesion receptors that mediate cell-cell and cell-matrix interactions. The $\alpha$ and $\beta$ integrin subunits interact non-covalently and bind extracellular matrix ligands in a divalent cation-dependent manner. The most abundant integrin on osteoclasts is $\alpha_v\beta_3$ ($>10^7$/osteoclast), which appears to play a rate-limiting role in cytoskeletal organization important for cell migration and polarization. The $\alpha_v\beta_3$ antagonizing effect is selected from inhibition of bone resorption, inhibition of restenosis, inhibition of macular degeneration, inhibition of arthritis, and inhibition of cancer and metastatic growth.

"An osteoblast anabolic agent" refers to agents that build bone, such as PTH. The intermittent administration of parathyroid hormone (PTH) or its amino-terminal fragments and analogues have been shown to prevent, arrest, partially reverse bone loss and stimulate bone formation in animals and humans. For a discussion refer to D. W. Dempster et al., "Anabolic actions of parathyroid hormone on bone," Endocr Rev 14:690–709 (1993). Studies have demonstrated the clinical benefits of parathyroid hormone in stimulating bone formation and thereby increasing bone mass and strength. Results were reported by R M Neer et al., in New Eng J Med 344 1434–1441 (2001).

In addition, parathyroid hormone-related protein fragments or analogues, such as PTHrP-(1–36) have demonstrated potent anticalciuric effects [see M. A. Syed et al., "Parathyroid hormone-related protein-(1–36) stimulates renal tubular calcium reabsorption in normal human volunteers:implications for the pathogenesis of humoral hypercalcemia of malignancy," JCEM 86:1525–1531 (2001)] and may also have potential as anabolic agents for treating osteoporosis.

Calcitonin is a 32 amino acid pepetide produced primarily by the thyroid which is known to participate in calcium and phosphorus metabolism. Calcitonin suppresses resorption of bone by inhibiting the activity of osteoclasts. Thus, calcitonin can allow osteoblasts to work more effectively and build bone.

"Vitamin D" includes, but is not limited to, vitamin $D_3$ (cholecalciferol) and vitamin $D_2$ (ergocalciferol), which are naturally occurring, biologically inactive precursors of the hydroxylated biologically active metabolites of vitamin D: 1α-hydroxy vitamin D; 25-hydroxy vitamin D, and 1α,25-dihydroxy vitamin D. Vitamin $D_2$ and vitamin $D_3$ have the same biological efficacy in humans. When either vitamin $D_2$ or $D_3$ enters the circulation, it is hydroxylated by cytochrome $P_{450}$-vitamin D-25-hydroxylase to give 25-hydroxy vitamin D. The 25-hydroxy vitamin D metabolite is biologically inert and is further hydroxylated in the kidney by cytochrome P450-monooxygenase, 25 (OH) D-1α-hydroxylase to give 1,25-dihydroxy vitamin D. When serum calcium decreases, there is an increase in the production of parathyroid hormone (PTH), which regulates calcium homeostasis and increases plasma calcium levels by increasing the conversion of 25-hydroxy vitamin D to 1,25-dihydroxy vitamin D.

1,25-dihydroxy vitamin D is thought to be reponsible for the effects of vitamin D on calcium and bone metabolism. The 1,25-dihydroxy metabolite is the active hormone required to maintain calcium absorption and skeletal integrity. Calcium homeostasis is maintained by 1,25 dihydroxy vitamin D by inducing monocytic stem cells to differentiate into osteoclasts and by maintaining calcium in the normal range, which results in bone mineralization by the deposition of calcium hydroxyapatite onto the bone surface, see Holick, M F, Vitamin D photobiology, metabolism, and clinical applications, In: DeGroot L, Besser H, Burger H G, eg al., eds. *Endocrinology*, $3^{rd}$ ed., 990–1013 (1995). However, elevated levels of 1α25-dihydroxy vitamin $D_3$ can result in an increase of calcium concentration in the blood and in the abnormal control of calcium concentration by bone metabolism, resulting in hypercalcemia. 1α,25-dihydroxy vitamin $D_3$ also indirectly regulates osteoclastic activity in bone metabolism and elevated levels may be expected to increase excessive bone resorption in osteoporosis.

"Synthetic vitamin D analogues" includes non-naturally occurring compounds that act like vitamin D.

Selective Serotonin Reuptake Inhibitors act by increasing the amount of serotonin in the brain. SSRIs have been used successfully for a decade in the United States to treat depression. Non-limiting examples of SSRIs include fluoxetine, paroxetine, sertraline, citalopram, and fluvoxamine. SSRIs are also being used to treat disoreders realted to estrogen functioning, suchs as premenstrual syndrome and premenstrual dysmorphic disorder. See Sundstrom-Poromaa I, Bixo M, Bjorn I, Nordh O., "Compliance to antidepressant drug therapy for treatment of premenstrual syndrome," J Psychosom Obstet Gynaecol December 2000;21(4):205–11.

If formulated as a fixed dose, such combination products employ the compounds of this invention within the dosage range described below and the other pharmaceutically active agent(s) within its approved dosage range. Compounds of the instant invention may alternatively be used sequentially with known pharmaceutically acceptable agent(s) when a combination formulation is inappropriate.

The term "administration" and variants thereof (e.g., "administering" a compound) in reference to a compound of the invention means introducing the compound or a prodrug of the compound into the system of the animnal in need of treatment. When a compound of the invention or prodrug thereof is provided in combination with one or more other active agents (e.g., a bisphosphonate, etc.), "administration" and its variants are each understood to include concurrent and sequential introduction of the compound or prodrug thereof and other agents. The present invention includes within its scope prodrugs of the compounds of this invention. In general, such prodrugs will be functional derivatives of the compounds of this invention which are readily convertible in vivo into the required compound. Thus, in the methods of treatment of the present invention, the term "administering" shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs," ed. H. Bundgaard, Elsevier, 1985, which is incorporated by reference herein in its entirety. Metabolites of these compounds include active species produced upon introduction of compounds of this invention into the biological, milieu.

The present invention also encompasses a pharmaceutical composition useful in the treatment of osteoporosis or other bone disorders, comprising the administration of a therapeutically effective amount of the compounds of this invention, with or without pharmaceutically acceptable carriers or diluents. Suitable compositions of this invention include aqueous solutions comprising compounds of this invention and pharmacologically acceptable carriers, e.g., saline, at a pH level, e.g., 7.4. The solutions may be introduced into a patient's bloodstream by local bolus injection.

When a compound according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of compound is administered to a mammal undergoing treatment. Oral dosages of the present invention, when used for the indicated effects, will range between about 0.01 mg per kg of body weight per day (mg/kg/day) to about 100 mg/kg/day, preferably 0.01 to 10 mg/kg/day, and most preferably 0.1 to 5.0 mg/kg/day. For oral administration, the compositions are preferably provided in the form of tablets containing 0.01, 0.05, 0.1, 0.5, 1.0, 2.5, 5.0, 10.0, 15.0, 25.0, 50.0, 100 and 500 milligrams of the active ingredient for the symptomatic adjustment of the dosage to the patient to be treated. A medicament typically contains from about 0.01 mg to about 500 mg of the active ingredient, preferably, from about 1 mg to about 100 mg of active ingredient. Intravenously, the most preferred doses will range from about 0.1 to about 10 mg/kg/minute during a constant rate infusion. Advantageously, compounds of the present invention may be administered in a single daily dose, or the total daily dosage may be administered in divided doses of two, three or four times daily. Furthermore, preferred compounds for the present invention can be administered in intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than intermittant throughout the dosage regimen.

The compounds of the present invention can be used in combination with other agents useful for treating estrogen-mediated conditions. The individual components of such combinations can be administered separately at different times during the course of therapy or concurrently in divided or single combination forms. The instant invention is therefore to be understood as embracing all such regimes of simultaneous or alternating treatment and the term "administering" is to be interpreted accordingly. It will be understood that the scope of combinations of the compounds of this invention with other agents useful for treating cathepsin-mediated conditions includes in principle any combination with any pharmaceutical composition useful for treating disorders related to estrogen functioning.

The scope of the invention therefore encompasses the use of the instantly claimed compounds in combination with a second agent selected from: an organic bisphosphonate; a cathepsin K inhibitor; an estrogen; an estrogen receptor modulator; an androgen receptor modulator; an inhibitor of osteoclast proton ATPase; an inhibitor of HMG-CoA reductase; an integrin receptor antagonist; an osteoblast anabolic agent; calcitonin; Vitamin D; a synthetic Vitamin D analogue; a selective serotonin reuptake inhibitor; and the pharmaceutically acceptable salts and mixtures thereof.

These and other aspects of the invention will be apparent from the teachings contained herein.

Definitions

As used herein, the term "composition" is intended to encompass a product comprising the specified ingredients in the specified amounts, as well as any product which results, directly or indirectly, from combination of the specified ingredients in the specified amounts.

The term "therapeutically effective amount" as used herein means that amount of active compound or pharmaceutical agent that elicits the biological or medicinal response in a tissue, system, animal or human that is being sought by a researcher, veterinarian, medical doctor or other clinician.

The terms "treating" or "treatment" of a disease as used herein includes:preventing the disease, i.e. causing the clinical symptoms of the disease not to develop in a mammal that may be exposed to or predisposed to the disease but does not yet experience or display symptoms of the disease; inhibiting the disease, i.e., arresting or reducing the development of the disease or its clinical symptoms; or relieving the disease, i.e., causing regression of the disease or its clinical symptoms.

The term "bone resorption," as used herein, refers to the process by which osteoclasts degrade bone.

The term "alkyl" shall mean a substituting univalent group derived by conceptual removal of one hydrogen atom from a straight or branched-chain acyclic saturated hydrocarbon (i.e., —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$C(CH_3)_3$, etc.).

The term "alkenyl" shall mean a substituting univalent group derived by conceptual removal of one hydrogen atom from a straight or branched-chain acyclic unsaturated hydrocarbon containing at least one double bond (i.e., —$CH=CH_2$, —$CH_2CH=CH_2$, —$CH=CHCH_3$, —$CH_2CH=C(CH_3)_2$, etc.).

The term "alkynyl" shall mean a substituting univalent group derived by conceptual removal of one hydrogen atom from a straight or branched-chain acyclic unsaturated hydrocarbon containing at least one triple bond (i.e., —$C\equiv CH$, —$CH_2C\equiv H$, —$C\equiv CCH_3$, —$CH_2C\equiv CCH_2(CH_3)_2$, etc.)

The term "alkylene" shall mean a substituting bivalent group derived from a straight or branched-chain acyclic saturated hydrocarbon by conceptual removal of two hydrogen atoms from different carbon atoms (i.e., —$CH_2CH_2$—, —$CH_2CH_2CH_2CH_2$—, —$CH_2C(CH_3)_2CH_2$—, etc.).

The term "alkylidene" shall mean a substituting bivalent group derived from a straight or branched-chain acyclic saturated hydrocarbon by conceptual removal of two hydrogen atoms from the same carbon atom (i.e., =$CH_2$, =$CHCH_3$, =$C(CH_3)_2$, etc.).

The term "alkenylene" shall mean a substituting bivalent group derived from a straight or branched-chain acyclic unsaturated hydrocarbon by conceptual removal of two hydrogen atoms from different carbon atoms (i.e., —$CH=CH$—, —$CH_2CH=CH$—, $CH_2CH=CHCH_2$—, —$C(CH_3)=C(CH_3)$—, etc.).

The term "cycloalkyl" shall mean a substituting univalent group derived by conceptual removal of one hydrogen atom from a saturated monocyclic hydrocarbon (i.e., cyclopropyl, cyclobutyl, cyclopentyl, cyclohexyl, or cycloheptyl).

The term "cycloalkenyl" shall mean a substituting univalent group derived by conceptual removal of one hydrogen atom from an unsaturated monocyclic hydrocarbon containing a double bond (i.e., cyclopentenyl or cyclohexenyl).

The term "heterocycloalkyl" shall mean a substituting univalent group derived by conceptual removal of one hydrogen atom from a heterocycloalkane wherein said heterocycloalkane is derived from the corresponding saturated monocyclic hydrocarbon by replacing one or two carbon atoms with atoms selected from N, O or S. Examples of heterocycloalkyl groups include, but are not limited to, oxiranyl, azetidinyl, pyrrolidinyl, piperidinyl, piperazinyl, and morpholinyl. Heterocycloalkyl substituents can be attached at a carbon atom. If the substituent is a nitrogen containing heterocycloalkyl substituent, it can be attached at the nitrogen atom.

The term "aryl" as used herein refers to a substituting univalent group derived by conceptual removal of one hydrogen atom from a mnonocyclic or bicyclic aromatic hydrocarbon. Examples of aryl groups are phenyl, indenyl, and naphthyl.

The term "heteroaryl" as used herein refers to a substituting univalent group derived by the conceptual removal of one hydrogen atom from a monocyclic or bicyclic aromatic ring system containing 1, 2, 3, or 4 heteroatoms selected from N, O, or S. Examples of heteroaryl groups include, but are not limited to, pyrrolyl, furyl, thienyl, imidazolyl, pyrazolyl, oxazolyl, isoxazolyl, thiazolyl, pyridyl, pyrimidinyl, pyrazinyl, benzimidazolyl, indolyl, and purinyl. Hetaryl substituents can be attached at a carbon atom or through the heteroatom.

In the compounds of the present invention, allyl, alkenyl, alkynyl, alkylidene, alkenylene, cycloalkyl, cycloalkenyl, heterocycloalkyl, aryl and heteroaryl groups can be further substituted by replacing one or more hydrogen atoms by alternative non-hydrogen groups. These include, but are not limited to, halo, hydroxy, mercapto, amino, carboxy, cyano, carbamoyl, and oxo.

Whenever the term "alkyl" or "aryl" or either of their prefix roots appear in a name of a substituent (e.g., aryl $C_{0-8}$alkyl) it shall be interpreted as including those limitations given above for "alkyl" and "aryl." Designated numbers of carbon atoms (e.g., $C_{1-10}$) shall refer independently to the number of carbon atoms in an alkyl or cyclic alkyl moiety or to the alkyl portion of a larger substituent in which alkyl appears as its prefix root.

The terms "arylalkyl" and "alkylaryl" include an alkyl portion where alkyl is as defined above and to include an aryl portion where aryl is as defined above. Examples of arylalkyl include, but are not limited to, benzyl, fluorobenzyl, chlorobenzyl, phenylethyl, phenylpropyl, fluorophenylethyl, chlorophenylethyl, thienylmethyl, thienylethyl, and thienylpropyl. Examples of alkylaryl include, but are not limited to, toluyl, ethylphenyl, and propylphenyl.

The term "(heteroaryl)alkyl," as used herein, shall refer to a system that includes a heteroaryl portion, where heteroaryl is as defined above, and contains an alkyl portion. Examples of (heteroaryl)alkyl include, but are limited to, pyridylmethyl, pyridylethyl and imidazoylmethyl.

The term "(cycloalkyl)alkyl," as used herein, shall refer to a system that includes a 3- to 7-membered fully saturated cyclic ring portion and also includes an alkyl portion, wherein cycloalkyl and alkyl are as defined above.

The term "(cycloalkyl)alkenyl," as used herein, shall refer to a system that includes a 3- to 7-membered fully saturated cyclic ring portion and also includes an alkenyl portion, wherein cycloalkyl and alkenyl are as defined above.

The term "(cycloalkenyl)alkyl," as used herein, shall refer to a system that includes a 4- to 7-membered cyclic ring portion containing at least one carbon to carbon double bond and also includes an alkyl portion, wherein cycloalkenyl and alkyl are as defined above.

The term "(heterocycloalkyl)alkyl," as used herein, shall refer to a system that includes a 3- to 7-membered heterocycloalkyl ring portion and also includes an alkyl portion, wherein heterocycloalkyl and alkyl are as defined above.

In the compounds of the present invention, $R^1$ and $R^2$ can be taken together with the carbon atom to which they are attached to form a 3–6 membered ring.

In the compounds of the present invention, $R^a$ and $R^b$ can be taken together with any of the atoms to which they may be attached or are between them to form a 4–6 membered ring system.

The term "halo" shall include iodo, bromo, chloro and fluoro.

The term "oxy" means an oxygen (O) atom. The term "thio" means a sulfur (S) atom. The term "oxo" means =O. The term "oximino" means the =N—O group.

The term "substituted" shall be deemed to include multiple degrees of substitution by a named substitutent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

The present invention also includes N-oxide derivatives and protected derivatives of compounds of Formula I. For example, when compounds of Formula I contain an oxidizable nitrogen atom, the nitrogen atom can be converted to an N-oxide by methods well known in the art. Also when compounds of Formula I contain groups such as hydroxy, carboxy, thiol or any group containing a nitrogen atom(s), these groups can be protected with a suitable protecting groups. A comprehensive list of suitable protective groups can be found in T. W. Greene, Protective Groups in Organic Synthesis, John Wiley & Sons, Inc. 1981, the disclosure of which is incorporated herein by reference in its entirety. The protected derivatives of compounds of Formula I can be prepared by methods well known in the art.

The alkyl, alkenyl, alkynyl, cycloalkyl, cycloalkenyl, aryl, heterocycloalkyl and heteroaryl substituents may be unsubstituted or unsubstituted, unless specifically defined otherwise. For example, a $C_{1-10}$alkyl may be substituted with one or more substituents selected from hydroxy, oxo, halogen, alkoxy, dialkylamino, or carboxy, and so on. In the case of a disubstituted alkyl, for instance, wherein the substituents are oxo and OH, the following are included in the definition: —(C=O)CH$_2$CH(OH)CH$_3$, —(C=O)OH, —CH$_2$(OH)CH$_2$CH(O), and so on. In the case of substituted alkyl, for instance, where the substituents are 1–5 fluoro, the following are included in the definition: —CHF$_2$, —CF$_3$, —CF$_2$CH$_3$, —CH$_2$CF$_3$, —CF$_2$CF$_3$, —CH$_2$CF$_2$CH$_3$, —CH$_2$CHF$_2$, —CH$_2$CF$_2$CF$_3$, —CH$_2$CF$_2$CH$_2$CH$_3$, —CH$_2$CH$_2$CF$_2$CH$_3$, —CH$_2$CH$_2$CF$_2$CF$_3$, —CH$_2$CF(CH$_3$)$_2$, and so on. In the case of a cycloalkylalkyl group, for instance, wherein the substituents are 1–3 $C_{1-3}$alkyl, the following are included in the definition:

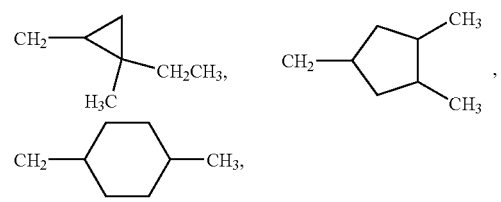

an so on.

The compounds of the present invention may have asymmetric centers, chiral axes, and chiral planes (as described in: E. L. Eliel and S. H. Wilen, Stereo-chemistry of Carbon Compounds, John Wiley & Sons, New York, 1994, pages 1119–1190), and occur as racemates, racemic mixtures, and as individual diastereomers, with all possible isomers and mixtures thereof, including optical isomers, being included in the present invention. In addition, the compounds disclosed herein may exist as tautomers and both tautomeric forms are intended to be encompassed by the scope of the invention, even though only one tautomeric structure is depicted. For example, any claim to compound A below is understood to include tautomeric structure B, and vice versa, as well as mixtures thereof.

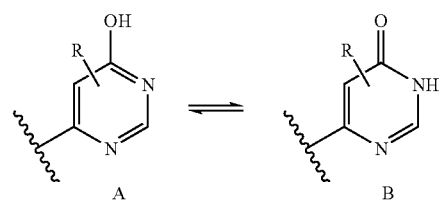

When any variable (e.g. $R^a$, $R^b$, $R^c$ etc.) occurs more than one time in any constituent, its definition on each occurrence is independent at every other occurrence. Also, combinations of substituents and variables are permissible only if such combinations result in stable compounds. Lines drawn into the ring systems from substituents indicate that the indicated bond may be attached to any of the substitutable ring carbon atoms. If the ring system is polycyclic, it is intended that the bond be attached to any of the suitable carbon atoms on the proximal ring only.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. The phrase "optionally substituted with one or more substituents" should be taken to be equivalent to the phrase "optionally substituted with at least one substituent" and in such cases the preferred embodiment will have from zero to three substituents.

Under standard nonmenclature used throughout this disclosure, the terminal portion of the designated side chain is described first, followed by the adjacent functionality toward the point of attachment. For example, a $C_{1-5}$ alkyl-carbonylamino $C_{1-6}$alkyl substituent is equivalent to

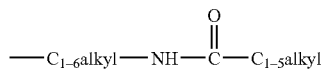

In choosing compounds of the present invention, one of ordinary skill in the art will recognize that the various substituents, i.e. $R^1$, $R^2$, $R^3$, $R^4$, $R^5$, $R^6$, $R^7$, $R^8$, $R^9$, $R^{10}$, $R^a$, $R^b$, $R^c$, $R^d$, $R^e$, $YR^d$ and $ZR^d$ are to be chosen in conformity with well-known principles of chemical structure connectivity.

Representative compounds of the present invention typically display submicromolar affinity for alpha and/or beta estrogen receptors. Compounds of this invention are therefore useful in treating mammals suffering from disorders related to estrogen functioning. Pharmacologically effective amounts of the compound, including the pharmaceutically effective salts thereof, are administered to the mammal, to treat disorders related to estrogen functioning, such as bone loss, hot flashes and cardiovascular disease.

The compounds of the present invention are available in racemic form or as individual enantiomers. For convenience, some structures are graphically represented as a single enantiomer but, unless otherwise indicated, is meant to include both racemic and enantiomerically pure forms. Where cis and trans sterochemistry is indicated for a compound of the present invention, it should be noted that the stereochemistry should be construed as relative, unless indicated otherwise. For example, a (+) or (−) designation should be construed to represent the indicated compound with the absolute stereochemistry as shown.

Racemic mixtures can be separated into their individual enantiomers by any of a number of conventional methods. These include, but are not limited to, chiral chromatography, derivatization with a chiral auxiliary followed by separation by chromatography or crystallization, and fractional crystallization of diastereomeric salts. Deracemization procedures may also be employed, such as enantiomeric protonation of a pro-chiral intermediate anion, and the like.

The compounds of the present invention can be used in combination with other agents useful for treating estrogen-mediated conditions. The individual components of such combinations can be administered separately at different times during the course of therapy or concurrently in divided or single combination forms. The instant invention is therefore to be understood as embracing all such regimes of simultaneous or alternating treatment and the term "administering" is to be interpreted accordingly. It will be understood that the scope of combinations of the compounds of this invention with other agents useful for treating estrogen-mediated conditions includes in principle any combination with any pharmaceutical composition useful for treating disorders related to estrogen functioning.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician, veterinarian or clinician can readily determine and prescribe the effective amount of the drug required to prevent, counter or arrest the progress of the condition.

In the methods of the present invention, the compounds herein described in detail can form the active ingredient, and are typically administered in admixture with suitable pharmaceutical diluents, excipients or carriers (collectively referred to herein as 'carrier' materials) suitably selected with respect to the intended form of administration, that is, oral tablets, capsules, elixirs, syrups and the like, and consistent with conventional pharmaceutical practices.

The pharmaceutically acceptable salts of the compounds of this invention include the conventional non-toxic salts of the compounds of this invention as formed inorganic or organic acids. For example, conventional non-toxic salts include those derived from inorganic acids such as hydrochloric, hydrobromic, sulfuric, sulfamic, phosphoric, nitric and the like, as well as salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like. The preparation of the pharmaceutically acceptable salts described above and other typical pharmaceutically acceptable salts is more fully described by Berg et al., "Pharmaceutical Salts," *J. Pharm. Sci.*, 1977:66:1–19, hereby incorporated by reference. The pharmaceutically acceptable salts of the compounds of this invention can be synthesized from the compounds of this invention which contain a basic or acidic moiety by conventional chemical methods. Generally, the salts of the basic compounds are prepared either by ion exchange chromatography or by reacting the free base with stoichiometric amounts or with an excess of the desired salt-forming inorganic or organic acid in a suitable solvent or various combinations of solvents. Similarly, the salts of the acidic compounds are formed by reactions with the appropriate inorganic or organic base.

The novel compounds of the present invention can be prepared according to the following schemes, using appropriate materials, and are exemplified by the subsequent specific examples. The compounds illustrated in the examples are not, however, to be construed as forming the only genus that is considered as the invention. Those skilled in the art will readily understand that known variations of the

27 conditions and processes of the following preparative procedures can be used to prepare these compounds. All temperatures are degrees Celsius unless otherwise noted.

The following specific examples, while not limiting, serve to illustrate the methods of preparation of the 1,2,9,9a-tetrahydro-3H-fluoren-3-one compounds of the present invention. All compounds prepared are racemic, but could be resolved if desired using known methodologies.

EXAMPLE 1

SYNTHESIS OF 7-AMINO-4,6-DIBROMO-9a-BUTYL-1,2,9,9a-TETRAHYDRO-3H-FLUOREN-3-ONE and 7-AMINO-4,8-DIBROMO-9a-BUTYL-1,2,9,9a-TETRAHYDRO-3H-FLUOREN-3-ONE

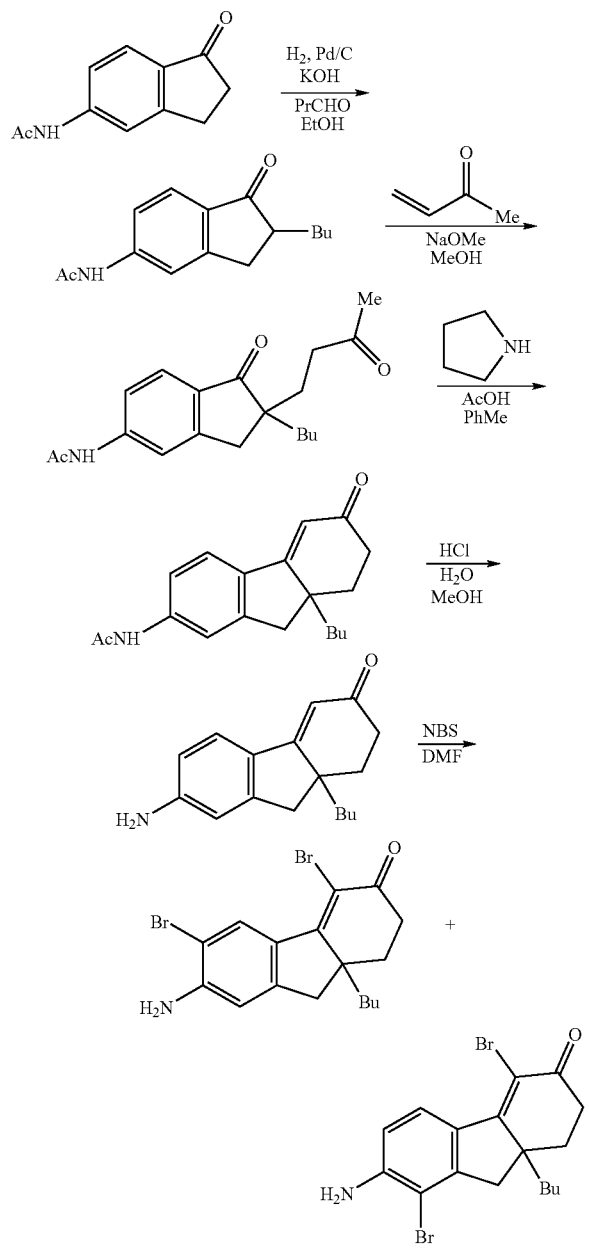

28

Step 1: 5-(acetylamino)-2-butyl-1-indanone 5-(Acetylamino)-1-indanone (10.0 g, 52.3 mmol) was added to a solution of KOH (87.7%, 0.66 g, 10.3 mmol) in EtOH (200 mL). The resulting suspension was stirred at room temperature while butyraldehyde (6.1 mL, 67.8 mmol) was added dropwise over two minutes. After stirring at room temperature for an additional 15 minutes, the mixture was treated with 10% Pd/C and stirred under a $H_2$ atmosphere (balloon) for 19 hours. The mixture was filtered through a pad of silica gel and the pad washed with EtOAc. The filtrate was washed with 1N HCl, 5% $NaHCO_3$, water, and brine, dried over $MgSO_4$, filtered, and concentrated under vacuum to an orange oil (12 g). The crude product was purified by Biotage flash chromatography on a 75 L silica gel column (7.5×35 cm), eluting with 2:1 hexane-EtOAc, to afford 5-(acetylamino)-2-butyl-1-indanone (8.8 g, 69%) as a clear oil.

Step 2: 5-(acetylamino)-2-butyl-2-(3-oxobutyl)-1-indanone

A solution of 5-(acetylamino)-2-butyl-1-indanone (8.8 g, 35.9 mmol) in MeOH (95 mL) was treated with 0.5M NaOMe in MeOH (14.4 mL, 7.2 mmol). The resulting solution was placed under a $N_2$ atmosphere, treated with methyl vinyl ketone (4.5 mL, 54 mmol), and then stirred at room temperature for three days. The mixture was partitioned between EtOAc and saturated aqueous $NH_4Cl$, and the aqueous phase was back-extracted with EtOAc. The combined organics were washed with 5% $NaHCO_3$, water, and brine, dried over $MgSO_4$, filtered, and concentrated under vacuum to an oil (11.8 g). The crude product was purified by Biotage flash chromatography on a 75 L silica gel column (7.5×35 cm), eluting with 2:1 hexane-EtOAc, to provide 5-(acetylamino)-2-butyl-2-(3-oxobutyl)-1-indanone (9.8 g, 87%) as a clear oil.

Step 3: 7-(acetylamino)-9a-butyl-1,2,9,9a-tetrahydro-3H-fluoren-3-one

A solution of 5-(acetylamino)-2-butyl-2-(3-oxobutyl)-1-indanone (9.8 g, 31.1 mmol) in toluene (300 mL) was treated with pyrrolidine (2.6 mL, 31 mmol) and acetic acid (1.8 mL, 31 mmol). The mixture was stirred under a $N_2$ atmosphere and heated in an oil bath at 90° C. for two hours. After cooling, the mixture was diluted with EtOAc (500 mL), washed with water, 5% $NaHCO_3$, water, and brine, dried over $MgSO_4$, filtered, and concentrated under vacuum to an orange-brown foam (7.0 g). $^1$H NMR of the crude product showed 7-(acetylamino)-9a-butyl-1,2,9,9a-tetrahydro-3H-fluoren-3-one along with 14–17% of a by-product identified as 9a-butyl-4-methyl-8,9,9a,10-tetrahydro-7H-indeno[1,2-g]quinolin-7-one.

Step 4: 7-amino-9a-butyl-1,2,9,9a-tetrahydro-3H-fluoren-3-one

The crude product from step 3 (7.0 g) was dissolved in MeOH (100 mL) and the solution was diluted with 6N HCl (100 mL). The resulting brown solution was stirred and heated in an oil bath at 80° C. for one hour. After cooling, the mixture was diluted with EtOAc (300 mL), stirred, and neutralized by the careful addition of aqueous 5% $NaHCO_3$ and solid $NaHCO_3$. The layers were separated and the aqueous portion was extracted with EtOAc (100 mL). The combined organics were washed with water and brine, dried over $MgSO_4$, filtered, and concentrated under vacuum to an orange-red solid. The crude product was purified by Biotage flash chromatography on a 75 L silica gel column (7.5×35 cm), eluting with 2:1 hexane-EtOAc. The product-containing fractions were evaporated under vacuum to an orange solid (4.2 g) which was shown by $^1$H NMR to contain 7-amino-9a-butyl-1,2,9,9a-tetrahydro-3H-fluoren-3-one along with approximately 10% of the 9a-butyl-4-methyl-8,9,9a,10-tetrahydro-7H-indenol[1,2-g]quinolin-7-one by-product. This material was used in the next step without further purification.

Step 5: 7-amino-4,6-dibromo-9a-butyl-1,2,9,9a-tetrahydro-3H-fluoren-3-one and 7-amino-4,8-dibromo-9a-butyl-1,2,9,9a-tetrahydro-3H-fluoren-3-one The mixture from step 4 (4.2 g) was dissolved in anhydrous N,N-dimethylformamide (DMF, 50 mL). The solution was placed under a N2 atmosphere, cooled in a −35° C. bath, and stirred while a solution of N-bromosuccinimide (5.6 g, 31.5 mmol) in DMF (20 mL) was added dropwise over 35 minutes. After stirring in the cold for an additional 15 minutes, the mixture was diluted with EtOAc (300 mL), washed with water, 5% NaHCO₃, and brine, dried over MgSO₄, filtered, and concentrated under vacuum. The residue was purified by Biotage flash chromatography on a 75 L silica gel column (7.5×35 cm), eluting with 2:1 hexane-EtOAc. The product-containing fractions were separated into three groups. The first grouping gave 7-amino-4,8-dibromo-9a-butyl-1,2,9,9a-tetrahydro-3H-fluoren-3-one (2.7 g) as a yellow-orange foam. The second grouping gave a 1:1 mixture (0.5 g) of 7-amino-4,8-dibromo-9a-butyl-1,2,9,9a-tetrahydro-3H-fluoren-3-one and 7-amino-4,6-dibromo-9a-butyl-1,2,9,9a-tetrahydro-3H-fluoren-3-one as a yellow-orange foam. The third grouping gave 7-amino-4,6-dibromo-9a-butyl-1,2,9,9a-tetrahydro-3H-fluoren-3-one (2.5 g) as a yellow powder. The 1:1 mixture was repurified to give 0.2 g each of the separate isomers.

4,6-Dibromo-isomer: $^1$H NMR (CDCl₃, 500 MHz) δ 0.85 (t, CH₂CH₂CH₂CH₃), 1.13–1.29 (m, CH₂CH₂CH₂CH₃), 1.45 and 1.63 (two m, CH₂CH₂CH₂CH₃), 2.04 and 2.22 (two ddd, 1-CH₂), 2.65–2.77 (m, 2-CH₂), 2.67 and 2.90 (two d, 9-CH₂), 6.68 (s, H-8), and 8.65 (s, H-5).

4,8-Dibromo-isomer: $^1$H NMR (CDCl₃, 500 MHz) δ 0.85 (t, CH₂CH₂CH₂CH₃), 1.15–1.30 (m, CH₂CH₂CH₂CH₃), 1.49 and 1.65 (two m, CH₂CH₂CH₂CH₃), 2.06 and 2.26 (two ddd, 1-CH₂), 2.64–2.78 (m, 2-CH₂), 2.71 and 3.03 (two d, 9-CH₂), 4.55 (br s, NH₂), 6.75 (d, H-6), and 8.34 (d, H-5).

EXAMPLE 2

SYNTHESIS OF 7-AMINO-4-BROMO-9a-BUTYL-8-CHLORO-6-FLUORO-1,2,9,9a-TETRAHYDRO-3H-FLUOREN-3-ONE

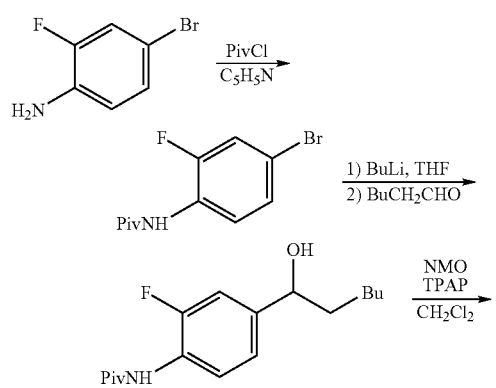

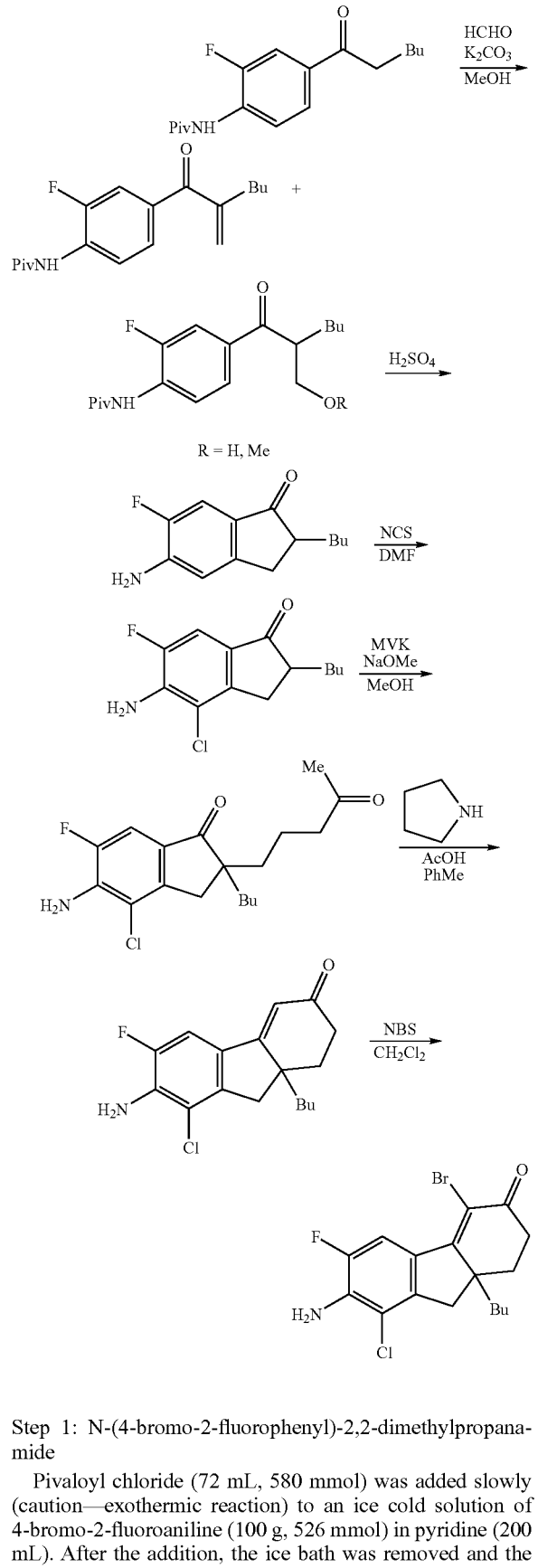

Step 1: N-(4-bromo-2-fluorophenyl)-2,2-dimethylpropanamide

Pivaloyl chloride (72 mL, 580 mmol) was added slowly (caution—exothermic reaction) to an ice cold solution of 4-bromo-2-fluoroaniline (100 g, 526 mmol) in pyridine (200 mL). After the addition, the ice bath was removed and the hot reaction mixture was stirred at room temperature for 30 minutes. The mixture was poured into cold water (500 mL) and the precipitated product was collected by filtration and washed with 1N HCl. The solid was dissolved in EtOAc (1 L), dried over MgSO$_4$, filtered, and concentrated under vacuum to provide N-(4-bromo-2-fluorophenyl)-2,2-dimethylpropanamide (125 g).

Step 2: N-[2-fluoro-4-(1-hydroxyhexyl)phenyl]-2,2-dimethylpropanamide

A solution of N-(4-bromo-2-fluorophenyl)-2,2-dimethylpropanamide (22.6 g, 82.5 mmol) in anhydrous tetrahydrofuran (410 mL) was placed under a nitrogen atmosphere, cooled in a dry ice-acetone bath, and stirred while butyllithium (83 mL of a 2.5M solution in hexanes, 207.5 mmol) was added dropwise by syringe pump over 2.5 hours. The resulting mixture was aged at −78° C. for 30 minutes and then treated with hexanal (25 mL, 208 mmol) added dropwise by syringe pump over 135 minutes. After stirring at −78° C. for an additional 70 minutes, the mixture was removed from the cooling bath, treated with aqueous 50% saturated NH$_4$Cl, and the layers separated. The aqueous portion was extracted with EtOAc. The combined organics were washed with aqueous NaHCO$_3$ and brine, dried over MgSO$_4$, filtered, and concentrated under vacuum to an oil. The crude product was purified by flash chromatography on a Biotage 75 L KP-Sil column, eluting with 4:1 hexanes-EtOAc (25×400 mL fractions). Fractions 9–22 were combined and evaporated under vacuum to afford N-[2-fluoro-4-(1-hydroxyhexyl)phenyl]-2,2-dimethylpropanamide (18.5 g, 76%) as a clear oil.

Step 3: N-(2-fluoro-4-hexanoylphenyl)-2,2-dimethylpropanamide

A solution of N-[2-fluoro-4-(1-hydroxyhexyl)phenyl]-2,2-dimethylpropanamide (18.5 g, 62.6 mmol) in CH$_2$Cl$_2$ (300 mL) was treated with 4-methylmorpholine N-oxide (7.35 g, 62.6 mmol) followed by tetrapropylammonium perruthenate (TPAP, 0.22 g, 0.63 mmol). The mixture was stirred at room temperature for 30 minutes, then treated with additional TPAP (0.88 g, 2.5 mmol) and stirred an additional 30 minutes at room temperature. The mixture was filtered through a pad of MgSO$_4$ atop a pad of silica gel, washing through with EtOAc (500 mL). The filtrate was evaporated under vacuum to afford N-(2-fluoro-4-hexanoylphenyl)-2,2-dimethylpropanamide (17.8 g, 97%) as a white solid.

Step 4: N-[4-(2-butylacryloyl)-2-fluorophenyl]-2,2-dimethylpropanamide, N-{2-fluoro-4-[2-(hydroxymethyl)hexanoyl]phenyl}-2,2-dimethylpropanamide, and N-{2-fluoro-4-[2-(methoxymethyl)hexanoyl]phenyl]-2,2-dimethylpropanamide A solution of N-(2-fluoro-4-hexanoylphenyl)-2,2-dimethylpropanamide (17.8 g, 60.7 mmol) in methanol (75 mL) was treated successively with K$_2$CO$_3$ (8.4 g, 60.7 mmol) and formaldehyde (37 wt. % solution in water, 5.0 mL, 67 mmol). The mixture was placed under a nitrogen atmosphere, stirred, and heated in an oil bath at 55° C. for 4 hours. After cooling to room temperature, the mixture was diluted with CH$_2$Cl$_2$ (300 mL), dried over MgSO$_4$, and filtered through a pad of silica gel, using more CH$_2$Cl$_2$ (200 mL) to wash the pad. The filtrate and washings were concentrated under vacuum to provide a mixture (19.5 g) of N-[4-(2-butylacryloyl)-2-fluorophenyl]-2,2-dimethylpropanamide, N-{2-fluoro-4-[2-(hydroxymethyl)hexanoyl]phenyl]-2,2-dimethylpropanamide, and N-{2-fluoro-4-[2-(methoxymethyl)hexanoyl]phenyl]-2,2-dimethylpropanamide.

Step 5: 5-amino-2-butyl-6-fluoro-1-indanone

A solution of the product mixture from step 4 (19.5 g, approx. 60.7 mmol) in CH$_2$Cl$_2$ (10 mL) was cooled in an ice bath and treated with ice-cold, conc. H$_2$SO$_4$ (300 mL). The resulting mixture was removed from the cooling bath and stirred at room temperature for 18 hours. The mixture was cautiously added to an ice-cold mixture of CH$_2$Cl$_2$ (300 mL) and chopped ice (1 L). Excess acid was neutralized by portionwise addition of saturated Na$_2$CO$_3$ solution (approx. 1 L) followed by solid Na$_2$CO$_3$ (approx. 500 g). Additional water and CH$_2$Cl$_2$ were occasionally added to dissolve the red/purple solids that formed during the neutralization. When the pH was neutral, the organic phase was separated and the aqueous portion was extracted with more CH$_2$Cl$_2$. The combined organics were washed with brine, dried over MgSO$_4$, filtered, and concentrated under vacuum. The residual dark red oil was purified by flash chromatography on a Biotage 75 L KP-Sil column, eluting with 4:1 hexanes-EtOAc. The product containing fractions were combined and evaporated under vacuum to provide 5-amino-2-butyl-6-fluoro-1-indanone (5.5 g, 37%) as a yellow solid.

Step 6: 5-amino-2-butyl-4-chloro-6-fluoro-1-indanone

A solution of 5-amino-2-butyl-6-fluoro-1-indanone (5.14 g, 23.2 mmol) in N,N-dimethylformamide (23 mL) was placed under a nitrogen atmosphere and treated with N-chlorosuccinimide (3.2 g, 24 mmol). After stirring at room temperature for 3 hours, the reaction mixture was partitioned between EtOAc and water. The organic portion was washed with water and brine, dried over MgSO$_4$, filtered, and evaporated under vacuum to an orange solid (6.5 g). The crude product was purified by flash chromatography on a Biotage 40M KP-Sil column, eluting with 9:1 hexanes-EtOAc. The product containing fractions were evaporated under vacuum to afford 5-amino-2-butyl-4-chloro-6-fluoro-1-indanone (5.2 g, 88%) as a yellow solid.

Step 7: 5-amino-2-butyl-4-chloro-6-fluoro-2-(3-oxobutyl)-1-indanone

A solution of 5-amino-2-butyl-4-chloro-6-fluoro-1-indanone (2.705 g, 10.6 mmol) in methanol (17 mL) was treated with sodium methoxide (0.5M solution in MeOH, 4.2 mL, 2.1 mmol) and methyl vinyl ketone (1.3 mL, 15.75 mmol). The resulting solution was stirred under a nitrogen atmosphere and heated in an oil bath at 45° C. for 21 hours. After cooling to room temperature, the mixture was filtered through a pad of silica gel and the filtrate was evaporated under vacuum to afford crude 5-amino-2-butyl-4-chloro-6-fluoro-2-(3-oxobutyl)-1-indanone.

Step 8: 7-amino-9a-butyl-8-chloro-6-fluoro-1,2,9,9a-tetrahydro-3H-fluoren-3-one

The crude diketone from step 7 (approx. 10.6 mmol) was dissolved in toluene (106 mL) and treated with acetic acid (0.606 mL, 10.6 mmol) and pyrrolidine (0.883 mL, 10.6 mmol). The resulting solution was stirred and heated in an oil bath at 90° C. for 3.5 hours. After cooling to room temperature, the mixture was filtered through a pad of silica gel and the product washed off with EtOAc. The filtrate and washings were concentrated under vacuum. The residue was purified by flash chromatography on a Biotage 40M KP-Sil column, eluting with 4:1 hexanes-EtOAc. The product containing fractions were evaporated under vacuum to provide 7-amino-9a-butyl-8-chloro-6-fluoro-1,2,9,9a-tetrahydro-3H-fluoren-3-one (2.7 g, 83%) as a yellow solid.

Step 9: 7-amino-4-bromo-9a-butyl-8-chloro-6-fluoro-1,2,9, 9a-tetrahydro-3H-fluoren-3-one A solution of 7-amino-9a-butyl-8-chloro-6-fluoro-1,2,9, 9a-tetrahydro-3H-fluoren-3-one (1.36 g, 4.42 mmol) in anhydrous $CH_2Cl_2$ (13 mL) was cooled in an ice bath, placed under a nitrogen atmosphere, treated with N-bromosuccinimide (0.787 g, 4.42 mmol) and stirred at 0–5° C. for one hour. The reaction mixture was filtered through a pad of silica gel and the pad was washed with EtOAc. The filtrate and washings were evaporated under vacuum. The residue was purified by flash chromatography on a Biotage 40M column using 10:1 hexanes-EtOAc as eluting solvent. The product containing fractions were evaporated under vacuum to afford 7-amino-4-bromo-9a-butyl-8-chloro-6-fluoro-1,2, 9,9a-tetrahydro-3H-fluoren-3-one (1.08 g, 63%) as a yellow solid.

$^1$H NMR ($CDCl_3$, 500 MHz) δ 0.85 (t, $CH_2CH_2CH_2CH_3$), 1.13–1.29 (m, $CH_2CH_2CH_2CH_3$), 1.47 and 1.63 (two m, $CH_2CH_2CH_2CH_3$), 2.05 and 2.25 (two ddd, 1-$CH_2$), 2.69 and 3.04 (two d, 9-$CH_2$), 2.71 (m, 2-$CH_2$), 4.56 (br s, $NH_2$), and 8.19 (d, H-5); mass spectrum m/z 386.0 (M+1).

EXAMPLE 3

SYNTHESIS OF 7-AMINO-9a-BUTYL-4,8-DICHLORO-6-FLUORO-1,2,9,9a-TETRAHYDRO-3H-FLUOREN-3-ONE

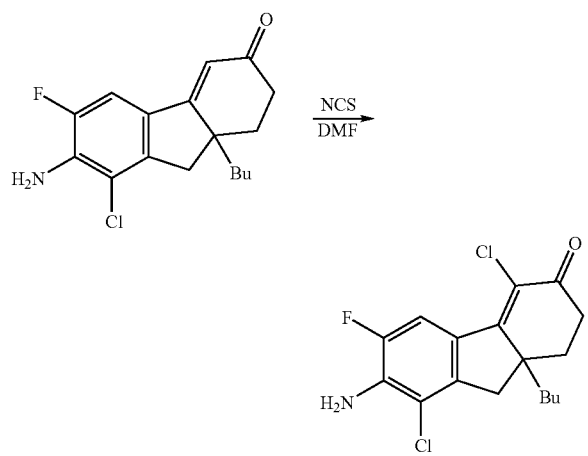

A solution of 7-amino-9a-butyl-8-chloro-6-fluoro-1,2,9, 9a-tetrahydro-3H-fluoren-3-one (0.054 g, 0.175 mmol) in anhydrous N,N-dimethylformamide (0.35 mL) was cooled in an ice bath, placed under a nitrogen atmosphere, and treated with N-chlorosuccinimide (0.024 g, 0.18 mmol). The mixture was stirred at room temperature for 18.5 hours and then heated in an oil bath at 35° C. for 3 hours. The reaction mixture was partitioned between EtOAc and water, and the organic phase was dried over $MgSO_4$, filtered, and evaporated under vacuum. The residue was purified by preparative HPLC on a YMC-Pak ODS column (2×10 cm), eluting with 0.1% TFA in 10–100% MeCN/$H_2O$ (15 min gradient) at a 20 mL/min flow rate. The product-containing fractions (UV detection at 350 nm) were diluted with EtOAc, washed with 5% $NaHCO_3$, water, and brine, dried over $MgSO_4$, filtered, and evaporated under vacuum. The residual film was triturated with hexanes and the solid residue was dried under a $N_2$ stream to afford 7-amino-9a-butyl-4,8-dichloro-6-fluoro-1,2,9,9a-tetrahydro-3H-fluoren-3-one (48 mg, 80%).

$^1$H NMR ($CDCl_3$, 500 MHz) δ 0.86 (t, $CH_2CH_2CH_2CH_3$), 1.13–1.30 (m, $CH_2CH_2CH_2CH_3$), 1.49 and 1.64 (two m, $CH_2CH_2CH_2CH_3$), 2.05 and 2.26 (two ddd, 1-$CH_2$), 2.63–2.74 (m, 2-$CH_2$), 2.70 and 3.05 (two d, 9-$CH_2$), 4.56 (br s, $NH_2$), and 7.97 (d, H-5); mass spectrum m/z 342.1 (M+1), 344.1 (M+3).

EXAMPLE 4

SYNTHESIS OF 7-AMINO-9a-BUTYL-8-CHLORO-6-FLUORO-4-IODO-1,2,9,9a-TETRAHYDRO-3H-FLUOREN-3-ONE

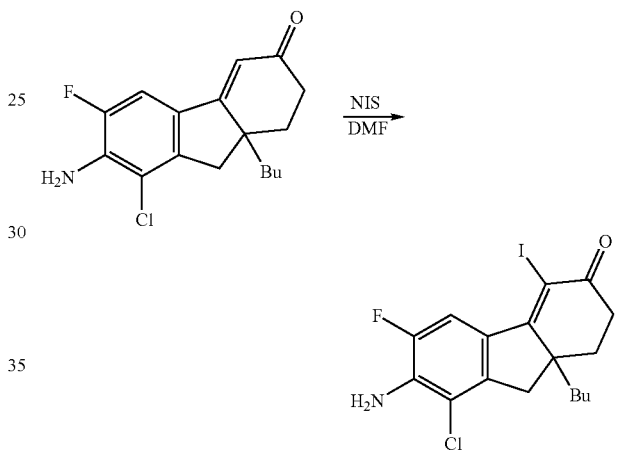

A solution of 7-amino-9a-butyl-8-chloro-6-fluoro-1,2,9, 9a-tetrahydro-3H-fluoren-3-one (0.053 g, 0.17 mmol) in anhydrous N,N-dimethylformamide (0.34 mL) was cooled in an ice bath, placed under a nitrogen atmosphere, and treated with N-iodosuccinimide (95% pure, 0.040 g, 0.18 mmol). The mixture was stirred for two hours with gradual warming to room temperature. The reaction mixture was partitioned between EtOAc and water, and the organic phase was dried over $MgSO_4$, filtered, and evaporated under vacuum. The residue was purified by preparative HPLC on a YMC-Pak ODS column (2×10 cm), eluting with 0.1% TFA in 10–100% MeCN/$H_2O$ (15 min gradient) at a 20 mL/min flow rate. The product-containing fractions (UV detection at 350 nm) were diluted with EtOAc, washed with 5% $NaHCO_3$, water, and brine, dried over $MgSO_4$, filtered, and evaporated under vacuum. The residual film was triturated with hexanes and the solid residue was dried under a $N_2$ stream to afford 7-amino-9a-butyl-8-chloro-6-fluoro4-iodo-1,2,9,9a-tetrahydro-3H-fluoren-3-one (53 mg, 73%).

$^1$H NMR ($CDCl_3$, 500 MHz) δ 0.85 (t, $CH_2CH_2CH_2CH_3$), 1.12–1.30 (m, $CH_2CH_2CH_2CH_3$), 1.45 and 1.61 (two m, $CH_2CH_2CH_2CH_3$), 2.04 and 2.24 (two ddd, 1-$CH_2$), 2.68 and 3.00 (two d, 9-$CH_2$), 2.73 and 2.79 (two ddd, 2-$CH_2$), and 8.47 (d, H-5); mass spectrum m/z 434.0 (M+1).

EXAMPLE 5

SYNTHESIS OF 7-AMINO-9a-BUTYL-8-CHLORO-6-FLUORO-4-(2-FURYL)-1,2,9,9a-TETRAHYDRO-3H-FLUOREN-3-ONE

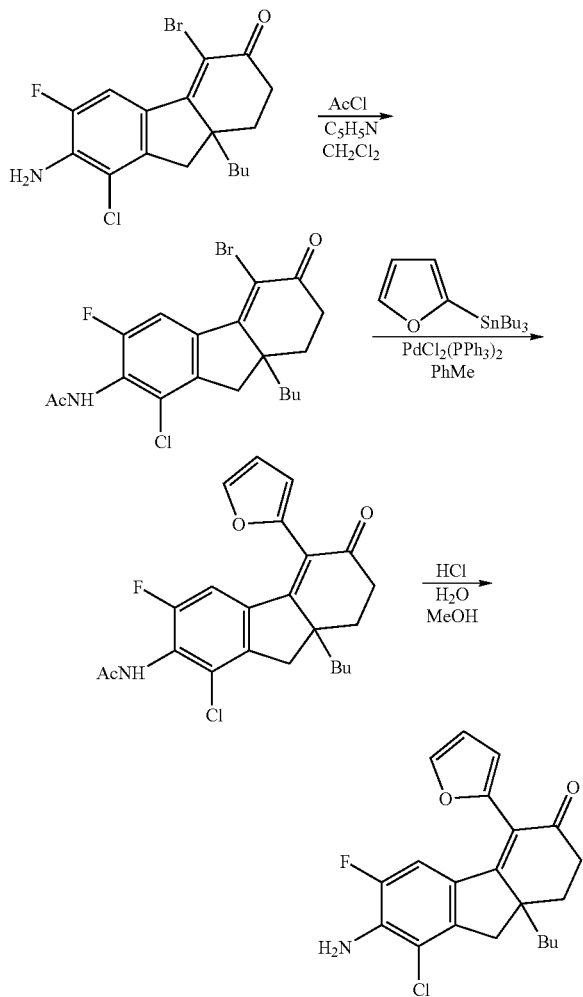

Step 1: 7-(acetylamino)-4-bromo-9a-butyl-8-chloro-6-fluoro-1,2,9,9a-tetrahydro-3H-fluoren-3-one A partial solution of 7-amino-4-bromo-9a-butyl-8-chloro-6-fluoro-1,2,9,9a-tetrahydro-3H-fluoren-3-one (0.940 g, 2.44 mmol) in CH$_2$Cl$_2$ (7.5 mL) was cooled in an ice bath and treated successively with pyridine (0.202 mL, 2.5 mmol) and acetyl chloride (0.178 mL, 2.5 mmol). The reaction mixture was placed under a N$_2$ atmosphere and stirred at room temperature. Additional pyridine (0.01 mL, 0.12 mmol and 0.039 mL, 0.48 mmol) was added after 4 and 5 hours, respectively; and additional acetyl chloride (0.009 mL, 0.12 mmol; 0.035 mL, 0.49 mmol; and 0.175 mL, 2.45 mmol) was added after 4, 5, and 5.5 hours, respectively. After stirring overnight at room temperature, the mixture was treated with EtOH (10 mL) and 5N NaOH (ca. 1 mL), stirred briefly, and then partitioned between EtOAc and water. The organic phase was washed with brine, dried over MgSO$_4$, filtered, and evaporated under vacuum to provide 7-(acetylamino)-4-bromo-9a-butyl-8-chloro-6-fluoro-1,2,9,9a-tetrahydro-3H-fluoren-3-one (1.02 g, 98%) as an orange solid.

Step 2: 7-(acetylamino)-9a-butyl-8-chloro-6-fluoro-4-(2-furyl)-1,2,9,9a-tetrahydro-3H-fluoren-3-one Tributyl(2-furyl)stannane (0.47 mL, 1.7 mmol) was added to a mixture of 7-(acetylamino)-4-bromo-9a-butyl-8-chloro-6-fluoro-1,2,9,9a-tetrahydro-3H-fluoren-3-one (0.367 g, 0.86 mmol) and dichlorobis(triphenylphosphine)palladium (II) (0.121 g, 0.17 mmol) in anhydrous toluene (8.6 mL). The mixture was purged with N$_2$, then stirred and heated in an oil bath at 100° C. for 2 hours. After cooling to room temperature, the mixture was added to a pad of silica gel and the product eluted with EtOAc (20 mL). The solvent was evaporated and the residue (0.93 g) was purified by Biotage flash chromatography on a 40S silica gel column (4×7 cm) using 2:1 hexane-EtOAc as eluting solvent. The product containing fractions were concentrated under vacuum to provide crude 7-(acetylamino)-9a-butyl-8-chloro-6-fluoro4-(2-furyl)-1,2,9,9a-tetrahydro-3H-fluoren-3-one (0.362 g) as an orange foam.

Step 3: 7-amino-9a-butyl-8-chloro-6-fluoro-4-(2-furyl)-1,2,9,9a-tetrahydro-3H-fluoren-3-one The crude product from step 2 (0.36 g, ~0.86 mmol) was dissolved in methanol (4 mL) and the solution was diluted with 6N HCl (4 mL). The mixture was stirred and heated at 80° C. for one hour. After cooling to room temperature, the mixture was partitioned between EtOAc (100 mL) anad water (100 mL). The organic phase was washed with water and brine, dried over MgSO$_4$, filtered, and evaporated under vacuum to give an orange oil (330 mg). The crude product was purified by Biotage flash chromatography on a 40S (4×7 cm) silica gel column, eluting with 2:1 hexane-EtOAc, to afford 7-amino-9a-butyl-8-chloro-6-fluoro-4-(2-furyl)-1,2,9,9a-tetrahydro-3H-fluoren-3-one (237 mg, 74%) as an orange foam.

$^1$H NMR (CDCl$_3$, 500 MHz) δ 0.88 (t, CH$_2$CH$_2$CH$_2$CH$_3$), 1.20–1.33 (m, CH$_2$CH$_2$CH$_2$CH$_3$), 1.52 and 1.72 (two m, CH$_2$CH$_2$CH$_2$CH$_3$), 2.09 and 2.31 (two ddd, 1-CH$_2$), 2.58 and 2.66 (two ddd, 2-CH$_2$), 2.71 and 3.06 (two d, 9-CH$_2$), 4.46 (s, NH$_2$), 6.09 (d, H-5), 6.38 (d, furyl H-3), 6.54 (dd, furyl H-4), and 7.52 (d, furyl H-5); mass spectrum m/z 374.1 (M+1).

EXAMPLE 6

SYNTHESIS OF 7-AMINO-4,8-DIBROMO-9a-BUTYL-6-FLUORO-1,2,9,9a-TETRAHYDRO-3H-FLUOREN-3-ONE

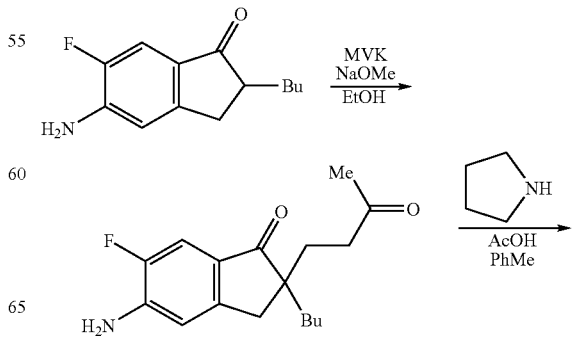

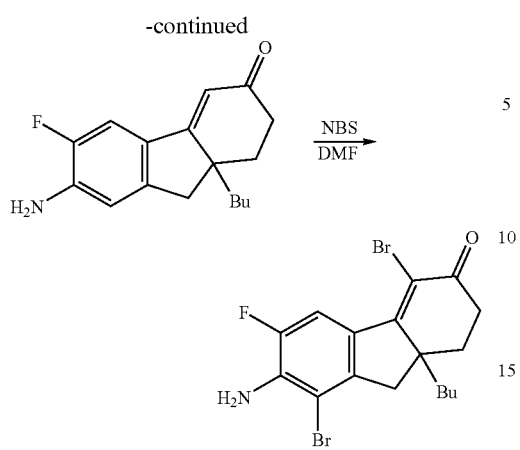

Step 1: 5-amino-2-butyl-6-fluoro-2-(3-oxobutyl)-1-indanone

A solution of 5-amino-2-butyl-6-fluoro-1-indanone (0.98 g, 4.64 mmol) in ethanol (17 mL) was treated with sodium methoxide (0.5M solution in MeOH, 1.86 mL, 0.928 mmol) and methyl vinyl ketone (0.579 mL, 6.97 mmol). The resulting solution was stirred at room temperature and under a nitrogen atmosphere for 2 days. The mixture was diluted with $CH_2Cl_2$ and filtered through a pad of silica gel. The product washed off with EtOAc and the filtrate was evaporated under vacuum. The residue was purified by flash chromatography on a Biotage 40M KP-Sil column, eluting with 3:1 to 2.5:1 hexanes-EtOAc. The product containing fractions were evaporated under vacuum to provide to afford 5-amino-2-butyl-6-fluoro-2-(3-oxobutyl)-1-indanone(0.6 g, 46%) as a yellow foam.

Step 2: 7-amino-9a-butyl-6-fluoro-1.2,9,9a-tetrahydro-3H-fluoren-3-one

The diketone from step 1 (0.6 g, 2.14 mmol) was dissolved in toluene (15 mL) and treated with acetic acid (0.236 mL, 4.12 mmol) and pyrrolidine (0.344 mL, 4.12 mmol). The resulting solution was stirred and heated in an oil bath at 100° C. for 1.5 hours. After cooling to room temperature, the mixture was filtered through a pad of silica gel and the product was washed off with EtOAc. The filtrate and washings were concentrated under vacuum. The residue was purified by flash chromatography on a Biotage 40M KP-Sil column, eluting with 4:1 to 3:1 hexanes-EtOAc. The product containing fractions were evaporated under vacuum to provide 7-amino-9a-butyl-6-fluoro-1,2,9,9a-tetrahydro-3H-fluoren-3-one (0.45 g, 80%) as a yellow solid.

Step 3: 7-amino4,8-dibromo-9a-butyl-6-fluoro-1,2,9,9a-tetrahydro-3H-fluoren-3-one A solution of 7-amino-9a-butyl-6-fluoro-1,2,9,9a-tetrahydro-3H-fluoren-3-one (0.021 g, 0.077 mmol) in anhydrous N,N-dimethylformamide (0.5 mL) was cooled in an ice bath, placed under a nitrogen atmosphere, treated with N-bromosuccinimide (0.0151 g, 0.085 mmol) and stirred at room temperature for 30 minutes. The reaction mixture was poured into a water solution of 10% $K_2CO_3$ and extracted with EtOAc. The organic extracts were washed with water and evaporated under vacuum. The crude product was purified by preparative layer chromatography on a 0.05× 20×20 cm silica gel GF plate, developing with 30% EtOAc in hexanes, to afford 7-amino-4,8-dibromo-9a-butyl-6-fluoro-1,2,9,9a-tetrahydro-3H-fluoren-3-one (0.017 g, 51%) as a yellow solid.

$^1$H NMR ($CDCl_3$, 500 MHz) δ 0.85 (t, $CH_2CH_2CH_2CH_3$), 1.13–1.29 (m, $CH_2CH_2CH_2CH_3$), 1.49 and 1.63 (two m, $CH_2CH_2CH_2CH_3$), 2.05 and 2.25 (two ddd, 1-$CH_2$), 2.68 and 3.00 (two d, 9-$CH_2$), 2.72 (m, 2-$CH_2$), 4.65 (br s, $NH_2$), and 8.22 (d, H-5).

EXAMPLE 7

SYNTHESIS OF 7-AMINO-9a-BUTYL-6-FLUORO-4-METHYL-1,2,9,9a-TETRAHYDRO-3H-FLUOREN-3-ONE

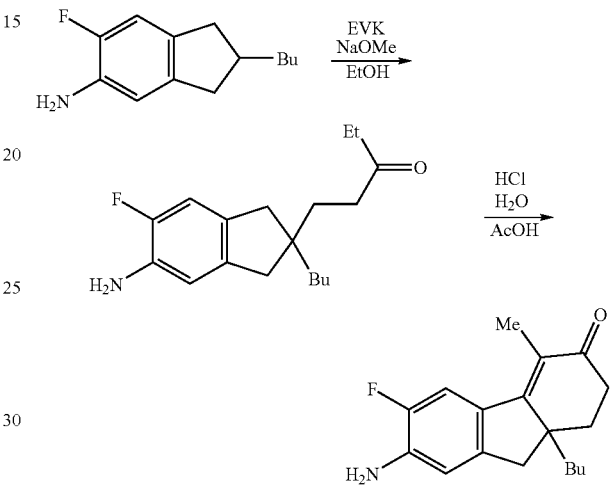

Step 1: 5-amino-2-butyl-6-fluoro-2-(3-oxopentyl)-1-indanone

A solution of 5-amino-2-butyl-6-fluoro-1-indanone (0.81 g, 3.84 mmol) in ethanol (18 mL) was treated with sodium methoxide (0.5M solution in MeOH, 1.54 mL, 0.768 mmol) and ethyl vinyl ketone (0.572 mL, 5.76 mmol). The resulting solution was stirred under a nitrogen atmosphere and heated in an oil bath at 70° C. over night. After cooling to room temperature, the mixture was diluted with $CH_2Cl_2$ and filtered through a pad of silica gel. The product washed off with EtOAc and the filtrate was evaporated under vacuum. The residue was purified by flash chromatography on a Biotage 40M KP-Sil column, eluting with 4:1 to 3:1 hexanes-EtOAc. The product containing fractions were evaporated under vacuum to provide to afford 5-amino-2-butyl-6-fluoro-2-(3-oxopentyl)-1-indanone(0.51 g, 45%) as a yellow foam.

Step 2: 7-amino-9a-butyl-6-fluoro-4-methyl-1,2,9,9a-tetrahydro-3H-fluoren-3-one

The diketone from step 1 (0.51 g, 1.73 mmol) was treated with acetic acid (5 mL,) and aqueous 6N HCl (5 mL). The resulting solution was stirred and heated in an oil bath at 100° C. for 1.5 hours. After cooling to room temperature, the mixture was poured into a slurry of solid $NaHCO_3$ in $CH_2Cl_2$, then filtered through a pad of silica gel and the product was washed off with EtOAc. The filtrate and washings were concentrated under vacuum. The residue was purified by flash chromatography on a Biotage 40M KP-Sil column, eluting with 4:1 to 3:1 hexanes-EtOAc. The product containing fractions were evaporated under vacuum to provide 7-amino-9a-butyl-6-fluoro-4-methyl-1,2,9,9a-tetrahydro-3H-fluoren-3-one (0.40 g, 83%) as a yellow solid $^1$H NMR (CDCl$_3$, 500 MHz) δ 0.83 (t, CH$_2$CH$_2$CH$_2$CH$_3$), 1.11–1.28 (m, CH$_2$CH$_2$CH$_2$CH$_3$), 1.36 and 1.55 (two m, CH$_2$CH$_2$CH$_2$CH$_3$), 1.94 and 2.18 (two ddd, 1-CH$_2$), 2.03 (s, 4-CH$_3$), 2.44 and 2.55 (two ddd, 2-CH$_2$), 2.60 and 2.85 (two d, 9-CH$_2$), 6.69 (d, H-8), and 7.34 (d, H-5); mass spectrum m/z 288.2 (M+1).

EXAMPLE 8

SYNTHESIS OF 7-AMINO-8-BROMO-9a-BUTYL-6-FLUORO-4-METHYL-1,2,9,9a-TETRAHYDRO-3H-FLUOREN-3-ONE

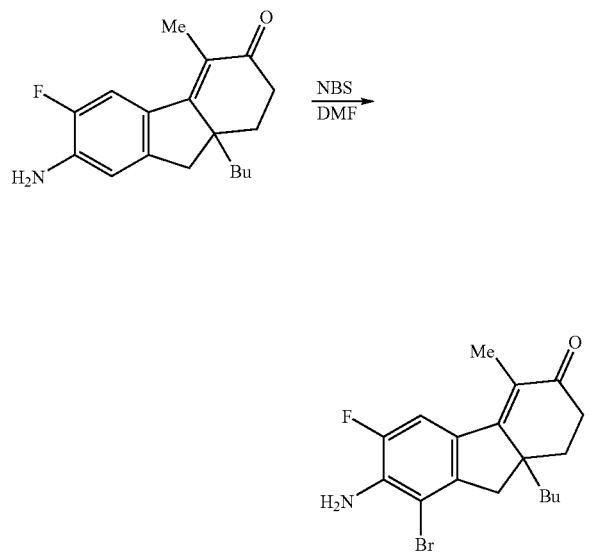

A solution of 7-amino-9a-butyl-6-fluoro4-methyl-1,2,9,9a-tetrahydro-3H-fluoren-3-one (0.138 g, 0.481 mmol) in anhydrous N,N-dimethylformamide (4.8 mL) was cooled in an ice bath, placed under a nitrogen atmosphere, treated with N-bromosuccinimide (0.94 g, 0.53 mmol), and stirred at room temperature for 30 minutes. The reaction mixture was poured into a water solution of 10% K$_2$CO$_3$ and extracted with EtOAc. The organic layer was washed with water and evaporated under vacuum. The crude product was purified by preparative layer chromatography on a 0.05×20×20 cm silica gel GF plate, developing with 20% EtOAc in hexanes, to afford 7-amino-8-bromo-9a-butyl-6-fluoro-4-methyl-1,2,9,9a-tetrahydro-3H-fluoren-3-one (0.089 g, 50%) as a yellow solid.

$^1$H NMR (CDCl$_3$, 500 MHz) δ 0.85 (t, CH$_2$CH$_2$CH$_2$CH$_3$), 1.13–1.28 (m, CH$_2$CH$_2$CH$_2$CH$_3$), 1.39 and 1.57 (two m, CH$_2$CH$_2$CH$_2$CH$_3$), 1.97 and 2.23 (two ddd, 1-CH$_2$), 2.03 (s, 4-CH$_3$), 2.46 and 2.56 (two ddd, 2-CH$_2$), 2.62 and 2.96 (two d, 9-CH$_2$), 4.45 (br s, NH$_2$), and 7.34 (d, H-5).

EXAMPLE 9

SYNTHESIS OF 7-AMINO-9a-BUTYL-6-FLUORO-4-METHYL-8-NITRO-1,2,9,9a-TETRAHYDRO-3H-FLUOREN-3-ONE

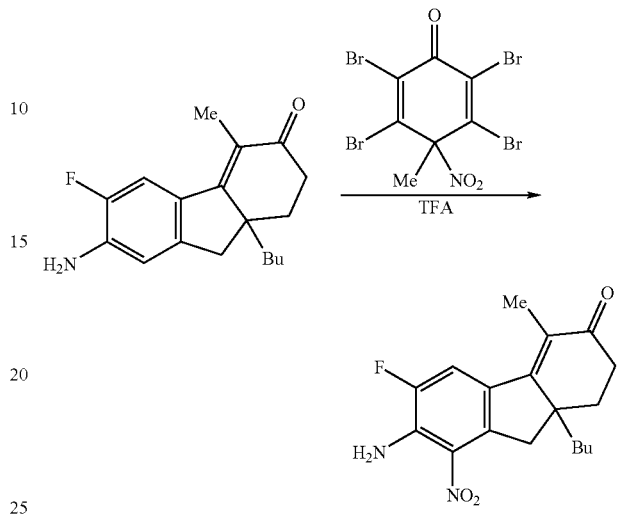

A solution of 7-amino-9a-butyl-6-fluoro-4-methyl-1,2,9,9a-tetrahydro-3H-fluoren-3-one (243 mg, 0.845 mmol) in trifluoroacetic acid (1.7 mL) was treated with 2,3,5,6-tetrabromo-4-methyl-4-nitro-2,5-cyclohexadien-1-one (396 mg, 0.845 mmol). The resulting mixture was placed under a N$_2$ atmosphere, sonicated briefly, and stirred at room temperature for 3 hours. The mixture was diluted with EtOAc (50 mL), washed successively with water, 5% NaHCO$_3$ and brine, dried over MgSO$_4$, filtered, and evaporated under vacuum to a brown oil (659 mg). The crude product was purified by flash chromatography on a Biotage 40S KP-Sil column, eluting with 10:1 hexanes-EtOAc. The product containing fractions were evaporated under vacuum to an orange gum (113 mg, 40%) which was lyophilized from benzene to provide 7-amino-9a-butyl-6-fluoro-4-methyl-8-nitro-1,2,9,9a-tetrahydro-3H-fluoren-3-one as an amorphous solid.

$^1$H NMR (CDCl$_3$, 500 MHz) δ 0.84 (t, CH$_2$CH$_2$CH$_2$CH$_3$), 1.11–1.29 (m, CH$_2$CH$_2$CH$_2$CH$_3$), 1.36 and 1.56 (two m, CH$_2$CH$_2$CH$_2$CH$_3$), 1.98 and 2.27 (two ddd, 1-CH$_2$), 2.04 (s, 4-CH$_3$), 2.49 and 2.57 (two ddd, 2-CH$_2$), 3.08 and 3.45 (two d, 9-CH$_2$), 6.32 (br s, NH$_2$), and 7.62 (d, H-5); mass spectrum m/z 333.2 (M+1).

EXAMPLE 10

SYNTHESIS OF 7,8-DIAMINO-9a-BUTYL-6-FLUORO-4-METHYL-1,2,9,9a-TETRAHYDRO-3H-FLUOREN-3-ONE

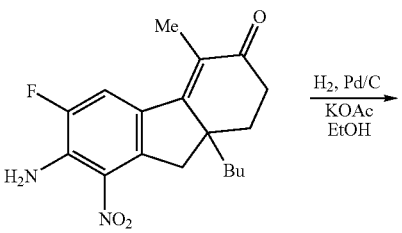

-continued

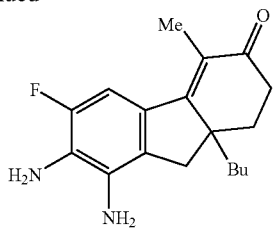

A sample of 7-amino-9a-butyl-6-fluoro-4-methyl-8-nitro-1,2,9,9a-tetrahydro-3H-fluoren-3-one (106 mg, 0.32 mmol) was dissolved in ethanol (13 mL) with slight warming. After cooling to room temperature, the solution was treated with KOAc (31 mg, 32 mmol) and 10% palladium on carbon (31 mg), and the resulting mixture was stirred under an atmosphere of hydrogen for 3.25 hours. The mixture was filtered through a pad of silica gel, washing the product off with 5% MeOH in CH$_2$Cl$_2$. The filtrate and washings were evaporated under vacuum. The residue was purified by preparative layer chromatography on a 0.1×20×20 cm silica gel GF plate, developing with 1:1 hexanes-EtOAc. The major UV visible band was eluted with 5% MeOH in CH$_2$Cl$_2$, the eluant was concentrated under vacuum, and the residue was lyophilized from benzene to afford 7,8-diamino-9a-butyl-6-fluoro-4-methyl-1,2,9,9a-tetrahydro-3H-fluoren-3-one (70 mg, 72%) as an amorphous solid.

$^1$H NMR (CDCl$_3$, 500 MHz) δ 0.84 (t, CH$_2$CH$_2$CH$_2$CH$_3$), 1.13–1.28 (m, CH$_2$CH$_2$CH$_2$CH$_3$), 1.39 and 1.58 (two m, CH$_2$CH$_2$CH$_2$CH$_3$), 1.98 and 2.24 (two ddd, 1-CH$_2$), 2.04 (br s, 4-CH$_3$), 2.46 and 2.56 (two ddd, 2-CH$_2$), 2.50 and 2.83 (two br d, 9-CH$_2$), and 7.03 (br d, H-5); mass spectrum m/z 627.2 (2M+Na).

EXAMPLE 11

SYNTHESIS OF 7-AMINO-9a-BUTYL-6-FLUORO-4-NITRO-1,2,9,9a-TETRAHYDRO-3H-FLUOREN-3-ONE

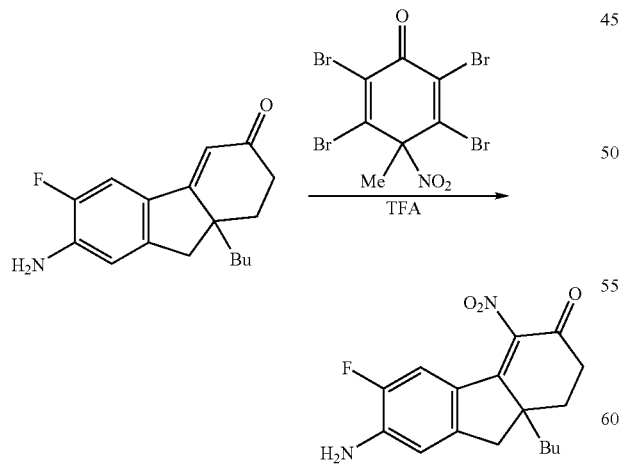

A solution of 7-amino-9a-butyl-6-fluoro-1,2,9,9a-tetrahydro-3H-fluoren-3-one (34.6 mg, 0.126 mmol) in trifluoroacetic acid (0.25 mL) was treated with 2,3,5,6-tetrabromo-4-methyl-4-nitro-2,5-cyclohexadien-1-one (59 mg, 0.126 mmol). The resulting mixture was placed under a N$_2$ atmosphere, sonicated briefly, and stirred at room temperature for one hour. The mixture was diluted with EtOAc (15 mL), washed successively with water, 5% NaHCO$_3$ and brine, dried over MgSO$_4$, filtered, and evaporated under vacuum to a brown oil (86 mg). The crude product was purified by preparative layer chromatography on a 0.1×20×20 cm silica gel GF plate, developing with 2:1 hexanes-EtOAc. The major UV visible band was eluted with 5% MeOH in CH$_2$Cl$_2$, the eluant was concentrated under vacuum to an orange oil (16 mg, 40%), and the oil was lyophilized from benzene to afford 7-amino-9a-butyl-6-fluoro-4-nitro-1,2,9,9a-tetrahydro-3H-fluoren-3-one as an amorphous solid.

$^1$H NMR (CDCl$_3$, 500 MHz) δ 0.87 (t, CH$_2$CH$_2$CH$_2$CH$_3$), 1.15–1.34 (m, CH$_2$CH$_2$CH$_2$CH$_3$), 1.53 and 1.72 (two m, CH$_2$CH$_2$CH$_2$CH$_3$), 2.07 and 2.26 (two ddd, 1-CH$_2$), 2.64 (m, 2-CH$_2$), 2.72 and 2.97 (two d, 9-CH$_2$), 4.45 (br s, NH$_2$), 6.67 (d, H-8), and 7.12 (d, H-5); mass spectrum m/z 319.1 (M+1).

EXAMPLE 12

SYNTHESIS OF 7-AMINO-4-BROMO-9a-BUTYL-6-FLUORO-1,2,9,9a-TETRAHYDRO-3H-FLUOREN-3-ONE

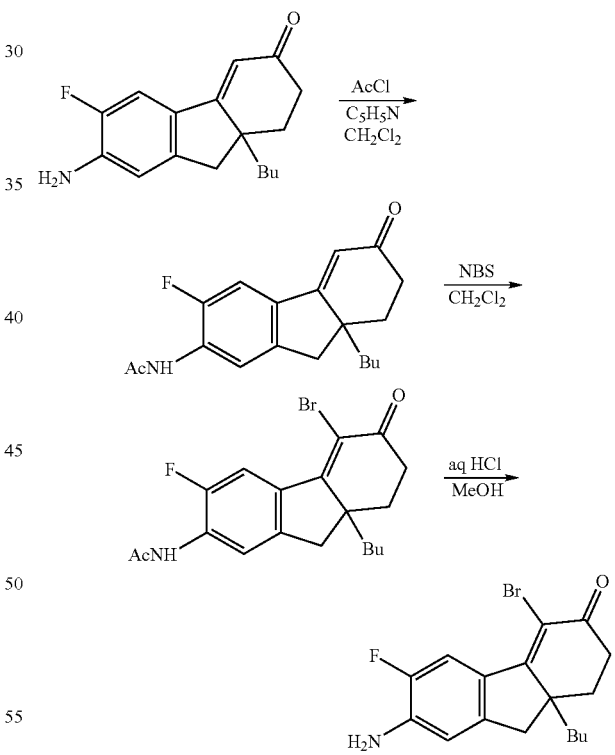

Step 1: 7-(acetylamino)-9a-butyl-6-fluoro-1,2,9,9a-tetrahydro-3H-fluoren-3-one

A solution of 7-amino-9a-butyl-6-fluoro-1,2,9,9a-tetrahydro-3H-fluoren-3-one (1.12 g, 4.1 mmol) in anhydrous CH$_2$Cl$_2$ (13.7 mL) was purged with N$_2$, cooled in an ice bath, and treated with pyridine (0.33 mL, 4.1 mmol) followed by acetyl chloride (0.65 mL, 9 mmol). After stirring at 0–5° C. for 4.5 hours, the reaction mixture was partitioned between water and EtOAc. The organic portion was washed with brine, dried over MgSO₄, filtered, and concentrated under vacuum to provide 7-(acetylamino)-9a-butyl-6-fluoro-1,2,9,9a-tetrahydro-3H-fluoren-3-one (1.1 g) as an orange foam. This material was used without further purification.

Step 2: 7-(acetylamino)-4-bromo-9a-butyl-6-fluoro-1,2,9,9a-tetrahydro-3H-fluoren-3-one The product from step 1 (1.1 g, approx. 3.5 mmol) was dissolved in anhydrous $CH_2Cl_2$ (11 mL) and the solution was purged with $N_2$, cooled in an ice bath, and treated with N-bromosuccinimide (0.498 g, 2.8 mmol). After stirring at 0–5° C. for one hour, the reaction mixture was partitioned between water (150 mL) and EtOAc (150 mL). The organic portion was washed with aqueous 5% NaHCO₃ and brine, dried over MgSO₄, filtered, and evaporated under vacuum to provide crude 7-(acetylamino)-4-bromo-9a-butyl-6-fluoro-1,2,9,9a-tetrahydro-3H-fluoren-3-one (1.35 g).

Step 3: 7-amino-4-bromo-9a-butyl-6-fluoro-1,2,9,9a-tetrahydro-3H-fluoren-3-one

A solution of 7-(acetylamino)-4-bromo-9a-butyl-6-fluoro-1,2,9,9a-tetrahydro-3H-fluoren-3-one (33 mg, 0.1 mmol) in methanol (0.5 mL) was diluted with aqueous 6N HCl (0.5 mL). The resulting mixture was stirred in a capped flask and heated in an oil bath at 80° C. for 40 minutes. After cooling, the mixture was partitioned between water and EtOAc. The organic solution was washed with aqueous 5% NaHCO₃, water, and brine, dried over MgSO₄, filtered, and concentrated under vacuum to an oil. The oil ws purified by preparative layer chromatography on a 0.1×20×20 cm silica gel GF plate, developing with 2:1 hexanes-EtOAc. The major UV visible band was eluted with 5% MeOH in $CH_2Cl_2$, the eluant was evaporated under vacuum, and the residue was lyophilized from benzene to provide 7-amino-4-bromo-9a-butyl-6-fluoro-1,2,9,9a-tetrahydro-3H-fluoren-3-one (17 mg, 47%) as an amorphous solid.

$^1$H NMR (CDCl₃, 500 MHz) δ 0.84 (t, $CH_2CH_2CH_2CH_3$), 1.12–1.29 (m, $CH_2CH_2CH_2CH_3$), 1.47 and 1.63 (two m, $CH_2CH_2CH_2CH_3$), 2.04 and 2.21 (two ddd, 1-$CH_2$), 2.68 and 2.91 (two d, 9-$CH_2$), 2.71 (m, 2-$CH_2$), 6.67 (d, H-8), and 8.22 (d, H-5); mass spectrum m/z 352.1 (M+1).

EXAMPLE 13

SYNTHESIS OF 4-ACETYL-7-AMINO-8-BROMO-9a-BUTYL-6-FLUORO-1,2,9,9a-TETRAHYDRO-3H-FLUOREN-3-ONE

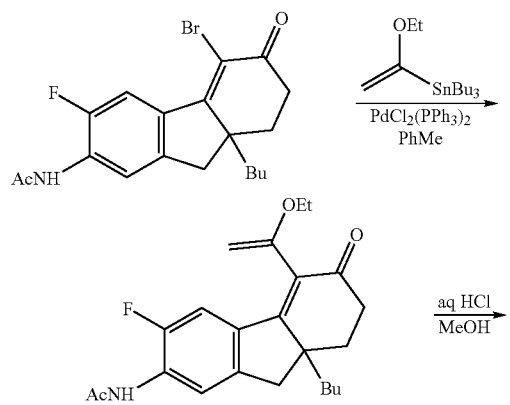

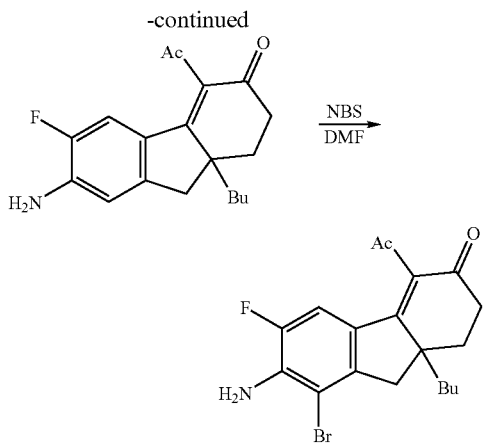

Step 1: 7-(acetylamino)-9a-butyl-4-(1-ethoxyvinyl)-6-fluoro-1,2,9,9a-tetrahydro-3H-fluoren-3-one A partial solution of 7-(acetylamino)-4-bromo-9a-butyl-6-fluoro-1,2,9,9a-tetrahydro-3H-fluoren-3-one (495 mg, 1.26 mmol) in anhydrous toluene (6.3 mL) was purged with $N_2$, treated with dichlorobis(triphenylphosphine)palladium (II) (177 mg, 0.25 mmol), purged with $N_2$, and treated with tributyl(1-ethoxyvinyl)tin (0.600 mL, 1.9 mmol). The resulting mixture was stirred under a $N_2$ atmosphere and heated in an oil bath at 100° C. for two hours. After cooling to room temperature, the mixture was filtered through a pad of silica gel, washing the product off with EtOAc. The filtrate and washings were evaporated under vacuum to an oil. The crude product was purified by flash chromatography on a Biotage 40S KP-Sil column, eluting with 4:1 hexanes-EtOAc (1 L) followed by 2:1 hexanes-EtOAc (1 L). The product containing fractions were concentrated under vacuum to afford 7-(acetylamino)-9a-butyl-4-(1-ethoxyvinyl)-6-fluoro-1,2,9,9a-tetrahydro-3H-fluoren-3-one (238 mg, 49%) as a yellow foam.

Step 2: 4-acetyl-7-amino-9a-butyl-6-fluoro-1,2,9,9a-tetrahydro-3H-fluoren-3-one

A solution of 7-(acetylamino)-9a-butyl-4-(1-ethoxyvinyl)-6-fluoro-1,2,9,9a-tetrahydro-3H-fluoren-3-one (205 mg, 0.53 mmol) in methanol (7.5 mL) was treated with aqueous 6N HCl (7.5 mL). The resulting mixture was placed under a $N_2$ atmosphere and stirred with heating in an oil bath at 80° C. for 50 minutes. After cooling to room temperature, the mixture was partitioned between EtOAc and aqueous 5% NaHCO₃. The organic solution was washed with water and brine, dried over MgSO₄, filtered, and evaporated under vacuum to afford 4-acetyl-7-amino-9a-butyl-6-fluoro-1,2,9,9a-tetrahydro-3H-fluoren-3-one (157 mg, 93%) as a foam.

Step 3: 4-acetyl-7-amino-8-bromo-9a-butyl-6-fluoro-1,2,9,9a-tetrahydro-3H-fluoren-3-one A solution of 4-acetyl-7-amino-9a-butyl-6-fluoro-1,2,9,9a-tetrahydro-3H-fluoren-3-one (157 mg, 0.5 mmol) in anhydrous N,N-dimethylformamide (1.5 mL) was purged with $N_2$, cooled in an ice bath, and treated with N-bromosuccinimide (89 mg, 0.5 mmol). The resulting solution was stirred at 0–5° C. for one hour, and then partitioned between EtOAc and water. The aqueous portion was extracted with more EtOAc. The combined organics were washed with water and brine, dried over MgSO₄, filtered, and concentrated under vacuum. The oily residue was purified by flash chromatography on a Biotage 12M column, eluting with 4:1 hexanes-EtOAc. The product containing fractions were evaporated under vacuum to afford 4-acetyl-7-amino-8-bromo-9a-butyl-6-fluoro-1,2,9,9a-tetrahydro-3H-fluoren-3-one (147 mg, 75%) as a yellow oil.

$^1$H NMR (CDCl$_3$, 500 MHz) δ 0.86 (t, CH$_2$CH$_2$CH$_2$CH$_3$), 1.17–1.31 (m, CH$_2$CH$_2$CH$_2$CH$_3$), 1.45 and 1.64 (two m, CH$_2$CH$_2$CH$_2$CH$_3$), 2.02 and 2.27 (two ddd, 1-CH$_2$), 2.38 (s, COCH$_3$), 2.46–2.60 (m, 2-CH$_2$), 2.64 and 2.99 (two d, 9-CH$_2$), 4.61 (s, NH$_2$), and 7.20 (d, H-5).

EXAMPLE 14

SYNTHESIS of 7-AMINO-4-BROMO-9a-BUTYL-6,8-DIFLUORO-1,2,9,9a-TETRAHYDRO-3H-FLUOREN-3-ONE

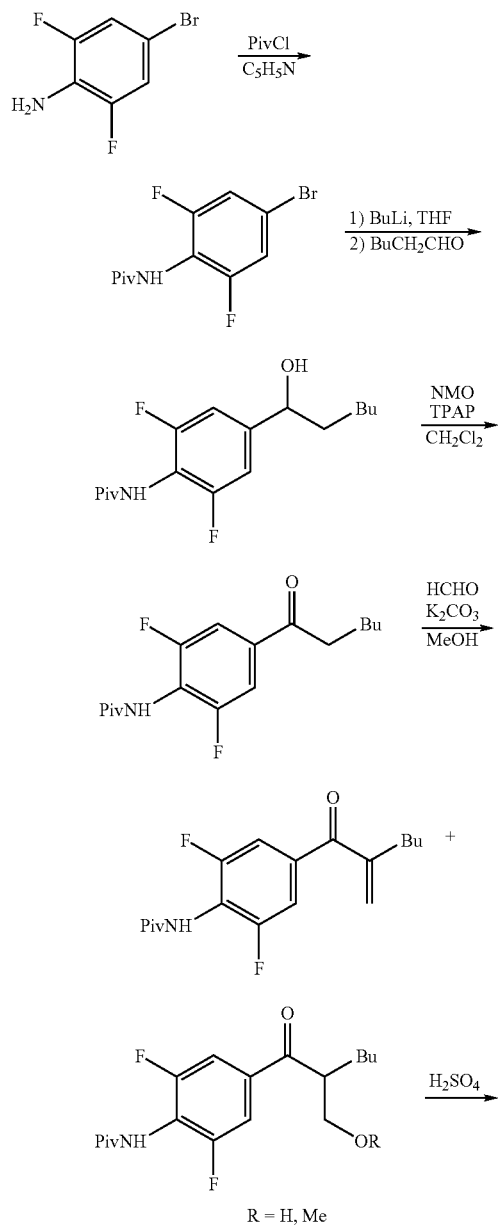

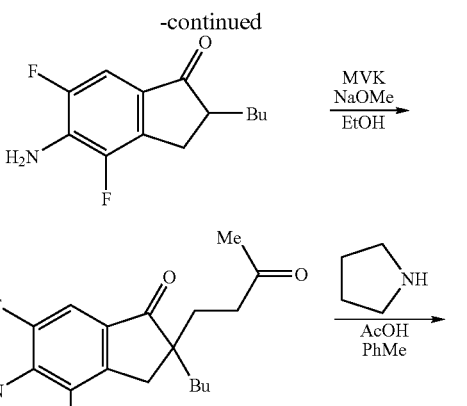

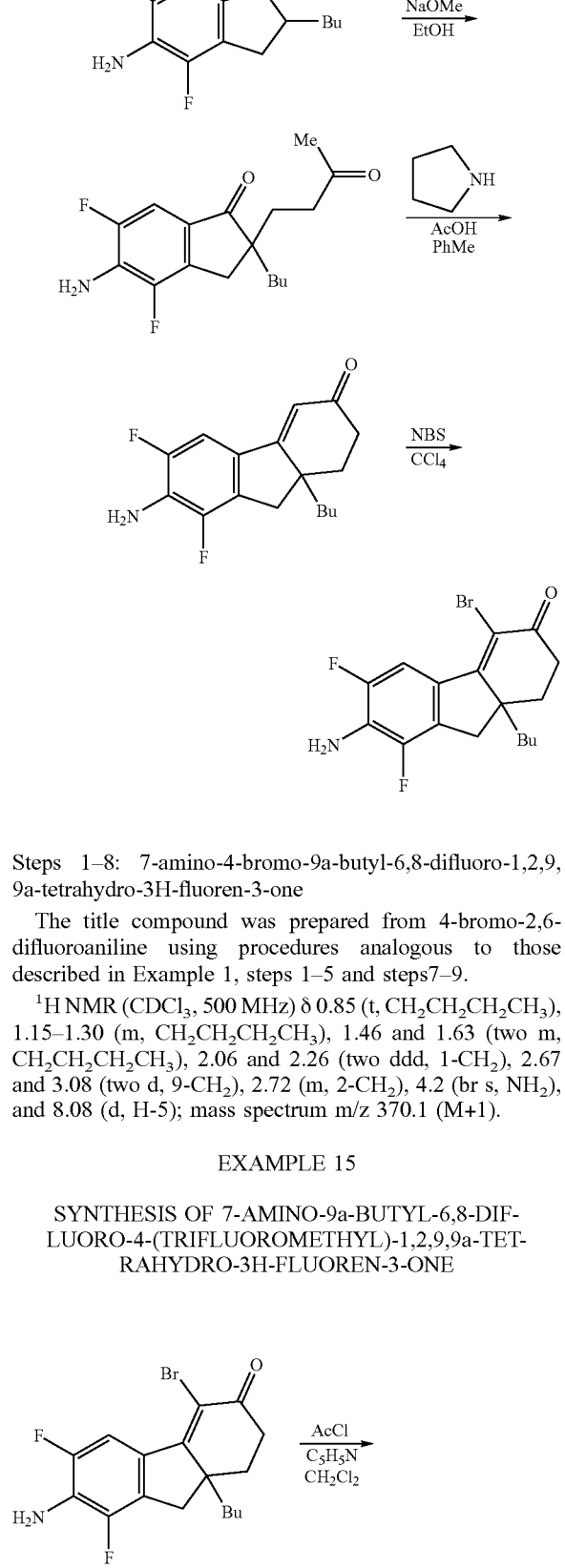

Steps 1–8: 7-amino-4-bromo-9a-butyl-6,8-difluoro-1,2,9,9a-tetrahydro-3H-fluoren-3-one The title compound was prepared from 4-bromo-2,6-difluoroaniline using procedures analogous to those described in Example 1, steps 1–5 and steps 7–9.

$^1$H NMR (CDCl$_3$, 500 MHz) δ 0.85 (t, CH$_2$CH$_2$CH$_2$CH$_3$), 1.15–1.30 (m, CH$_2$CH$_2$CH$_2$CH$_3$), 1.46 and 1.63 (two m, CH$_2$CH$_2$CH$_2$CH$_3$), 2.06 and 2.26 (two ddd, 1-CH$_2$), 2.67 and 3.08 (two d, 9-CH$_2$), 2.72 (m, 2-CH$_2$), 4.2 (br s, NH$_2$), and 8.08 (d, H-5); mass spectrum m/z 370.1 (M+1).

EXAMPLE 15

SYNTHESIS OF 7-AMINO-9a-BUTYL-6,8-DIFLUORO-4-(TRIFLUOROMETHYL)-1,2,9,9a-TETRAHYDRO-3H-FLUOREN-3-ONE

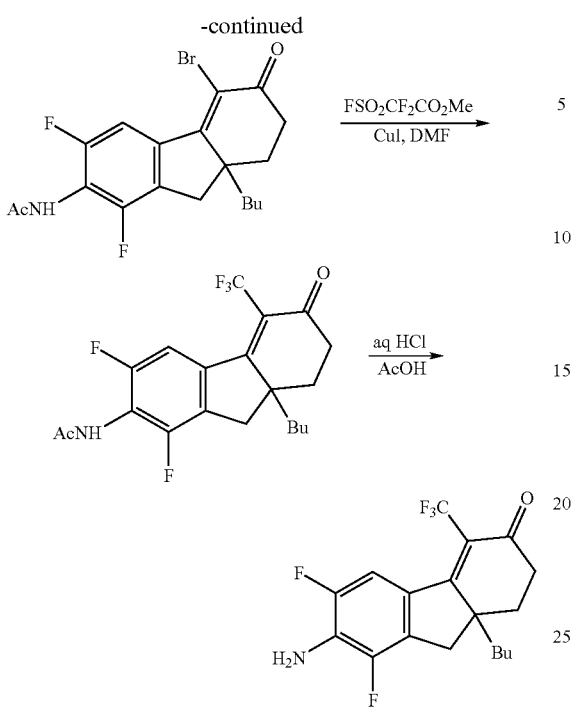

Step 1: 7-(acetylamino)-4-bromo-9a-butyl-6,8-difluoro-1,2,9,9a-tetrahydro-3H-fluoren-3-one A solution of 7-amino-4-bromo-9a-butyl-6,8-difluoro-1,2,9,9a-tetrahydro-3H-fluoren-3-one(0.131 g, 0.354 mmol) in CH$_2$Cl$_2$ (3 mL) was treated with AcCl (0.051 mL, 0.708 mmol) and pyridine (0.043 mL, 0.531 mmol). The resulting solution was stirred under a nitrogen atmosphere for 5 hours. This mixture was treated with NaOH (5N, 1 mL) and EtOH (6 mL), and stirred for 10 minutes. After being diluted with CH$_2$Cl$_2$, the mixture was dried over MgSO$_4$, filtered through a pad of silica gel and rinsed with EtOAc. The filtrate was evaporated under vacuum. The crude product was purified by preparative layer chromatography on a 0.05×20×20 cm silica gel GF plate, developing with 50% EtOAc in hexanes, to afford 7-(acetylamino)-4-bromo-9a-butyl-6,8-difluoro-1,2,9,9a-tetrahydro-3H-fluoren-3-one (0.131 g, 90%) as yellow foam.

Step 2: 7-(acetylamino)-9a-butyl-6,8-difluoro-4-(trifluoromethyl)-1,2,9,9a-tetrahydro-3H-fluoren-3-one A solution of 7-(acetylamino)-4-bromo-9a-butyl-6,8-difluoro-1,2,9,9a-tetrahydro-3H-fluoren-3-one (0.131 g, 0.318 mmol) in N,N-dimethylformamide (3 mL) was treated with CuI (0.072 g, 0.382 mmol) and FSO$_2$CF$_2$CO$_2$Me (0.602 mL, 4.77 mmol). The resulting solution was stirred and heated in an oil bath at 70° C. over night. After cooling to room temperature, the mixture was diluted with CH$_2$Cl$_2$, filtered through a pad of silica gel and the product washed off with EtOAc. The filtrate and washings were concentrated under vacuum to give the crude product of 7-(acetylamino)-9a-butyl-6,8-difluoro-4-(trifluoromethyl)-1,2,9,9a-tetrahydro-3H-fluoren-3-one Step 3: 7-amino-9a-butyl-6,8-difluoro-4-(trifluoromethyl)-1,2,9,9a-tetrahydro-3H-fluoren-3-one The crude 7-(acetylamino)-9a-butyl-6,8-difluoro-4-(trifluoromethyl)-1,2,9,9a-tetrahydro-3H-fluoren-3-one from step 2 (about 0.318 mmol) was treated with acetic acid (2 mL) and 6N HCl (2 mL). The resulting solution was stirred and heated in an oil bath at 100° C. for 2 hours. After cooling to room temperature, the mixture was poured into a slurry of solid Na$_2$CO$_3$ in CH$_2$Cl$_2$, dried over MgSO$_4$, then filtered through a pad of silica gel and the product washed off with EtOAc. The filtrate and washings were concentrated under vacuum. The crude product was purified by preparative layer chromatography on a 0.05×20×20 cm silica gel GF plate, developing with 25% EtOAc in hexanes, to afford 7-amino-9a-butyl-6,8-difluoro-4-(trifluoromethyl)-1,2,9,9a-tetrahydro-3H-fluoren-3-one (0.026 g, 23%) as a yellow solid.

$^1$H NMR (CDCl$_3$, 500 MHz) δ 0.84 (t, CH$_2$CH$_2$CH$_2$CH$_3$), 1.12–1.30 (m, CH$_2$CH$_2$CH$_2$CH$_3$), 1.30 and 1.52 (two m, CH$_2$CH$_2$CH$_2$CH$_3$), 2.03 and 2.22 (two ddd, 1-CH$_2$),2.55 (m, 2-CH$_2$),2.68 and 3.07 (two d, 9-CH$_2$), 4.29 (s, NH$_2$), and 7.36 (d, H-5); mass spectrum m/z 360.1 (M+1).

EXAMPLE 16

SYNTHESIS OF 7-AMINO-9a-BUTYL-4-ETHYL-6,8-DIFLUORO-1,2,9,9a-TETRAHYDRO-3H-FLUOREN-3-ONE

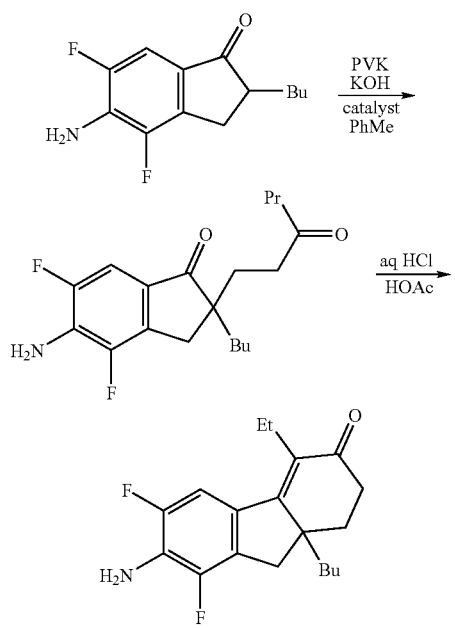

Step 1: 5-amino-2-butyl4,6-difluoro-2-(3-oxohexyl)-1-indanone

A solution of 5-amino-2-butyl-4,6-difluoro-1-indanone (0.25 g, 1.05 mmol) in toluene (5.5 mL) was treated with potassium hydroxide (0.1 g, 40% w/w), N-[4-(trifluoromethyl)benzyl]cinchoninium bromide (0.112 g, 0.21 mmol), and propyl vinyl ketone (0.154 g, 1.57 mmol). The resulting solution was stirred under a nitrogen atmosphere for 2 hours. After being diluted with CH$_2$Cl$_2$, the mixture was filtered through a pad of silica gel and rinsed with EtOAc. The filtrate was evaporated under vacuum to afford crude 5-amino-2-butyl-4,6-difluoro-2-(3-oxohexyl)-1-indanone.

Step 2: 7-amino-9a-butyl-4-ethyl-6,8-difluoro-1,2,9,9a-tetrahydro-3H-fluoren-3-one The crude diketone from step 1 (about 1.05 mmol) was treated with acetic acid (5 mL) and 6N HCl (5 mL). The resulting solution was stirred and heated in an oil bath at 100° C. for 1.5 hours. After cooling to room temperature, the mixture was poured into a slurry of solid Na$_2$CO$_3$ in CH$_2$Cl$_2$, dried over MgSO$_4$, then filtered through a pad of silica gel and the product washed off with EtOAc. The filtrate and washings were concentrated under vacuum. The crude product was purified by preparative layer chromatography on a 0.05×20×20 cm silica gel GF plate, developing with 30% EtOAc in hexanes, to afford 7-amino-9a-butyl-4-ethyl-6,8-difluoro-1,2,9,9a-tetrahydro-3H-fluoren-3-one (0.16 g, 48%) as a yellow solid.

$^1$H NMR (CDCl$_3$, 500 MHz) δ 0.85 (t, CH$_2$CH$_2$CH$_2$CH$_3$), 1.08 (t, CH$_2$CH$_3$), 1.14–1.29 (m, CH$_2$CH$_2$CH$_2$CH$_3$), 1.37 and 1.55 (two m, CH$_2$CH$_2$CH$_2$CH$_3$), 1.95 and 2.22 (two ddd, 1-CH$_2$), 2.38–2.67 (m, CH$_2$CH$_3$ and 2-CH$_2$), 2.57 and 3.02 (two d, 9-CH$_2$), 3.9 (br s, NH$_2$), and 7.17 (d, H-5); mass spectrum m/z 320.2 (M+1).

EXAMPLE 17

SYNTHESIS OF 7-AMINO-4-BROMO-9a-BUTYL-6-FLUORO-8-METHYL-1,2,9,9a-TETRAHYDRO-3H-FLUOREN-3-ONE

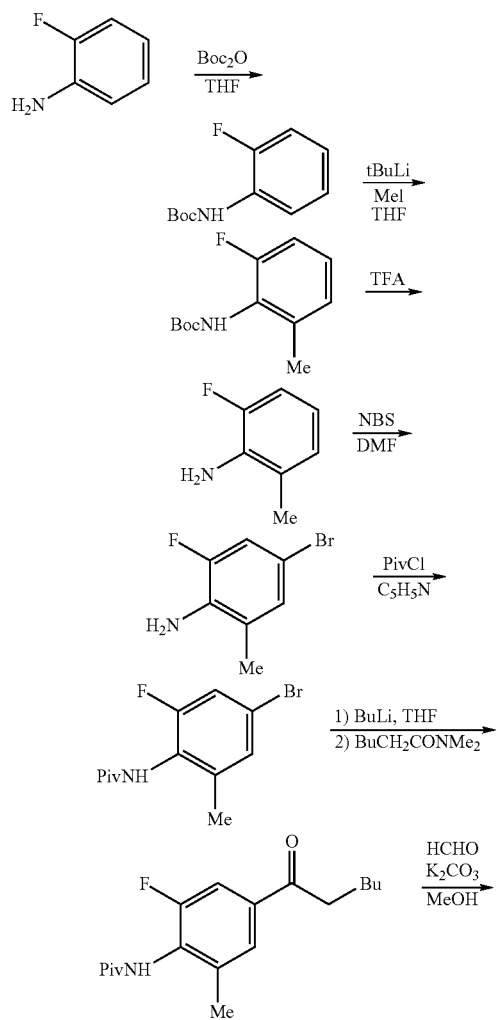

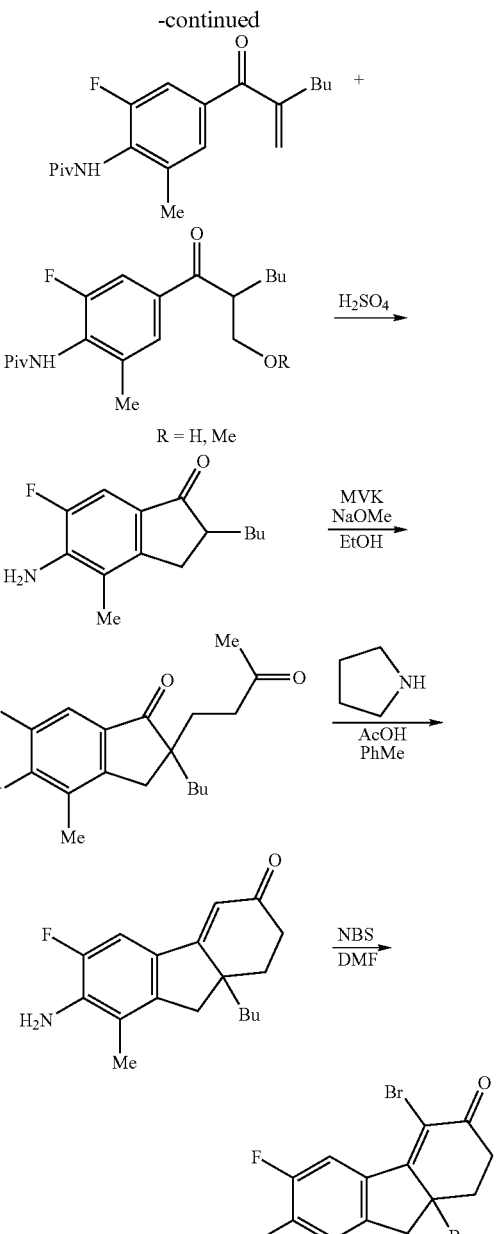

Step 1: tert-butyl 2-fluorophenylcarbamate

A solution of 2-fluoroaniline (53 g, 477 mmol) in tetrahydrofuran (500 mL) was treated with di-tert-butyl dicarbonate (104 g, 477 mmol). The resulting solution was stirred under a nitrogen atmosphere and heated in an oil bath at 60° C. for 3 days. After cooling to room temperature, the reaction mixture was partitioned between EtOAc and 1M citric acid. The organic portion was washed with 1M citric acid, dried over MgSO$_4$, filtered through a pad of silica, and evaporated under vacuum. The crude product was desolved in hexane and the solid by-product was filtered off and rinsed with a mixture of hexane and CH$_2$Cl$_2$. The filtrate was evaporated under vacuum to give tert-butyl 2-fluorophenylcarbamate (99.5 g, 98%) as a yellow solid.

Step 2: tert-butyl 2-fluoro-6-methylphenylcarbamate

A solution of tert-butyl 2-fluorophenylcarbamate (99.5 g, 471 mmol) in anhydrous tetrahydrofuran (900 mL) was placed under a nitrogen atmosphere, cooled in a dry ice-acetone bath, and stirred while t-butyllithium (666 mL of a 1.7M solution in pentane, 1132 mmol) was added slowly. The resulting mixture was slowly warmed up to −15° C. in 2 hours, then cooled back to −78° C. and treated with iodomethane (32.3 mL, 518 mmol). After warming up to −15° C. in 30 minutes, the mixture was removed from the cooling bath and treated with aqueous saturated $NH_4Cl$ (20 mL). The resulting slurry was diluted with $CH_2Cl_2$ (2000 mL), dried over $MgSO_4$, filtered through a pad of silica, and concentrated under vacuum to afford tert-butyl 2-fluoro-6-methylphenylcarbamate(105 g, 99.5%) as a yellow solid.

Step 3: 2-fluoro-6-methylaniline

The crude carbamate from step 2 (7.2 g, 32 mmol) was treated with trifluoroacetic acid (30 mL). The resulting solution was stirred at room temperature for 30 minutes, then most of trifluoroacetic acid was evaporated under vacuum. The residue was diluted with $CH_2Cl_2$ and poured into a slurry of solid $Na_2CO_3$ in $CH_2Cl_2$. The resulting slurry was carefully treated with EtOAc to increase product solubility, then filtered through a pad of silica gel and the product washed off with EtOAc. The filtrate and washings were concentrated under vacuum to afford 2-fluoro-6-methylaniline as a yellow solid.

Step 4: 4-bromo-2-fluoro-6-methylaniline

A solution of crude 2-fluoro-6-methylaniline from step 3 (about 32 mmol) in anhydrous N,N-dimethylformamide (100 mL) was cooled in an ice bath, placed under a nitrogen atmosphere, treated with N-bromosuccinimide (5.7 g, 32 mmol), and then stirred at room temperature for 10 minutes. The reaction mixture was poured into a water solution of diluted brine and extracted with EtOAc. The organic extracts were washed with diluted brine three times, dried over $MgSO_4$, filtered through a pad of silica, and concentrated under vacuum to afford 4-bromo-2-fluoro-6-methylaniline as a yellow foam.

Step 5: N-(4-bromo-2-fluoro-6-methylphenyl)-2,2-dimethylpropanamide

Pivaloyl chloride (4 mL, 38.4 mmol) was added slowly (caution—exothermic reaction) to an ice cold solution of the crude 4-bromo-2-fluoro-6-methylaniline from step 4 (about 32 mmol) in pyridine (20 mL). After the addition, the ice bath was removed and the warm reaction mixture was stirred at room temperature for 30 minutes. The reaction mixture was poured into a water solution of 1 N HCl and extracted with EtOAc. The organic layer was washed with 1N HCl three times, dried over $MgSO_4$, filtered, and concentrated under vacuum. The residue was purified by flash chromatography on a Biotage 40M KP-Sil column, eluting with 9:1 hexanes-EtOAc. The product containing fractions were evaporated under vacuum to provide N-(4-bromo-2-fluoro-6-methylphenyl)-2,2-dimethylpropanamide (4.3 g, 49% for 3 steps) as a yellow solid.

Step 6: N-(2-fluoro-4-hexanoyl-6-methylphenyl)-2,2-dimethylpropanamide

A solution of N-(4-bromo-2-fluoro-6-methylphenyl)-2,2-dimethylpropanamide (21.7 g, 79.2 mmol) in anhydrous tetrahydrofuran (500 mL) was placed under a nitrogen atmosphere, cooled in a dry ice-acetone bath, and stirred while butyllithium (124 mL of a 1.6M solution in hexanes, 198 mmol) was added dropwise. The resulting mixture was aged at −78° C. for 30 minutes and then treated with N,N-dimethylhexanamide (28.3 g, 198 mmol). After warming up to 0° C. over 2 hours, the mixture was removed from the cooling bath and treated with aqueous saturated $NH_4Cl$ (20 mL). The resulting slurry was diluted with $CH_2Cl_2$ (1000 mL), dried over $MgSO_4$, filtered through a pad of silica, and concentrated under vacuum. The residue was purified by flash chromatography on a Biotage 40M KP-Sil column, eluting with 19:1 to 9:1 hexanes-EtOAc. The product containing fractions were evaporated under vacuum to provide N-(2-fluoro-4-hexanoyl-6-methylphenyl)-2,2-dimethylpropanamide (12.7 g, 55%) as a yellow foam.

Steps 7–11: 7-amino-4-bromo-9a-butyl-6-fluoro-8-methyl-1,2,9,9a-tetrahydro-3H-fluoren-3-one The title compound was prepared from N-(2-fluoro-4-hexanoyl-6-methylphenyl)-2,2-dimethylpropanamide using procedures analogous to those described in Example 2, steps 4, 5, 7, 8, and 9.

$^1$H NMR (CDCl$_3$, 500 MHz) δ 0.84 (t, CH$_2$CH$_2$CH$_2$CH$_3$), 1.14–1.28 (m, CH$_2$CH$_2$CH$_2$CH$_3$), 1.46 and 1.64 (two m, CH$_2$CH$_2$CH$_2$CH$_3$), 2.03 and 2.24 (two ddd, 1-CH$_2$), 2.12 (s, 8-CH$_3$), 2.62 and 2.94 (two d, 9-CH$_2$), 2.65–2.78 (m, 2-CH$_2$), and 8.15 (d, H-5).

EXAMPLE 18

SYNTHESIS OF 7-AMINO-8-CYANO-9a-ETHYL-4-METHYL-1,2,9,9a-TETRAHYDRO-3H-FLUOREN-3-ONE

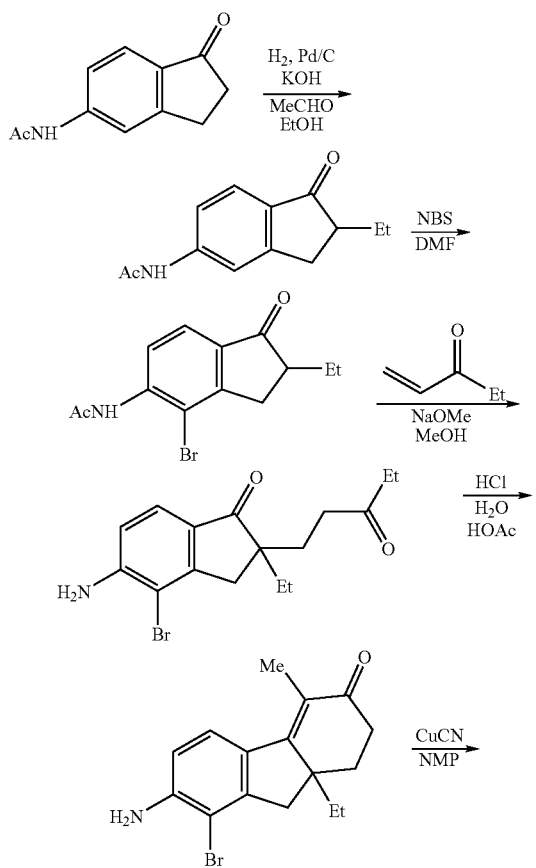

-continued

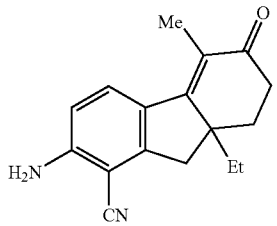

Step 1: 5-(acetylamino)-2-ethyl-1-indanone

A mixture of 5-(acetylamino)-1-indanone (3.0 g, 15.7 mmol), KOH (85%, 0.22 g, 3.33 mmol), and EtOH (62 mL) was treated with 10% Pd/C (0.10 g), placed under a $H_2$ atmosphere (balloon), and treated with acetaldehyde (1.8 mL, 31.9 mmol). The resulting mixture was stirred at room temperature for 18.5 hours, then filtered and the filtrate evaporated under vacuum. The residue was partitioned between EtOAc (100 mL) and water (100 mL). The organic phase was washed with brine, dried over $MgSO_4$, filtered, and evaporated under vacuum to give a foam (3.58 g). The crude product was purified by chromatography on EM silica gel 60 (2.75×25 cm column), eluting with 20% EtOAc in $CH_2Cl_2$ (500 mL) followed by 33% EtOAc in $CH_2Cl_2$ (300 mL). The product-containing fractions were evaporated under vacuum to provide 5-(acetylamino)-2-ethyl-1-indanone (2.32 g) as a foam.

Step 2: 5-(acetylamino)4-bromo-2-ethyl-1-indanone

A solution of 5-(acetylamino)-2-ethyl-1-indanone (2.32 g, 10.7 mmol) in anhydrous N,N-dimethylformamide (10.7 mL) was treated with N-bromosuccinimide (2.00 g, 11.21 mmol). The mixture was placed under a $N_2$ atmosphere, stirred, and heated in an oil bath at 60° C. for 100 minutes. After cooling to room temperature, the mixture was partitioned between EtOAc (200 mL) and water (200 mL). The organic phase was washed with water (4×200 mL) and brine (100 mL), dried over $MgSO_4$, filtered, and evaporated under vacuum to afford crude 5-(acetylamino)-4-bromo-2-ethyl-1-indanone as a yellow solid (2.95 g).

Step 3: 5-amino-4-bromo-2-ethyl-2-(3-oxopentyl)-1-indanone

A solution of 5-(acetylamino)-4-bromo-2-ethyl-1-indanone (1.0 g, 3.39 mmol) in MeOH (5.1 mL) was treated with 0.5M NaOMe in MeOH (3.4 mL, 1.7 mmol) and ethyl vinyl ketone (0.506 mL, 5.08 mmol). The mixture was stirred and heated at 60° C. for 4.5 hours, then evaporated under vacuum. The residue was partitioned between EtOAc (75 mL), brine (50 mL), and water (10 mL). The organic portion was dried over $MgSO_4$, filtered, and evaporated under vacuum. The residue was added to a short column of silica gel (30 mL) which was washed with $CH_2Cl_2$ (150 mL) and eluted with EtOAc (150 mL). The EtOAc eluant was evaporated under vacuum to provide crude 5-amino-4-bromo-2-ethyl-2-(3-oxopentyl)-1-indanone (1.17 g) as an oil.

Step 4: 7-amino-8-bromo-9a-ethyl-4-methyl-1,2,9,9a-tetrahydro-3H-fluoren-3-one

The crude diketone (1.17 g) from step 3 was dissolved in acetic acid (14 mL) and the solution was diluted with aqueous 6N HCl (14 mL). The resulting mixture was stirred and heated in an oil bath at 80° C. for 5 hours and then kept at room temperature for 3 days. The mixture was diluted with EtOAc (100 mL) and carefully basified with aqueous $K_2CO_3$ (200 mL). The organic portion was washed with brine, dried over $MgSO_4$ filtered, and evaporated under vacuum. The residue was lyophilized from benzene to afford crude 7-amino-8-bromo-9a-ethyl-4-methyl-1,2,9,9a-tetrahydro-3H-fluoren-3-one (1.0 g) as an amorphous solid.

Step 5: 7-amino-8-cyano-9a-ethyl-4-methyl-1,2,9,9a-tetrahydro-3H-fluoren-3-one

A mixture of crude 7-amino-8-bromo-9a-ethyl-4-methyl-1,2,9,9a-tetrahydro-3H-fluoren-3-one (0.97 g, 3.02 mmol), CuCN (0.318 g, 3.55 mmol), and 1-methyl-2-pyrrolidinone (NMP, 6 mL) was placed under a $N_2$ atmosphere, stirred, and heated in an oil bath at 160–170° C. for 5.5 hours. After cooling to room temperature, the mixture was added to EtOAc (200 mL) and water (200 mL) and filtered through a pad of solka-floc. The organic portion of the filtrate was washed with water (5×200 mL) and brine (100 mL), dried over $MgSO_4$, filtered, and evaporated under vacuum to a red oil (0.8 g). The crude product was purified by chromatography on EM silica gel 60 (2.75×25 cm column), eluting with 5% EtOAc in $CH_2Cl_2$, to afford 7-amino-8-cyano-9a-ethyl-4-methyl-1,2,9,9a-tetrahydro-3H-fluoren-3-one (0.48 g) as a solid.

$^1$H NMR (CDCl$_3$, 500 MHz) δ 0.87 (t, CH$_2$CH$_3$), 1.46 and 1.62 (two dq, CH$_2$CH$_3$), 1.97 and 2.25 (two ddd, 1-CH$_2$), 2.03 (s, 4-CH$_3$), 2.46 and 2.55 (two ddd, 2-CH$_2$), 2.74 and 3.08 (two d, 9-CH$_2$), 4.73 (s, NH$_2$), 6.67 (d, H-6), and 7.67 (d, H-5).

EXAMPLES 19–63

The following compounds were prepared using methods analogous to those described in the preceding examples:

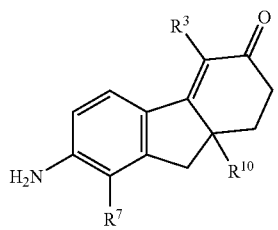

19  $R^3$ = Br        7-amino-4-bromo-9a-butyl-1,2,9,9a-tetrahydro-
    $R^7$ = H         3H-fluoren-3-one
    $R^{10}$ = CH$_2$CH$_2$CH$_2$CH$_3$ $^1$H NMR(DMSO-d$_6$, 500 MHz) δ 0.79(t, CH$_2$CH$_2$CH$_2$CH$_3$), 1.04–1.27(m, CH$_2$CH$_2$CH$_2$CH$_3$), 1.32 and 1.57(two m, CH$_2$CH$_2$CH$_2$CH$_3$), 1.96 and 2.09(two m, -continued 1-CH$_2$), 2.48 and 2.65(two m, 2-CH$_2$), 2.64 and 2.85(two d, 9-CH$_2$), 6.14(s, NH$_2$), 6.51(s, H-8), 6.55(dd, H-6), and 8.13(d, H-5).

20    R$^3$ = Br          7-amino-4-bromo-8-methyl-9a-propyl-1,2,9,9a-
      R$^7$ = CH$_3$       tetrahydro-3H-fluoren-3-one
      R$^{10}$ = CH$_2$CH$_2$CH$_3$ $^1$H NMR(CDCl$_3$, 500 MHz) δ 0.84(t, CH$_2$CH$_2$CH$_3$), 1.24(m, CH$_2$CH$_2$CH$_3$), 1.50 and 1.61(two dt, CH$_2$CH$_2$CH$_3$), 2.05 and 2.23(two ddd, 1-CH$_2$), 2.09(s, 8-CH$_3$), 2.65 and 2.97(two d, 9-CH$_2$), 2.68 and 2.75(two ddd, 2-CH$_2$), 6.68(d, H-6), and 8.30(d, H-5).

21    R$^3$ = Br          7-amino-4-bromo-9a-butyl-8-methyl-1,2,9,9a-
      R$^7$ = CH$_3$       tetrahydro-3H-fluoren-3-one
      R$^{10}$ = CH$_2$CH$_2$CH$_2$CH$_3$ $^1$H NMR(CDCl$_3$, 500 MHz) δ 0.84(t, CH$_2$CH$_2$CH$_2$CH$_3$), 1.17–1.29(m, CH$_2$CH$_2$CH$_2$CH$_3$), 1.46 and 1.65(two m, CH$_2$CH$_2$CH$_2$CH$_3$), 2.04 and 2.24(two ddd, 1-CH$_2$), 2.08(s, 8-CH$_3$), 2.64 and 2.97(two d, 9-CH$_2$), 2.67 and 2.73(two m, 2-CH$_2$), 4.09(br s, NH$_2$), 6.68(d, H-6), and 8.30(d, H-5).

22    R$^3$ = CF$_3$        7-amino-9a-butyl-8-methyl-4-trifluoromethyl-
      R$^7$ = CH$_3$       1,2,9,9a-tetrahydro-3H-fluoren-3-one
      R$^{10}$ = CH$_2$CH$_2$CH$_2$CH$_3$ $^1$H NMR(CDCl$_3$, 500 MHz) δ 0.83(t, CH$_2$CH$_2$CH$_2$CH$_3$), 1.17–1.28(m, CH$_2$CH$_2$CH$_2$CH$_3$), 1.30 and 1.54(two m, CH$_2$CH$_2$CH$_2$CH$_3$), 2.01 and 2.20(two ddd, 1-CH$_2$), 2.09(s, 8-CH$_3$), 2.53(m, 2-CH$_2$), 2.66 and 2.95(two d, 9-CH$_2$), 4.14 (br s, NH$_2$), 6.62(d, H-6), and 7.56(m, H-5).

23    R$^3$ = CH$_3$        7-amino-8-bromo-9a-ethyl-4-methyl-1,2,9,9a-
      R$^7$ = Br          tetrahydro-3H-fluoren-3-one
      R$^{10}$ = CH$_2$CH$_2$CH$_3$ $^1$H NMR(CDCl$_3$, 500 MHz) δ 0.86(t, CH$_2$CH$_3$), 1.50 and 1.63(two dq, CH$_2$CH$_3$), 1.98 and 2.24(two ddd, 1-CH$_2$), 2.05(s, 4-CH$_3$), 2.46 and 2.56(two ddd, 2-CH$_2$), 2.61 and 2.99(two d, 9-CH$_2$), 4.42(s, NH$_2$), 6.70(d, H-6), and 7.48(d, H-5).

24    R$^3$ = Br          7-amino-4,8-dibromo-9a-ethyl-1,2,9,9a-
      R$^7$ = Br          tetrahydro-3H-fluoren-3-one
      R$^{10}$ = CH$_2$CH$_3$ $^1$H NMR(CDCl$_3$, 500 MHz) δ 0.87(t, CH$_2$CH$_3$), 1.59 and 1.69(two dq, CH$_2$CH$_3$), 2.06 and 2.26(two ddd, 1-CH$_2$), 2.64–2.76(m, 2-CH$_2$), 2.68 and 3.02(two d, 9-CH$_2$), 4.52(br s, NH$_2$), 6.74(d, H-6), and 8.33(d, H-5).

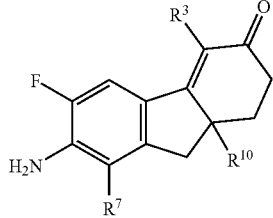

25    R$^3$ = CH$_2$CH$_3$     7-amino-4,9a-diethyl-6-fluoro-1,2,9,9a-
      R$^7$ = H           tetrahydro-3H-fluoren-3-one
      R$^{10}$ = CH$_2$CH$_3$ $^1$H NMR(CDCl$_3$, 500 MHz) δ 0.81(t, 9a-CH$_2$CH$_3$), 1.06(t, 4-CH$_2$CH$_3$), 1.45 and 1.57(two dq, 9a-CH$_2$CH$_3$), 1.91 and 2.16(two ddd, 1-CH$_2$), 2.40 and 2.61(two dq, 4-CH$_2$CH$_3$), 2.41 and 2.51(two ddd, 2-CH$_2$), 2.55 and 2.82(two d, 9-CH$_2$), 4.28(br s, NH$_2$), 6.66(d, H-8), and 7.27(d, H-5).

26    R$^3$ = Br          7-amino-4-bromo-9a-ethyl-6-fluoro-1,2,9,9a-
      R$^7$ = H           tetrahydro-3H-fluoren-3-one
      R$^{10}$ = CH$_2$CH$_3$ $^1$H NMR(CDCl$_3$, 500 MHz) δ 0.87(t, CH$_2$CH$_3$), 1.57 and 1.68(two dq, CH$_2$CH$_3$), 2.04 and 2.22(two ddd, 1-CH$_2$), 2.67 and 2.91(two d, 9-CH$_2$), 2.71(m, 2-CH$_2$), 6.67 (d, H-8), and 8.22(d, H-5); mass spectrum m/z 387.1(M+Na+MeCN).

27    R$^3$ = CH$_2$CH$_3$     7-amino-9a-butyl-4-ethyl-6-fluoro-1,2,9,9a-
      R$^7$ = H           tetrahydro-3H-fluoren-3-one
      R$^{10}$ = CH$_2$CH$_2$CH$_2$CH$_3$ $^1$H NMR(CDCl$_3$, 500 MHz) δ 0.84(t, CH$_2$CH$_2$CH$_2$CH$_3$), 1.09(t, CH$_2$CH$_3$), 1.13–1.29(m, CH$_2$CH$_2$CH$_2$CH$_3$), 1.38 and 1.55(two m, CH$_2$CH$_2$CH$_2$CH$_3$), 1.93 and 2.18 (two ddd, 1-CH$_2$), 2.44 and 2.64(two dq, CH$_2$CH$_3$), 2.46 and 2.56(two ddd, 2-CH$_2$), 2.60 and 2.86(two d, 9-CH$_2$), 6.69(d, H-6), and 7.31(d, H-5); mass spectrum m/z 302.2(M+1).

28    R$^3$ = CH$_2$CH$_3$     7-amino-4,9a-diethyl-6-fluoro-8-methyl-1,2,9,9a-
      R$^7$ = CH$_3$       tetrahydro-3H-fluoren-3-one
      R$^{10}$ = CH$_2$CH$_3$ $^1$H NMR(CDCl$_3$, 500 MHz) δ 0.84(t, 9a-CH$_2$CH$_3$), 1.09(t, 4-CH$_2$CH$_3$), 1.47 and 1.60(two dq, 9a-CH$_2$CH$_3$), 1.96 and 2.23(two ddd, 1-CH$_2$), 2.28(s, 8-CH$_3$), 2.44 and 2.63(two m, 4-CH$_2$CH$_3$), 2.45 and 2.55(two m, 2-CH$_2$), 2.54 and 2.90(two d, 9-CH$_2$), and 7.27(d, H-5).

29    R$^3$ = Cl          7-amino-4-chloro-9a-ethyl-6-fluoro-8-methyl-
      R$^7$ = CH$_3$       1,2,9,9a-tetrahydro-3H-fluoren-3-one
      R$^{10}$ = CH$_2$CH$_3$ -continued $^1$H NMR(CDCl$_3$, 500 MHz) δ 0.87(t, CH$_2$CH$_3$), 1.57 and 1.68(two dq, CH$_2$CH$_3$), 2.04 and 2.25(two ddd, 1-CH$_2$), 2.12(s, 8-CH$_3$), 2.61 and 2.95(two d, 9-CH$_2$), 2.68 (m, 2-CH$_2$), and 7.93(d, H-5).

| 30 | R$^3$ = Br | 7-amino-4-bromo-9a-ethyl-6-fluoro-8-methyl- |
|    | R$^7$ = CH$_3$ | 1,2,9,9a-tetrahydro-3H-fluoren-3-one |
|    | R$^{10}$ = CH$_2$CH$_3$ | |

$^1$H NMR(CDCl$_3$, 500 MHz) δ 0.86(t, CH$_2$CH$_3$), 1.56 and 1.67(two dq, CH$_2$CH$_3$), 2.04 and 2.24(two ddd, 1-CH$_2$), 2.12(s, 8-CH$_3$), 2.61 and 2.94(two d, 9-CH$_2$), 2.65–2.77(m, 2-CH$_2$), and 8.15(d, H-5).

| 31 | R$^3$ = CH$_3$ | 7-amino-9a-butyl-6-fluoro-4,8-dimethyl-1,2,9,9a- |
|    | R$^7$ = CH$_3$ | tetrahydro-3H-fluoren-3-one |
|    | R$^{10}$ = CH$_2$CH$_2$CH$_2$CH$_3$ | |

$^1$H NMR(CDCl$_3$, 500 MHz) δ 0.84(t, CH$_2$CH$_2$CH$_2$CH$_3$), 1.14–1.27(m, CH$_2$CH$_2$CH$_2$CH$_3$), 1.37 and 1.57(two m, CH$_2$CH$_2$CH$_2$CH$_3$), 1.95 and 2.22(two ddd, 1-CH$_2$), 2.04(s, 4-CH$_3$), 2.20(s, 8-CH$_3$), 2.46 and 2.57(two ddd, 2-CH$_2$), 2.55 and 2.90(two d, 9-CH$_2$), and 7.29(d, H-5); mass spectrum m/z 302.2(M+1).

| 32 | R$^3$ = CH$_2$CH$_3$ | 7-amino-9a-butyl-4-ethyl-6-fluoro-8-methyl- |
|    | R$^7$ = CH$_3$ | 1,2,9,9a-tetrahydro-3H-fluoren-3-one |
|    | R$^{10}$ = CH$_2$CH$_2$CH$_2$CH$_3$ | |

$^1$H NMR(CDCl$_3$, 500 MHz) δ 0.84(t, CH$_2$CH$_2$CH$_2$CH$_3$), 1.09(t, CH$_2$CH$_3$), 1.14–1.28(m, CH$_2$CH$_2$CH$_2$CH$_3$), 1.37 and 1.55(two m, CH$_2$CH$_2$CH$_2$CH$_3$), 1.94 and 2.21 (two ddd, 1-CH$_2$), 2.18(s, 8-CH$_3$), 2.44 and 2.55(two ddd, 2-CH$_2$), 2.44 and 2.63 (two m, CH$_2$CH$_3$), 2.54 and 2.89(two d, 9-CH$_2$), and 7.25(d, H-5); mass spectrum m/z 316.2(M+1).

| 33 | R$^3$ = Cl | 7-amino-9a-butyl-4-chloro-6-fluoro-8-methyl- |
|    | R$^7$ = CH$_3$ | 1,2,9,9a-tetrahydro-3H-fluoren-3-one |
|    | R$^{10}$ = CH$_2$CH$_2$CH$_2$CH$_3$ | |

$^1$H NMR(CDCl$_3$, 500 MHz) δ 0.85(t, CH$_2$CH$_2$CH$_2$CH$_3$), 1.13–1.29(m, CH$_2$CH$_2$CH$_2$CH$_3$), 1.47 and 1.64(two m, CH$_2$CH$_2$CH$_2$CH$_3$), 2.03 and 2.25(two ddd, 1-CH$_2$), 2.12(s, 8-CH$_3$), 2.62 and 2.95(two d, 9-CH$_2$), 2.67(m, 2-CH$_2$), and 7.93(d, H-5); mass spectrum m/z 322.2(M+1).

| 34 | R$^3$ = CN | 7-amino-9a-butyl-4-cyano-6-fluoro-8-methyl- |
|    | R$^7$ = CH$_3$ | 1,2,9,9a-tetrahydro-3H-fluoren-3-one |
|    | R$^{10}$ = CH$_2$CH$_2$CH$_2$CH$_3$ | |

$^1$H NMR(CDCl$_3$, 500 MHz) δ 0.85(t, CH$_2$CH$_2$CH$_2$CH$_3$), 1.12–1.29(m, CH$_2$CH$_2$CH$_2$CH$_3$), 1.40 and 1.63(two m, CH$_2$CH$_2$CH$_2$CH$_3$), 1.95 and 2.28(two ddd, 1-CH$_2$), 2.13(s, 8-CH$_3$), 2.57(m, 2-CH$_2$), 2.60 and 2.97(two d, 9-CH$_2$), and 7.94(d, H-5); mass spectrum m/z 313.2(M+1).

| 35 | R$^3$ = CF$_3$ | 7-amino-9a-butyl-8-methyl-6-fluoro-4- |
|    | R$^7$ = CH$_3$ | trifluoromethyl-1,2,9,9a-tetrahydro-3H-fluoren-3- |
|    | R$^{10}$ = CH$_2$CH$_2$CH$_2$CH$_3$ | one |

$^1$H NMR(CDCl$_3$, 500 MHz) δ 0.83(t, CH$_2$CH$_2$CH$_2$CH$_3$), 1.13–1.27(m, CH$_2$CH$_2$CH$_2$CH$_3$), 1.30 and 1.53(two m, CH$_2$CH$_2$CH$_2$CH$_3$), 2.01 and 2.20(two ddd, 1-CH$_2$), 2.14(s, 8-CH$_3$), 2.54(m, 2-CH$_2$), 2.64 and 2.92(two d, 9-CH$_2$), 4.24 (br s, NH$_2$), and 7.40(d, H-5); mass spectrum m/z 356.2(M+1).

| 36 | R$^3$ = CH$_3$ | 7-amino-9a-ethyl-6,8-difluoro-4-methyl-1,2,9,9a- |
|    | R$^7$ = F | tetrahydro-3H-fluoren-3-one |
|    | R$^{10}$ = CH$_2$CH$_3$ | |

$^1$H NMR(CDCl$_3$, 500 MHz) δ 0.86(t, CH$_2$CH$_3$), 1.46 and 1.60(two dq, CH$_2$CH$_3$), 1.97 and 2.24(two ddd, 1-CH$_2$), 2.03(s, 4-CH$_3$), 2.46 and 2.54(two ddd, 2-CH$_2$), 2.57 and 3.03(two d, 9-CH$_2$), and 7.21(d, H-5); mass spectrum m/z 278.2(M+1).

| 37 | R$^3$ = CH$_2$CH$_3$ | 7-amino-4,9a-diethyl-6,8-difluoro-1,2,9,9a- |
|    | R$^7$ = F | tetrahydro-3H-fluoren-3-one |
|    | R$^{10}$ = CH$_2$CH$_3$ | |

$^1$H NMR(CDCl$_3$, 500 MHz) δ 0.85(t, 9a-CH$_2$CH$_3$), 1.07(t, 4-CH$_2$CH$_3$), 1.47 and 1.59(two dq, 9a-CH$_2$CH$_3$), 1.96 and 2.22(two ddd, 1-CH$_2$), 2.41 and 2.62(two m, 4-CH$_2$CH$_3$), 2.44 and 2.52(two ddd, 2-CH$_2$), 2.56 and 3.01(two d, 9-CH$_2$), 3.50(br s, NH$_2$), and 7.16(d, H-5); mass spectrum m/z 292.2(M+1).

| 38 | R$^3$ = Br | 7-amino-4-bromo-9a-ethyl-6,8-difluoro-1,2,9,9a- |
|    | R$^7$ = F | tetrahydro-3H-fluoren-3-one |
|    | R$^{10}$ = CH$_2$CH$_3$ | |

$^1$H NMR(CDCl$_3$, 500 MHz) δ 0.88(t, CH$_2$CH$_3$), 1.56 and 1.67(two dq, CH$_2$CH$_3$), 2.07 and 2.27(two ddd, 1-CH$_2$), 2.65 and 3.08(two d, 9-CH$_2$), 2.71(m, 2-CH$_2$), 4.2 (br s, NH$_2$), and 8.08(d, H-5).

| 39 | R$^3$ = CF$_3$ | 7-amino-9a-ethyl-6,8-difluoro-4-trifluoromethyl- |
|    | R$^7$ = F | 1,2,9,9a-tetrahydro-3H-fluoren-3-one |
|    | R$^{10}$ = CH$_2$CH$_3$ | |

$^1$H NMR(CDCl$_3$, 500 MHz) δ 0.87(t, CH$_2$CH$_3$), 1.41 and 1.57(two dq, CH$_2$CH$_3$), 2.04 and 2.23(two ddd, 1-CH$_2$), 2.55(m, 2-CH$_2$), 2.67 and 3.07(two d, 9-CH$_2$), 4.27 (br s, NH$_2$), and 7.36(d, H-5); mass spectrum m/z 332.1(M+1).

| 40 | R$^3$ = CH$_3$ | 7-amino-9a-butyl-6,8-difluoro-4-methyl-1,2,9,9a- |
|    | R$^7$ = F | tetrahydro-3H-fluoren-3-one |
|    | R$^{10}$ = CH$_2$CH$_2$CH$_2$CH$_3$ | |

$^1$H NMR(CDCl$_3$, 500 MHz) δ 0.85(t, CH$_2$CH$_2$CH$_2$CH$_3$), 1.14–1.29(m, CH$_2$CH$_2$CH$_2$CH$_3$), 1.37 and 1.57(two m, CH$_2$CH$_2$CH$_2$CH$_3$), 1.97 and 2.23(two ddd, 1-CH$_2$), 2.03(s, 4-CH$_3$), 2.46 and 2.55(two ddd, 2-CH$_2$), 2.58 and 3.03(two d, 9-CH$_2$), and 7.21(d, H-5); mass spectrum m/z 306.2(M+1).

| 41 | R$^3$ = CH$_3$ | 7-amino-8-chloro-9a-ethyl-6-fluoro-4-methyl- |
|    | R$^7$ = Cl | 1,2,9,9a-tetrahydro-3H-fluoren-3-one |

-continued

R$^{10}$ = CH$_2$CH$_3$
$^1$H NMR(CDCl$_3$, 500 MHz) δ 0.86(t, CH$_2$CH$_3$), 1.48 and 1.61(two dq, CH$_2$CH$_3$), 1.97 and 2.24(two ddd, 1-CH$_2$), 2.03(s, 4-CH$_3$), 2.46 and 2.55(two ddd, 2-CH$_2$), 2.61 and 3.00(two d, 9-CH$_2$), 4.40(br s, NH$_2$), and 7.32(d, H-5); mass spectrum m/z 294.1(M+1).

42  R$^3$ = CH$_2$CH$_3$      7-amino-8-chloro-4,9a-diethyl-6-fluoro-1,2,9,9a-
    R$^7$ = Cl               tetrahydro-3H-fluoren-3-one
    R$^{10}$ = CH$_2$CH$_3$
$^1$H NMR(CDCl$_3$, 500 MHz) δ 0.85(t, 9a-CH$_2$CH$_3$), 1.08(t, 4-CH$_2$CH$_3$), 1.49 and 1.62(two dq, 9a-CH$_2$CH$_3$), 1.96 and 2.23(two ddd, 1-CH$_2$), 2.41 and 2.61(two dq, 4-CH$_2$CH$_3$), 2.45 and 2.54(two ddd, 2-CH$_2$), 2.60 and 2.99(two d, 9-CH$_2$), 4.3(br s, NH$_2$), and 7.27(d, H-5); mass spectrum m/z 308.1(M+1).

43  R$^3$ = Cl               7-amino-4,8-dichloro-9a-ethyl-6-fluoro-1,2,9,9a-
    R$^7$ = Cl               tetrahydro-3H-fluoren-3-one
    R$^{10}$ = CH$_2$CH$_3$
$^1$H NMR(CDCl$_3$, 500 MHz) δ 0.88(t, CH$_2$CH$_3$), 1.59 and 1.69(two dq, CH$_2$CH$_3$), 2.06 and 2.27(two ddd, 1-CH$_2$), 2.64–2.74(m, 2-CH$_2$), 2.68 and 3.05(two d, 9-CH$_2$), 4.56(br s, NH$_2$), and 7.97(d, H-5); mass spectrum m/z 314.1(M+1), 316.1(M+3).

44  R$^3$ = Br               7-amino-4-bromo-8-chloro-9a-ethyl-6-fluoro-
    R$^7$ = Cl               1,2,9,9a-tetrahydro-3H-fluoren-3-one
    R$^{10}$ = CH$_2$CH$_3$
$^1$H NMR(CDCl$_3$, 500 MHz) δ 0.88(t, CH$_2$CH$_3$), 1.58 and 1.68(two dq, CH$_2$CH$_3$), 2.06 and 2.26(two ddd, 1-CH$_2$), 2.68 and 3.04(two d, 9-CH$_2$), 2.71(m, 2-CH$_2$), 4.58 (br s, NH$_2$), and 8.19(d, H-5).

45  R$^3$ = I                7-amino-8-chloro-9a-ethyl-6-fluoro-4-iodo-
    R$^7$ = Cl               1,2,9,9a-tetrahydro-3H-fluoren-3-one
    R$^{10}$ = CH$_2$CH$_3$
$^1$H NMR(CDCl$_3$, 500 MHz) δ 0.87(t, CH$_2$CH$_3$), 1.55 and 1.65(two dq, CH$_2$CH$_3$), 2.05 and 2.25(two ddd, 1-CH$_2$), 2.67 and 3.00(two d, 9-CH$_2$), 2.73 and 2.78(two ddd, 2-CH$_2$), 4.58(s, NH$_2$), and 8.47(d, H-5); mass spectrum m/z 406.0(M+1).

46  R$^3$ = 2-furyl          7-amino-8-chloro-9a-ethyl-6-fluoro-4-(2-furyl)-
    R$^7$ = Cl               1,2,9,9a-tetrahydro-3H-fluoren-3-one
    R$^{10}$ = CH$_2$CH$_3$
$^1$H NMR(CDCl$_3$, 500 MHz) δ 0.92(t, CH$_2$CH$_3$), 1.62 and 1.76(two dq, CH$_2$CH$_3$), 2.10 and 2.31(two ddd, 1-CH$_2$), 2.58 and 2.65(two ddd, 2-CH$_2$), 2.69 and 3.06(two d, 9-CH$_2$), 4.43(br s, NH$_2$), 6.10(d, H-5), 6.38(d, furyl H-3), 6.54(dd, furyl H-4), and 7.52(d, furyl H-5).

47  R$^3$ = CH$_3$           7-amino-8-chloro-6-fluoro-4-methyl-9a-propyl-
    R$^7$ = Cl               1,2,9,9a-tetrahydro-3H-fluoren-3-one
    R$^{10}$ = CH$_2$CH$_2$CH$_3$
$^1$H NMR(CDCl$_3$, 500 MHz) δ 0.84(t, CH$_2$CH$_2$CH$_3$), 1.21(m, CH$_2$CH$_2$CH$_3$), 1.41 and 1.54(two dt, CH$_2$CH$_2$CH$_3$), 1.97 and 2.22(two ddd, 1-CH$_2$), 2.03(s, 4-CH$_3$), 2.46 and 2.58(two ddd, 2-CH$_2$), 2.63 and 2.99(two d, 9-CH$_2$), 4.40(br s, NH$_2$), and 7.31(d, H-5); mass spectrum m/z 308.2(M+1).

48  R$^3$ = CH$_2$CH$_3$      7-amino-8-chloro-4-ethyl-6-fluoro-9a-propyl-
    R$^7$ = Cl               1,2,9,9a-tetrahydro-3H-fluoren-3-one
    R$^{10}$ = CH$_2$CH$_2$CH$_3$
$^1$H NMR(CDCl$_3$, 500 MHz) δ 0.84(t, CH$_2$CH$_2$CH$_3$), 1.08(t, CH$_2$CH$_3$), 1.21(m, CH$_2$CH$_2$CH$_3$), 1.41 and 1.52(two dq, CH$_2$CH$_2$CH$_3$), 1.96 and 2.20(two ddd, 1-CH$_2$), 2.41 and 2.61(two dq, CH$_2$CH$_3$), 2.44 and 2.55(two ddd, 2-CH$_2$), 2.62 and 2.98(two d, 9-CH$_2$), 4.37(br s, NH$_2$), and 7.26(d, H-5); mass spectrum m/z 322.2 (M+1).

49  R$^3$ = Cl               7-amino-4,8-dichloro-6-fluoro-9a-propyl-1,2,9,9a-
    R$^7$ = Cl               tetrahydro-3H-fluoren-3-one
    R$^{10}$ = CH$_2$CH$_2$CH$_3$
$^1$H NMR(CDCl$_3$, 500 MHz) δ 0.87(t, CH$_2$CH$_2$CH$_3$), 1.15–1.31(m, CH$_2$CH$_2$CH$_3$), 1.51 and 1.62(two dt, CH$_2$CH$_2$CH$_3$), 2.07 and 2.25(two ddd, 1-CH$_2$), 2.66 and 2.72 (two ddd, 2-CH$_2$), 2.72 and 3.06(two d, 9-CH$_2$), 4.56(br s, NH$_2$), and 7.97(d, H-5); mass spectrum m/z 328.1(M+1), 330.1(M+3).

50  R$^3$ = Br               7-amino-4-bromo-8-chloro-6-fluoro-9a-propyl-
    R$^7$ = Cl               1,2,9,9a-tetrahydro-3H-fluoren-3-one
    R$^{10}$ = CH$_2$CH$_2$CH$_3$
$^1$H NMR(CDCl$_3$, 500 MHz) δ 0.86(t, CH$_2$CH$_2$CH$_3$), 1.22(m, CH$_2$CH$_2$CH$_3$), 1.50 and 1.60(two ddd, CH$_2$CH$_2$CH$_3$), 2.06 and 2.25(two ddd, 1-CH$_2$), 2.70 and 3.04 (two d, 9-CH$_2$), 2.72(m, 2-CH$_2$), 4.55(br s, NH$_2$), and 8.19(d, H-5); mass spectrum m/z 372.0(M+1).

51  R$^3$ = I                7-amino-8-chloro-6-fluoro-4-iodo-9a-propyl-
    R$^7$ = Cl               1,2,9,9a-tetrahydro-3H-fluoren-3-one
    R$^{10}$ = CH$_2$CH$_2$CH$_3$
$^1$H NMR(CDCl$_3$, 500 MHz) δ 0.85(t, CH$_2$CH$_2$CH$_3$), 1.11–1.31(m, CH$_2$CH$_2$CH$_3$), 1.47 and 1.58(two dt, CH$_2$CH$_2$CH$_3$), 2.05 and 2.23(two ddd, 1-CH$_2$), 2.70 and 3.00 (two d, 9-CH$_2$), 2.70–2.85(m, 2-CH$_2$), 4.59(s, NH$_2$), and 8.47(d, H-5).

52  R$^3$ = 2-furyl          7-amino-8-chloro-6-fluoro-4-(2-furyl)-9a-propyl-
    R$^7$ = Cl               1,2,9,9a-tetrahydro-3H-fluoren-3-one
    R$^{10}$ = CH$_2$CH$_2$CH$_3$
$^1$H NMR(CDCl$_3$, 500 MHz) δ 0.89(t, CH$_2$CH$_2$CH$_3$), 1.17–1.37(m, CH$_2$CH$_2$CH$_3$), 1.54 and 1.68(two dt, CH$_2$CH$_2$CH$_3$), 2.10 and 2.29(two ddd, 1-CH$_2$), 2.58 and 2.67 (two ddd, 2-CH$_2$), 2.71 and 3.06(two d, 9-CH$_2$), 4.45(s, NH$_2$), 6.09(d, H-5), 6.38(d, furyl H-3), 6.54(dd, furyl H-4), and 7.52(d, furyl H-5); mass spectrum m/z 360.2

(M+1).

| | | |
|---|---|---|
| 53 | $R^3$ = $CH_3$ | 7-amino-9a-butyl-8-chloro-6-fluoro-4-methyl- |
| | $R^7$ = Cl | 1,2,9,9a-tetrahydro-3H-fluoren-3-one |
| | $R^{10}$ = $CH_2CH_2CH_2CH_3$ | |

$^1$H NMR(CDCl$_3$, 500 MHz) δ 0.84(t, CH$_2$CH$_2$CH$_2$CH$_3$), 1.13–1.27(m, CH$_2$CH$_2$CH$_2$CH$_3$), 1.38 and 1.57(two m, CH$_2$CH$_2$CH$_2$CH$_3$), 1.96 and 2.23(two ddd, 1-CH$_2$), 2.02(s, 4-CH$_3$), 2.46 and 2.56(two ddd, 2-CH$_2$), 2.61 and 2.99(two d, 9-CH$_2$), 4.38(br s, NH$_2$), and 7.32(d, H-5); mass spectrum m/z 322.2(M+1).

| | | |
|---|---|---|
| 54 | $R^3$ = $CH_3$ | 7-amino-9a-butyl-8-chloro-4-ethyl-6-fluoro- |
| | $R^7$ = Cl | 1,2,9,9a-tetrahydro-3H-fluoren-3-one |
| | $R^{10}$ = $CH_2CH_2CH_2CH_3$ | |

$^1$H NMR(CDCl$_3$, 500 MHz) δ 0.85(t, CH$_2$CH$_2$CH$_2$CH$_3$), 1.08(t, CH$_2$CH$_3$), 1.14–1.30(m, CH$_2$CH$_2$CH$_2$CH$_3$), 1.39 and 1.55(two m, CH$_2$CH$_2$CH$_2$CH$_3$), 1.96 and 2.22 (two ddd, 1-CH$_2$), 2.41 and 2.61(two dq, CH$_2$CH$_3$), 2.44 and 2.55(two ddd, 2-CH$_2$), 2.61 and 2.99(two d, 9-CH$_2$), 4.39(br s, NH$_2$), and 7.27(d, H-5); mass spectrum m/z 336.2(M+1).

| | | |
|---|---|---|
| 55 | $R^3$ = C(=O)CH$_3$ | 4-acetyl-7-amino-9a-butyl-8-chloro-6-fluoro- |
| | $R^7$ = Cl | 1,2,9,9a-tetrahydro-3H-fluoren-3-one |
| | $R^{10}$ = $CH_2CH_2CH_2CH_3$ | |

$^1$H NMR(CDCl$_3$, 500 MHz) δ 0.86(t, CH$_2$CH$_2$CH$_2$CH$_3$), 1.17–1.31(m, CH$_2$CH$_2$CH$_2$CH$_3$), 1.44 and 1.64(two m, CH$_2$CH$_2$CH$_2$CH$_3$), 2.02 and 2.28(two ddd, 1-CH$_2$), 2.38(s, COCH$_3$), 2.50 and 2.56(two ddd, 2-CH$_2$), 2.65 and 3.03(two d, 9-CH$_2$), 4.55(br s, NH ), and 7.17(d, H-5).

| | | |
|---|---|---|
| 56 | $R^3$ = $CH_3$ | 7-amino-8-bromo-9a-ethyl-6-fluoro-4-methyl- |
| | $R^7$ = Br | 1,2,9,9a-tetrahydro-3H-fluoren-3-one |
| | $R^{10}$ = $CH_2CH_3$ | |

$^1$H NMR(CDCl$_3$, 500 MHz) δ 0.85(t, CH$_2$CH$_3$), 1.49 and 1.62(two dq, CH$_2$CH$_3$), 1.97 and 2.23(two ddd, 1-CH$_2$), 2.03(s, 4-CH$_3$), 2.46 and 2.55(two ddd, 2-CH$_2$), 2.60 and 2.95(two d, 9-CH$_2$), 4.45(br s, NH$_2$), and 7.34(d, H-5).

| | | |
|---|---|---|
| 57 | $R^3$ = $CH_2CH_3$ | 7-amino-8-bromo-4,9a-diethyl-6-fluoro-1,2,9,9a- |
| | $R^7$ = Br | tetrahydro-3H-fluoren-3-one |
| | $R^{10}$ = $CH_2CH_3$ | |

$^1$H NMR(CDCl$_3$, 500 MHz) δ 0.84(t, 9a-CH$_2$CH$_3$), 1.07(t, 4-CH$_2$CH$_3$), 1.49 and 1.60(two dq, 9a-CH$_2$CH$_3$), 1.96 and 2.22(two ddd, 1-CH$_2$), 2.41 and 2.62(two dq, 4-CH$_2$CH$_3$), 2.44 and 2.53(two ddd, 2-CH$_2$), 2.60 and 2.94(two d, 9-CH$_2$), 4.46(br s, NH$_2$), and 7.29(d, H-5).

| | | |
|---|---|---|
| 58 | $R^3$ = Br | 7-amino-4,8-dibromo-9a-ethyl-6-fluoro-1,2,9,9a- |
| | $R^7$ = Br | tetrahydro-3H-fluoren-3-one |
| | $R^{10}$ = $CH_2CH_3$ | |

$^1$H NMR(CDCl$_3$, 500 MHz) δ 0.86(t, CH$_2$CH$_3$), 1.58 and 1.68(two dq, CH$_2$CH$_3$), 2.05 and 2.25(two ddd, 1-CH$_2$), 2.67 and 2.99(two d, 9-CH$_2$), 2.70(m, 2-CH$_2$), 4.65 (br s, NH$_2$), and 8.21(d, H-5).

| | | |
|---|---|---|
| 59 | $R^3$ = $CH_2CH_3$ | 7-amino-8-bromo-9a-butyl-4-ethyl-6-fluoro- |
| | $R^7$ = Br | 1,2,9,9a-tetrahydro-3H-fluoren-3-one |
| | $R^{10}$ = $CH_2CH_2CH_2CH_3$ | |

$^1$H NMR(CDCl$_3$, 500 MHz) δ 0.84(t, CH$_2$CH$_2$CH$_2$CH$_3$), 1.08(t, CH$_2$CH$_3$), 1.13–1.27(m, CH$_2$CH$_2$CH$_2$CH$_3$), 1.40 and 1.55(two m, CH$_2$CH$_2$CH$_2$CH$_3$), 1.95 and 2.22 (two ddd, 1-CH$_2$), 2.41 and 2.62(two dq, CH$_2$CH$_3$), 2.44 and 2.54(two ddd, 2-CH$_2$), 2.60 and 2.95(two d, 9-CH$_2$), 4.45(br s, NH$_2$), and 7.29(d, H-5).

| | | |
|---|---|---|
| 60 | $R^3$ = $CH_3$ | 7-amino-9a-ethyl-6-fluoro-4-methyl-8-nitro- |
| | $R^7$ = NO$_2$ | 1,2,9,9a-tetrahydro-3H-fluoren-3-one |
| | $R^{10}$ = $CH_2CH_3$ | |

$^1$H NMR(CDCl$_3$, 500 MHz) δ 0.85(t, CH$_2$CH$_3$), 1.46 and 1.61(two dq, CH$_2$CH$_3$), 1.98 and 2.28(two ddd, 1-CH$_2$), 2.05(s, 4-CH$_3$), 2.49 and 2.56(two ddd, 2-CH$_2$), 3.06 and 3.45(two d, 9-CH$_2$), 6.31(br s, NH$_2$), and 7.62(d, H-5); mass spectrum m/z 305.2(M+1).

| | | |
|---|---|---|
| 61 | $R^3$ = $CH_2CH_3$ | 7-amino-4,9a-diethyl-6-fluoro-8-fluoro-1,2,9,9a- |
| | $R^7$ = NO$_2$ | tetrahydro-3H-fluoren-3-one |
| | $R^{10}$ = $CH_2CH_3$ | |

$^1$H NMR(CDCl$_3$, 500 MHz) δ 0.84(t, 9a-CH$_2$CH$_3$), 1.09(t, 4-CH$_2$CH$_3$), 1.47 and 1.59(two dq, 9a-CH$_2$CH$_3$), 1.97 and 2.26(two ddd, 1-CH$_2$), 2.40 and 2.63(two dq, 4-CH$_2$CH$_3$), 2.47 and 2.54(two ddd, 2-CH$_2$), 3.06 and 3.43(two d, 9-CH$_2$), 6.31(br s, NH$_2$), and 7.54(d, H-5); mass spectrum m/z 319.2(M+1).

| | | |
|---|---|---|
| 62 | $R^3$ = $CH_2CH_3$ | 7-amino-9a-butyl-4-ethyl-6-fluoro-8-nitro- |
| | $R^7$ = NO$_2$ | 1,2,9,9a-tetrahydro-3H-fluoren-3-one |
| | $R^{10}$ = $CH_2CH_2CH_2CH_3$ | |

$^1$H NMR(CDCl$_3$, 500 MHz) δ 0.84(t, CH$_2$CH$_2$CH$_2$CH$_3$), 1.09(t, CH$_2$CH$_3$), 1.13–1.29(m, CH$_2$CH$_2$CH$_2$CH$_3$), 1.38 and 1.56(two m, CH$_2$CH$_2$CH$_2$CH$_3$), 1.96 and 2.26 (two ddd, 1-CH$_2$), 2.40 and 2.63(two dq, CH$_2$CH$_3$), 2.47 and 2.55(two ddd, 2-CH$_2$), 3.07 and 3.43(two d, 9-CH$_2$), 6.32(br s, NH$_2$), and 7.54(d, H-5).

| | | |
|---|---|---|
| 63 | $R^3$ = $CH_2CH_3$ | 7,8-diamino-9a-butyl-4-ethyl-6-fluoro-1,2,9,9a- |
| | $R^7$ NH$_2$ | tetrahydro-3H-fluoren-3-one |
| | $R^{10}$ = $CH_2CH_2CH_2CH_3$ | |

$^1$H NMR(CDCl$_3$, 500 MHz) δ 0.84(t, CH$_2$CH$_2$CH$_2$CH$_3$), 1.09(t, CH$_2$CH$_3$), 1.14–1.29(m, CH$_2$CH$_2$CH$_2$CH$_3$), 1.40 and 1.56(two m, CH$_2$CH$_2$CH$_2$CH$_3$), 1.97 and 2.23 (two ddd, 1-CH$_2$), 2.44 and 2.55(two ddd, 2-CH$_2$), 2.44 and 2.62(two br m, CH$_2$CH$_3$), 2.47 and 2.84(two br d, 9-CH$_2$), and 7.03(br d, H-5); mass spectrum m/z 317.2(M+1).

EXAMPLE 64

CHIRAL HPLC RESOLUTION OF RACEMIC 7-AMINO-4-BROMO-9a-BUTYL-8-CHLORO-6-FLUORO-1,2,9,9a-TETRAHYDRO-3H-FLUOREN-3-ONE

Racemic 7-amino-4-bromo-9a-butyl 8-chloro-6-fluoro-1,2,9,9a-tetrahydro-3H-fluoren-3-one (175 mg) was resolved by preparative, chiral HPLC using the following conditions.
Column: 2×25 cm Chiralcel OD
Injection size: 1.5 mL of a 10 mg/mL solution in EtOH
Eluant: 10% EtOH in heptane
Flow rate: 6–7 mL/min The product fractions (UV detection) were divided into three groups. The early fractions gave pure enantiomer A and the latter fractions gave pure enatiomer B. Intermediate fractions provide a mixture of the two enantiomers.

EXAMPLE 65

CHIRAL HPLC RESOLUTION OF RACEMIC 7-AMINO-9a-BUTYL-8-CHLORO-6-FLUORO-4-(2-FURYL)-1,2,9,9a-TETRAHYDRO-3H-FLUOREN-3-ONE

Racemic 7-amino-9a-butyl-8-chloro-6-fluoro-4-(2-furyl)-1,2,9,9a-tetrahydro-3H-fluoren-3-one (230 mg) was resolved by preparative, chiral HPLC using the following conditions.
Column: 2×25 cm Chiralcel OJ
Injection size: 1–2 mL of a 20 mg/mL solution in EtOH
Eluant: 20% EtOH in heptane
Flow rate: 6 mL/min The fractions containing the faster eluting component were pooled, evaporated under vacuum, and the residue lyophilized from benzene to afford enatiomer A as an amorphous solid. Similarly, the fractions containing the slower eluting component afforded enatiomer B as an amorphous solid.

Enantiomer $[\alpha]_D = -314°$ ($c$ 1.010, $CHCl_3$).     A:

Enantiomer $[\alpha]_D = +297°$ ($c$ 1.095, $CHCl_3$).     B:

EXAMPLE 66

The following compounds are prepared using methods analogous to those described in the preceding examples:

| $R^3$ | $R^5$ | $R^7$ | $R^{10}$ |
|---|---|---|---|
| $CH_2CH_3$ | H | F | $CH_2CH_3$ |
| $CH_2CH_3$ | H | F | $CH_2CH_2CH_3$ |
| $CH_3$ | H | F | $CH_2CH_2CH_2CH_3$ |
| $CH_2CH_3$ | H | F | $CH_2CH_2CH_2CH_3$ |
| Cl | H | F | $CH_2CH_2CH_2CH_3$ |
| Br | H | F | $CH_2CH_2CH_2CH_3$ |
| CN | H | F | $CH_2CH_2CH_2CH_3$ |
| $CF_3$ | H | F | $CH_2CH_2CH_2CH_3$ |
| $CH_2CH_3$ | H | Cl | $CH_2CH_3$ |
| $CH_2CH_3$ | H | Cl | $CH_2CH_2CH_3$ |
| $CH_3$ | H | Cl | $CH_2CH_2CH_2CH_3$ |
| $CH_2CH_3$ | H | Cl | $CH_2CH_2CH_2CH_3$ |
| Cl | H | Cl | $CH_2CH_2CH_2CH_3$ |
| Br | H | Cl | $CH_2CH_2CH_2CH_3$ |
| CN | H | Cl | $CH_2CH_2CH_2CH_3$ |
| $CF_3$ | H | Cl | $CH_2CH_2CH_2CH_3$ |
| $CH_2CH_3$ | H | Br | $CH_2CH_3$ |
| $CH_2CH_3$ | H | Br | $CH_2CH_2CH_3$ |
| $CH_3$ | H | Br | $CH_2CH_2CH_2CH_3$ |
| $CH_2CH_3$ | H | Br | $CH_2CH_2CH_2CH_3$ |
| Cl | H | Br | $CH_2CH_2CH_2CH_3$ |
| Br | H | Br | $CH_2CH_2CH_2CH_3$ |
| CN | H | Br | $CH_2CH_2CH_2CH_3$ |
| $CF_3$ | H | Br | $CH_2CH_2CH_2CH_3$ |
| $CH_2CH_3$ | H | $CH_3$ | $CH_2CH_3$ |
| $CH_2CH_3$ | H | $CH_3$ | $CH_2CH_2CH_3$ |
| $CH_2CH_3$ | H | $CH_3$ | $CH_2CH_2CH_2CH_3$ |
| Cl | H | $CH_3$ | $CH_2CH_2CH_2CH_3$ |
| CN | H | $CH_3$ | $CH_2CH_2CH_2CH_3$ |
| $CH_3$ | F | F | $CH_2CH_2CH_3$ |
| $CH_2CH_3$ | F | F | $CH_2CH_2CH_3$ |
| Cl | F | F | $CH_2CH_2CH_3$ |
| Br | F | F | $CH_2CH_2CH_3$ |
| CN | F | F | $CH_2CH_2CH_3$ |

-continued

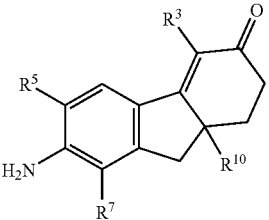

| R³ | R⁵ | R⁷ | R¹⁰ |
|---|---|---|---|
| CF₃ | F | F | CH₂CH₂CH₃ |
| Cl | F | F | CH₂CH₂CH₂CH₃ |
| CN | F | F | CH₂CH₂CH₂CH₃ |
| CHF₂ | F | F | CH₂CH₂CH₂CH₃ |
| C(=O)CH₃ | F | F | CH₂CH₂CH₂CH₃ |
| 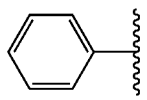 | F | F | CH₂CH₂CH₂CH₃ |
| 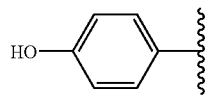 | F | F | CH₂CH₂CH₂CH₃ |
| 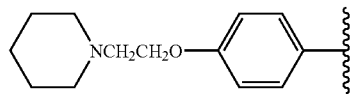 | F | F | CH₂CH₂CH₂CH₃ |
| 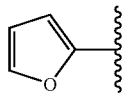 | F | F | CH₂CH₂CH₂CH₃ |
| CH₂CH₃ | F | F | CH₂CH₂F |
| CH₂CH₃ | F | F | CH₂CF₃ |
| CH₂CH₃ | F | F | CH₂CH₂CF₃ |
| CH₂CH₃ | F | F | 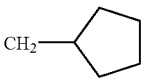 |
| CH₂CH₃ | F | F | 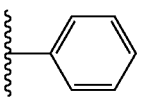 |
| CN | F | Cl | CH₂CH₂CH₃ |
| CF₃ | F | Cl | CH₂CH₂CH₃ |
| CN | F | Cl | CH₂CH₂CH₂CH₃ |
| CF₃ | F | Cl | CH₂CH₂CH₂CH₃ |
| CHF₂ | F | Cl | CH₂CH₂CH₂CH₃ |
| 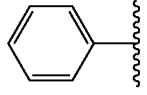 | F | Cl | CH₂CH₂CH₂CH₃ |
| 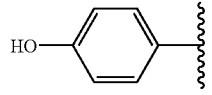 | F | Cl | CH₂CH₂CH₂CH₃ |
| 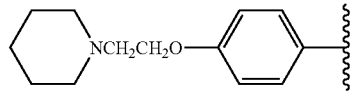 | F | Cl | CH₂CH₂CH₂CH₃ |
| CH₂CH₃ | F | Cl | CH₂CH₂F |
| CH₂CH₃ | F | Cl | CH₂CF₃ |

-continued

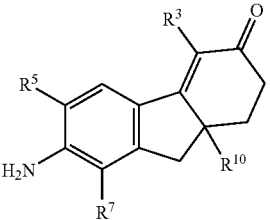

| R³ | R⁵ | R⁷ | R¹⁰ |
|---|---|---|---|
| CH₂CH₃ | F | Cl | CH₂CH₂CF₃ |
| CH₂CH₃ | F | Cl | 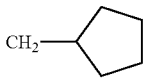 |
| CH₂CH₃ | F | Cl | 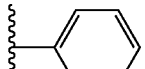 |
| CH₃ | F | Br | CH₂CH₂CH₃ |
| CH₂CH₃ | F | Br | CH₂CH₂CH₃ |
| Cl | F | Br | CH₂CH₂CH₃ |
| Br | F | Br | CH₂CH₂CH₃ |
| CN | F | Br | CH₂CH₂CH₃ |
| CF₃ | F | Br | CH₂CH₂CH₃ |
| Cl | F | Br | CH₂CH₂CH₂CH₃ |
| CN | F | Br | CH₂CH₂CH₂CH₃ |
| CF₃ | F | Br | CH₂CH₂CH₂CH₃ |
| 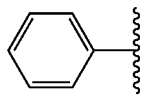 | F | Br | CH₂CH₂CH₂CH₃ |
| 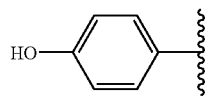 | F | Br | CH₂CH₂CH₂CH₃ |
| 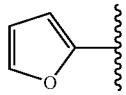 | F | Br | CH₂CH₂CH₂CH₃ |
| CH₂CH₃ | F | Br | CH₂CH₂F |
| CH₂CH₃ | F | Br | CH₂CF₃ |
| CH₂CH₃ | F | Br | CH₂CH₂CF₃ |
| CH₂CH₃ | F | Br | 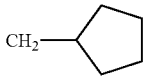 |
| CH₂CH₃ | F | Br | 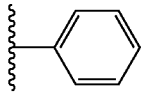 |
| CH₃ | F | CH₃ | CH₂CH₂CH₃ |
| CH₂CH₃ | F | CH₃ | CH₂CH₂CH₃ |
| Cl | F | CH₃ | CH₂CH₂CH₃ |
| Br | F | CH₃ | CH₂CH₂CH₃ |
| CN | F | CH₃ | CH₂CH₂CH₃ |
| CF₃ | F | CH₃ | CH₂CH₂CH₃ |
| 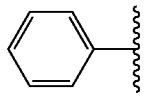 | F | CH₃ | CH₂CH₂CH₂CH₃ |

-continued

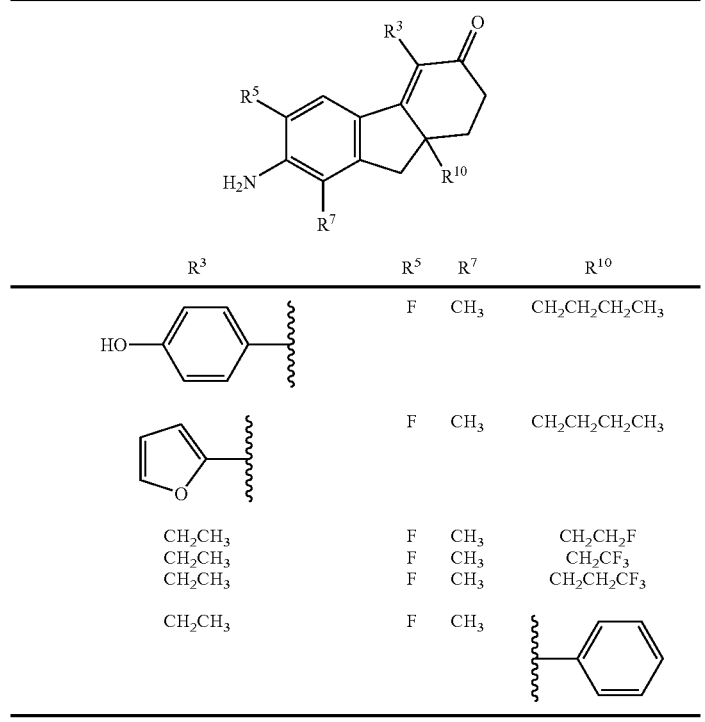

| R³ | R⁵ | R⁷ | R¹⁰ |
|---|---|---|---|
| HO-C₆H₄- | F | CH₃ | CH₂CH₂CH₂CH₃ |
| 2-furyl | F | CH₃ | CH₂CH₂CH₂CH₃ |
| CH₂CH₃ | F | CH₃ | CH₂F |
| CH₂CH₃ | F | CH₃ | CH₂CF₃ |
| CH₂CH₃ | F | CH₃ | CH₂CH₂CF₃ |
| CH₂CH₃ | F | CH₃ | C₆H₅ |

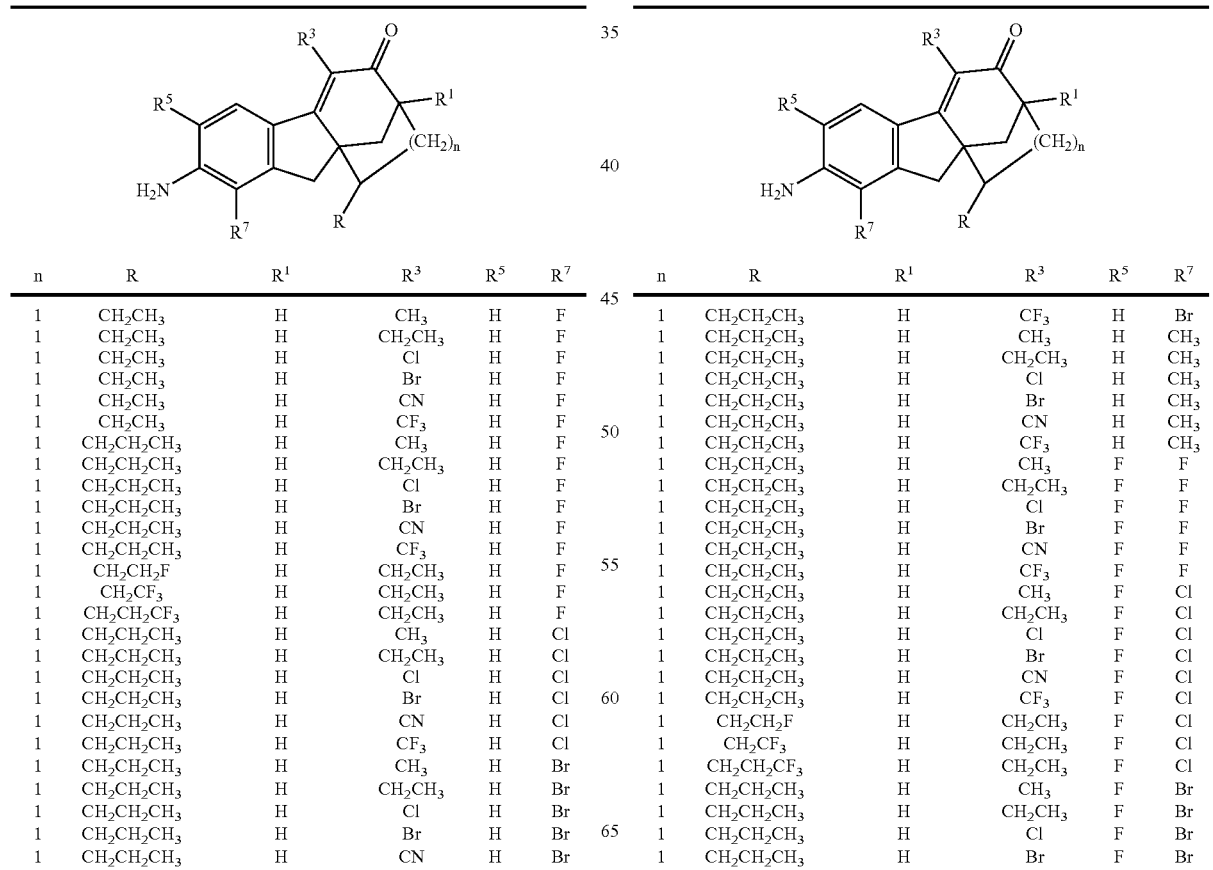

| n | R | R¹ | R³ | R⁵ | R⁷ | n | R | R¹ | R³ | R⁵ | R⁷ |
|---|---|---|---|---|---|---|---|---|---|---|---|
| 1 | CH₂CH₃ | H | CH₃ | H | F | 1 | CH₂CH₂CH₃ | H | CF₃ | H | Br |
| 1 | CH₂CH₃ | H | CH₂CH₃ | H | F | 1 | CH₂CH₂CH₃ | H | CH₃ | H | CH₃ |
| 1 | CH₂CH₃ | H | Cl | H | F | 1 | CH₂CH₂CH₃ | H | CH₂CH₃ | H | CH₃ |
| 1 | CH₂CH₃ | H | Br | H | F | 1 | CH₂CH₂CH₃ | H | Cl | H | CH₃ |
| 1 | CH₂CH₃ | H | CN | H | F | 1 | CH₂CH₂CH₃ | H | Br | H | CH₃ |
| 1 | CH₂CH₃ | H | CF₃ | H | F | 1 | CH₂CH₂CH₃ | H | CN | H | CH₃ |
| 1 | CH₂CH₂CH₃ | H | CH₃ | H | F | 1 | CH₂CH₂CH₃ | H | CF₃ | H | CH₃ |
| 1 | CH₂CH₂CH₃ | H | CH₂CH₃ | H | F | 1 | CH₂CH₂CH₃ | H | CH₃ | F | F |
| 1 | CH₂CH₂CH₃ | H | Cl | H | F | 1 | CH₂CH₂CH₃ | H | CH₂CH₃ | F | F |
| 1 | CH₂CH₂CH₃ | H | Br | H | F | 1 | CH₂CH₂CH₃ | H | Cl | F | F |
| 1 | CH₂CH₂CH₃ | H | CN | H | F | 1 | CH₂CH₂CH₃ | H | Br | F | F |
| 1 | CH₂CH₂CH₃ | H | CF₃ | H | F | 1 | CH₂CH₂CH₃ | H | CN | F | F |
| 1 | CH₂CH₂F | H | CH₂CH₃ | H | F | 1 | CH₂CH₂CH₃ | H | CF₃ | F | F |
| 1 | CH₂CF₃ | H | CH₂CH₃ | H | F | 1 | CH₂CH₂CH₃ | H | CH₃ | F | Cl |
| 1 | CH₂CH₂CF₃ | H | CH₂CH₃ | H | F | 1 | CH₂CH₂CH₃ | H | CH₂CH₃ | F | Cl |
| 1 | CH₂CH₂CH₃ | H | CH₃ | H | Cl | 1 | CH₂CH₂CH₃ | H | Cl | F | Cl |
| 1 | CH₂CH₂CH₃ | H | CH₂CH₃ | H | Cl | 1 | CH₂CH₂CH₃ | H | Br | F | Cl |
| 1 | CH₂CH₂CH₃ | H | Cl | H | Cl | 1 | CH₂CH₂CH₃ | H | CN | F | Cl |
| 1 | CH₂CH₂CH₃ | H | Br | H | Cl | 1 | CH₂CH₂CH₃ | H | CF₃ | F | Cl |
| 1 | CH₂CH₂CH₃ | H | CN | H | Cl | 1 | CH₂CH₂F | H | CH₂CH₃ | F | Cl |
| 1 | CH₂CH₂CH₃ | H | CF₃ | H | Cl | 1 | CH₂CF₃ | H | CH₂CH₃ | F | Cl |
| 1 | CH₂CH₂CH₃ | H | CH₃ | H | Br | 1 | CH₂CH₂CF₃ | H | CH₂CH₃ | F | Cl |
| 1 | CH₂CH₂CH₃ | H | CH₂CH₃ | H | Br | 1 | CH₂CH₂CH₃ | H | CH₃ | F | Br |
| 1 | CH₂CH₂CH₃ | H | Cl | H | Br | 1 | CH₂CH₂CH₃ | H | CH₂CH₃ | F | Br |
| 1 | CH₂CH₂CH₃ | H | Br | H | Br | 1 | CH₂CH₂CH₃ | H | Cl | F | Br |
| 1 | CH₂CH₂CH₃ | H | CN | H | Br | 1 | CH₂CH₂CH₃ | H | Br | F | Br |

-continued

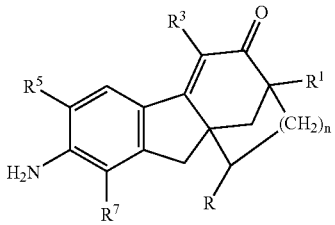

| n | R | R¹ | R³ | R⁵ | R⁷ |
|---|---|---|---|---|---|
| 1 | CH₂CH₂CH₃ | H | CN | F | Br |
| 1 | CH₂CH₂CH₃ | H | CF₃ | F | Br |
| 1 | CH₂CH₂CH₃ | H | CH₃ | F | CH₃ |
| 1 | CH₂CH₂CH₃ | H | CH₂CH₃ | F | CH₃ |
| 1 | CH₂CH₂CH₃ | H | Cl | F | CH₃ |
| 1 | CH₂CH₂CH₃ | H | Br | F | CH₃ |
| 1 | CH₂CH₂CH₃ | H | CN | F | CH₃ |
| 1 | CH₂CH₂CH₃ | H | CF₃ | F | CH₃ |
| 1 | CH₂CH₂CH₃ | CH₃ | CH₂CH₃ | F | F |
| 1 | CH₂CH₂CH₃ | CH₂CH₂CH₃ | CH₂CH₃ | F | F |
| 1 | CH₂CH₂CH₃ | CH₃ | CH₂CH₃ | F | Cl |
| 1 | CH₂CH₂CH₃ | CH₂CH₂CH₃ | CH₂CH₃ | F | Cl |
| 2 | CH₂CH₂CH₃ | H | CH₃ | F | F |
| 2 | CH₂CH₂CH₃ | H | CH₂CH₃ | F | F |
| 2 | CH₂CH₂CH₃ | H | Cl | F | F |
| 2 | CH₂CH₂CH₃ | H | Br | F | F |
| 2 | CH₂CH₂CH₃ | H | CN | F | F |
| 2 | CH₂CH₂CH₃ | H | CF₃ | F | F |
| 2 | CH₂CH₂CH₃ | H | CH₃ | F | Cl |
| 2 | CH₂CH₂CH₃ | H | CH₂CH₃ | F | Cl |
| 2 | CH₂CH₂CH₃ | H | Cl | F | Cl |
| 2 | CH₂CH₂CH₃ | H | Br | F | Cl |
| 2 | CH₂CH₂CH₃ | H | CN | F | Cl |
| 2 | CH₂CH₂CH₃ | H | CF₃ | F | Cl |

Estrogen Receptor Binding Assay

The estrogen receptor ligand binding assays are designed as scintillation proximity assays employing the use of tritiated estradiol and recombinant expressed estrogen receptors. The full length recombinant human ER-α and ER-β proteins are produced in a bacculoviral expression system. ER-α or ER-β extracts are diluted 1:400 in phosphate buffered saline containing 6 mM α-monothiolglycerol. 200 µL aliquots of the diluted receptor preparation are added to each well of a 96-well Flashplate. Plates are covered with Saran Wrap and incubated at 4° C. overnight.

The following morning, a 20 ul aliquot of phosphate buffered saline containing 10% bovine serum albumin is added to each well of the 96 well plate and allowed to incubate at 4° C. for 2 hours. Then the plates are washed with 200 ul of buffer containing 20 mM Tris (pH 7.2), 1 mM EDTA, 10% Glycerol, 50 mM KCl, and 6 mM α-monothiolglycerol. To set up the assay in these receptor coated plates, add 178 ul of the same buffer to each well of the 96 well plate. Then add 20 ul of a 10 nM solution of ³H-estradiol to each well of the plate.

Test compounds are evaluated over a range of concentrations from 0.01 nM to 1000 nM. The test compound stock solutions should be made in 100% DMSO at 100× the final concentration desired for testing in the assay. The amount of DMSO in the test wells of the 96 well plate should not exceed 1%. The final addition to the assay plate is a 2 ul aliquot of the test compound which has been made up in 100% DMSO. Seal the plates and allow them to equilibrate at room temperature for 3 hours. Count the plates in a scintillation counter equipped for counting 96 well plates.

The compounds of Examples 1–63 exhibit binding affinities to the estrogen receptor α-subtype in the range of $IC_{50}$=63 to >10,000 nm, and to the estrogen receptor β-subtype in the range of $IC_{50}$=1.3 to 165 nm.

Pharmaceutical Composition

As a specific embodiment of this invention, 25 mg of tetrahydrofluorenone from Example 16 is formulated with sufficient finely divided lactose to provide a total amount of 580 to 590 mg to fill a size 0, hard-gelatin capsule.

What is claimed is:
1. A compound of the formula:

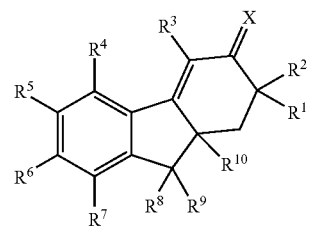

wherein X is selected from the group consisting of: O, N—OR$_a$, N—NR$^a$R$^b$ and C$_{1-6}$alkylidene, wherein said alkylidene group is unsubstituted or substituted with a group selected from hydroxy, amino, O(C$_{1-4}$alkyl), NH(C$_{1-4}$alkyl), or N(C$_{1-4}$alkyl)$_2$;

R¹ is selected from the group consisting of hydrogen, C$_{1-6}$alkyl, C$_{2-6}$alkenyl, and C$_{2-6}$alkynyl, wherein said alkyl, alkenyl and alkynyl groups are either unsubstituted or substituted with a group selected from OR$^c$, SR$^c$, NR$^b$R$^c$,C(═O)R$^c$, C(═O)CH$_2$OH, or phenyl, wherein said phenyl group can either be unsubstituted or substituted with 1–3 substituents independently selected from the group consisting of C$_{1-4}$alkyl, OH, O(C$_{1-4}$alkyl), NH$_2$, NH(C$_{1-4}$alkyl), N(C$_{1-4}$alkyl)$_2$, halo, CN, NO$_2$, CO$_2$H, CO$_2$(C$_{1-4}$alkyl), C(O)H, and C(O)(C$_{1-4}$alkyl);

R² is selected from the group consisting of hydrogen, hydroxy, iodo, O(C═O)R$^c$, C(═O)R$^c$, CO$_2$R$^c$, C$_{1-6}$alkyl, C$_{2-6}$alkenyl, and C$_{2-6}$alkynyl, wherein said alkyl, alkenyl and alkynyl groups are either unsubstituted or substituted with a group selected from OR$^c$, SR$^c$, NR$^b$R$^c$,C(═O)R$^c$, C(═O)CH$_2$OH, or phenyl, wherein said phenyl group can either be unsubstituted or substituted with 1–3 substituents independently selected from the group consisting of C$_{1-4}$alkyl, OH, O(C$_{1-4}$alkyl), NH$_2$, NH(C$_{1-4}$alkyl), N(C$_{1-4}$alkyl)$_2$, halo, CN, NO$_2$, CO$_2$H, CO$_2$(C$_{1-4}$alkyl), C(O)H, and C(O)(C$_{1-4}$alkyl);

or R¹ and R², when taken together with the carbon atom to which they are attached, form a carbonyl group;

or R¹ and R², when taken together, form a C$_{1-6}$alkylidene group, wherein said alkylidene group is either unsubstituted or substituted with a group selected from the group consisting of hydroxy, O(C$_{1-4}$alkyl), N(C$_{1-4}$alkyl)$_2$, and phenyl, wherein said phenyl group can either be unsubstituted or substituted with 1–3 substituents independently selected from the group consisting of C$_{1-4}$alkyl, OH, O(C$_{1-4}$alkyl), NH$_2$, NH(C$_{1-4}$alkyl), NH(C$_{1-4}$alkyl)$_2$, halo, CN, NO$_2$, CO$_2$H, CO$_2$C$_{1-4}$alkyl), C(O)H, and C(O)(C$_{1-4}$alkyl);

R³ is selected from the group consisting of hydrogen, fluoro, chloro, bromo, iodo, cyano, nitro, NR$^a$R$^c$, OR$^a$, C(=O)R$^a$, CO$_2$R$^c$, CONR$^a$R$^c$, SR$^a$, S(=O)R$^a$, SO$_2$R$^a$, C$_{1-10}$alkyl, C$_{1-10}$alkenyl, C$_{2-10}$alkynyl, C$_{3-7}$cycloalkyl, C$_{5-7}$cycloalkenyl, 4–7 membered heterocycloalkyl, (cycloalkyl)alkyl, (cycloalkenyl)alkyl, (heterocycloalkyl)alkyl, aryl, heteroaryl, arylalkyl, and (heteroaryl)alkyl, wherein said alkyl, alkenyl, alkynyl, cycloalkyl, cycloalkenyl, heterocycloalkyl, aryl and heteroaryl groups are either unsubstituted or independently substituted with 1, 2 or 3 groups selected from fluoro, chloro, bromo, iodo, cyano, oxo, OR$^a$, NR$^a$R$^c$, O(C=O)R$^a$, O(C=O)NR$^a$R$^c$, NR$^a$(C=O)R$^c$, NR$^a$(C=O)OR$^c$, C(=O)R$^a$, CO$_2$R$^a$, CONR$^a$R$^c$, CSNR$^a$R$^c$, SR$^a$, S(O)R$^a$, SO$_2$R$^a$, SO$_2$NR$^a$R$^c$, YR$^d$, and ZYR$^d$;

R$^4$ and R$^5$ are each independently selected from the group consisting of hydrogen, hydroxy, amino, methyl, CF$_3$, fluoro, chloro, and bromo;

R$^6$ is selected from the group consisting of NH$_2$, and NH(C=O)OR$^e$;

R$^7$ is selected from the group consisting of hydrogen, OR$^b$, NR$^b$R$^c$, fluoro, chloro, bromo, iodo, cyano, nitro, C$_{1-6}$alkyl, C$_{2-6}$alkenyl, CF$_3$, and CHF$_2$;

R$^8$ and R$^9$ are each independently selected from the group consisting of hydrogen, fluoro, chloro, C$_{1-6}$alkyl, C$_{2-6}$alkenyl, and C$_{2-6}$alkynl, or R$^8$ and R$^9$, when taken together with the carbon atom to which they are attached, form a 3–5 membered cycloalkyl ring, or R$^8$ and R$^9$, when taken together with the carbon atom to which they are attached, form a carbonyl group;

R$^{10}$ is selected from the group consisting of hydrogen, C$_{1-10}$alkyl, C$_{2-10}$alkenyl, C$_{2-10}$alkynyl, C$_{3-6}$cycloalkyl, C$_{4-6}$cycloalkenyl, (cycloalkyl)alkyl, (cycloalkyl)alkenyl, (cycloalkenyl)alkyl, aryl, heteroaryl, arylalkyl and (heteroaryl)alkyl, wherein said alkyl, alkenyl, alkynyl, cycloalkyl, cycloalkenyl, (cycloalkyl)alkyl, (cycloalkyl)alkenyl, (cycloalkenyl)alkyl, aryl, heteroaryl, arylalkyl and (heteroaryl)alkyl groups can be optionally substituted with a group selected from bromo, iodo, OR$^b$, SR$^b$, C(=O)R$^b$, 1–3 C$_{1-3}$alkyl, 1–3 chloro, or 1–5 fluoro, or R$^{10}$ and R$^1$, when taken together with the three intervening carbon atoms to which they are attached, form a 5–6 membered cycloalkyl or cycloalkenyl ring which can be optionally substituted with 1–3 groups independently selected from oxo, hydroxy, fluoro, C$_{1-6}$alkyl, C$_{2-6}$alkenyl, C$_{2-6}$alkynyl, C$_{1-6}$alkylidenyl, C$_{3-6}$cycloalkyl, (cycloalkyl)alkyl, phenyl, or phenylalkyl, wherein said alkyl, alkenyl, alkynyl, alkylidenyl, cycloalkyl, (cycloalkyl)alkyl, phenyl, and phenylalkyl groups can be optionally substituted with a group selected from chloro, bromo, iodo, OR$^b$, SR$^b$, C$_{1-3}$alkyl, C(=O)R$^b$, or 1–5 fluoro;

R$^a$ is selected from the group consisting of hydrogen, C$_{1-10}$alkyl, and phenyl, wherein said alkyl group can be optionally substituted with a group selected from hydroxy, amino, O(C$_{1-4}$alkyl), NH$_2$, NH(C$_{1-4}$alkyl), N(C$_{1-4}$alkyl)$_2$, phenyl, or 1–5 fluoro, and wherein said phenyl groups can either be unsubstituted or substituted with 1–3 substituents independently selected from the group consisting of C$_{1-4}$alkyl, OH, O(C$_{1-4}$alkyl), NH$_2$, NH(C$_{1-4}$alkyl), N(C$_{1-4}$alkyl)$_2$, halo, CN, NO$_2$, CO$_2$H, CO$_2$(C$_{1-4}$alkyl), C(O)H, and C(O)(C$_{1-4}$alkyl);

R$^b$ is selected from the group consisting of hydrogen, C$_{1-10}$alkyl, benzyl and phenyl, wherein said phenyl group can either be unsubstituted or substituted with 1–3 substituents independently selected from the group consisting of C$_{1-4}$alkyl, OH, O(C$_{1-4}$alkyl), NH$_2$, NH(C$_{1-4}$alkyl), N(C$_{1-4}$alkyl)$_2$, halo, CN, NO$_2$, CO$_2$H, CO$_2$(C$_{1-4}$alkyl), C(O)H, and C(O)(C$_{1-4}$alkyl);

R$^c$ is selected from the group consisting of hydrogen, C$_{1-10}$alkyl and phenyl, wherein said phenyl group can either be unsubstituted or substituted with 1–3 substituents independently selected from the group consisting of C$_{1-4}$alkyl, OH, O(C$_{1-4}$alkyl), NH$_2$, NH(C$_{1-4}$alkyl), N(C$_{1-4}$alkyl)$_2$, halo, CN, NO$_2$, CO$_2$H, CO$_2$(C$_{1-4}$alkyl), C(O)H, and C(O)(C$_{1-4}$alkyl);

or R$^a$ and R$^c$, whether or not on the same atom, can be taken together with any attached and intervening atoms to form a 4–7 membered ring;

R$^d$ is selected from the group consisting of NR$^b$R$^c$, OR$^a$, CO$_2$R$^a$, O(C=O)R$^a$, CN, NR$^c$(C=O)R$^b$, CONR$^a$R$^c$, SO$_2$NR$^a$R$^c$, and a 4–9 membered mono- or bi-cyclic N-heterocycloalkyl ring that can be optonally substituted with 1–3 C$_{1-3}$alkyl and can be optionally interrupted by O, S, NR$^c$, or C=O;

R$^e$ is selected from the group consisting of hydrogen, C$_{1-6}$alkyl, C$_{2-6}$alkenyl, phenyl, and phenylalkyl, wherein said alkyl, alkenyl, or phenyl group can either be unsubstituted or substituted with 1–3 sub stituents independently selected from the group consisting of C$_{1-3}$alkyl, OH, O(C$_{1-4}$alkyl), NH$_2$, NH(C$_{1-4}$alkyl), N(C$_{1-4}$alkyl)$_2$, halo, CN, NO$_2$, CO$_2$H, CO$_2$(C$_{1-4}$alkyl), C(O)H, and C(O)(C$_{1-4}$alkyl);

Y is selected from the group consisting of CR$^b$R$^c$, C$_{2-6}$alkylene and C$_{2-6}$alkenylene, wherein said alkylene and alkenylene linkers can be optionally interrupted by O, S, or NR$^c$;

Z is selected from the group consisting of O, S, NR$^c$, C=O, O(C=O), (C=O)O, NR$^c$(C=O) or (C=O)NR$^c$;

with the proviso that when R$^6$ is NH$_2$, R$^3$ bromo and R$^{10}$ is butyl, R$^7$ is not hydrogen; and when R$^6$ is NH$_2$, R$^7$ is bromo and R$^{10}$ is ethyl, R$^3$ is not methyl;

or a pharmaceutically acceptable salt thereof.

2. The compound of claim 1 of the formula:

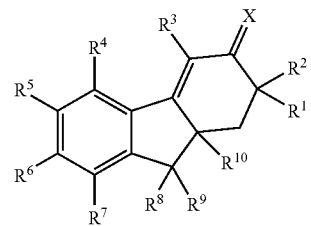

wherein X is selected from the group consisting of: O and N—OR$^a$;

R$^1$ is selected from the group consisting of hydrogen and C$_{1-6}$alkyl, wherein said alkyl group is either unsubstituted or substituted with a group selected from OR$^c$ or C(=O)R$^c$;

R$^2$ is selected from the group consisting of hydrogen, hydroxy, iodo, and C$_{1-6}$alkyl, wherein said alkyl group is either unsubstituted or substituted with a group selected from OR$^c$ or C(=O)R$^c$;

or R$^1$ and R$^2$, when taken together with the carbon atom to which they are attached, form a carbonyl group;

or R$^1$ and R$^2$, when taken together, form a C$_{1-6}$alkylidene group, wherein said alkylidene group is either unsubstituted or substituted with a group selected from the group consisting of hydroxy, O(C$_{1-4}$alkyl), N(C$_{1-4}$alkyl)$_2$, and phenyl, wherein said phenyl group can either be unsubstituted or substituted with 1–3 substituents independently selected from the group consisting of $C_{1-4}$alkyl, OH, O($C_{1-4}$alkyl), $NH_2$, NH($C_{1-4}$alkyl), N($C_{1-4}$alkyl)$_2$, halo, CN, $NO_2$, $CO_2H$, $CO_2(C_{1-4}$alkyl), C(O)H, and C(O)($C_{1-4}$alkyl);

$R^3$ is selected from the group consisting of chloro, bromo, iodo, cyano, nitro, C(=O)$R^a$, $C_{1-10}$alkyl, $C_{2-10}$alkenyl, aryl and heteroaryl, wherein said alkyl, alkenyl, aryl and heteroaryl groups are either unsubstituted or independently substituted with 1, 2 or 3 groups selected from fluoro, chloro, bromo, iodo, cyano, OR$^a$, NR$^a$R$^c$, C(=O)R$^a$, CO$_2$R$^c$, NR$^a$C(=O)R$^c$, CONR$^a$R$^c$, CSN-R$^a$R$^c$, SR$^a$, YR$_d$, and ZYR$^d$;

$R^4$ and $R^5$ are each independently selected from the group consisting of hydrogen, hydroxy and fluoro;

$R^6$ is selected from the group consisting of $NH_2$;

$R^7$ is selected from the group consisting of hydrogen, NR$^b$R$^c$, fluoro, chloro, bromo, iodo, cyano, nitro, $C_{1-6}$alkyl and $CF_3$;

$R^8$ and $R^9$ are each independently selected from the group consisting of hydrogen and $C_{1-6}$alkyl, or $R^8$ and $R^9$, when taken together with the carbon atom to which they are attached, form a carbonyl group;

$R^{10}$ is selected from the group consisting of $C_{1-10}$alkyl, $C_{2-10}$alkenyl, $C_{3-6}$cycloalkyl, (cycloalkyl)alkyl, and phenyl, wherein said alkyl, alkenyl, cycloalkyl, (cycloalkyl)alkyl, and phenyl groups can be optionally substituted with a group selected from bromo, SR$^b$, C(=O)R$^b$, 1–3 chloro, or 1–5 fluoro, or $R^{10}$ and $R^1$, when taken together with the three intervening carbon atoms to which they are attached, form a 5–6 membered cycloalkyl ring which can be optionally substituted with $C_{1-6}$alkyl, wherein said alkyl group can be optionally substituted with 1–5 fluoro;

$R^a$ is selected from the group consisting of hydrogen, $C_{1-10}$alkyl, and phenyl, wherein said alkyl group can be optionally substituted with a group selected from hydroxy, amino, O($C_{1-4}$alkyl), NH($C_{1-4}$alkyl), N($C_{1-4}$alkyl)$_2$, phenyl, or 1–5 fluoro, and wherein said phenyl groups can either be unsubstituted or substituted with 1–3 substituents independently selected from the group consisting of $C_{1-4}$alkyl, OH, O($C_{1-4}$alkyl), $NH_2$, NH($C_{1-4}$alkyl), N($C_{1-4}$alkyl)$_2$, halo, CN, $NO_2$, $CO_2H$, $CO_2(C_{1-4}$alkyl), C(O)H, and C(O)($C_{1-4}$alkyl);

$R^b$ is selected from the group consisting of hydrogen, $C_{1-10}$alkyl, benzyl and phenyl, wherein said phenyl group can either be unsubstituted or substituted with 1–3 substituents independently selected from the group consisting of $C_{1-4}$alkyl, OH, O($C_{1-4}$alkyl), $NH_2$, NH($C_{1-4}$alkyl), N($C_{1-4}$alkyl)$_2$, halo, CN, $NO_2$, $CO_2H$, $CO_2(C_{1-4}$alkyl), C(O)H, and C(O)($C_{1-4}$alkyl);

$R^c$ is selected from the group consisting of hydrogen, $C_{1-10}$alkyl and phenyl, wherein said phenyl group can either be unsubstituted or substituted with 1–3 substituents independently selected from the group consisting of $C_{1-4}$alkyl, OH, O($C_{1-4}$alkyl), $NH_2$, NH($C_{1-4}$alkyl), N($C_{1-4}$alkyl)$_2$, halo, CN, $NO_2$, $CO_2H$, $CO_2(C_{1-4}$alkyl), C(O)H, and C(O)($C_{1-4}$alkyl);

or $R^a$ and $R^c$, whether or not on the same atom, can be taken together with any attached and intervening atoms to form a 4–7 membered ring;

$R^d$ is selected from the group consisting of NR$^b$R$^c$, OR$^a$, $CO_2R^a$, O(C=O)R$^a$, CN, NR$^c$(C=O)R$^b$, CONR$^a$R$^c$, SO$_2$NR$^a$R$^c$, and a 4–7 membered N-heterocycloalkyl ring that can be optionally interrupted by O, S, NR$^c$, or C=O;

$R^e$ is selected from the group consisting of hydrogen, $C_{1-6}$alkyl, $C_{2-6}$alkenyl, phenyl, and phenylalkyl, wherein said alkyl, alkenyl, or phenyl group can either be unsubstituted or substituted with 1–3 substituents independently selected from the group consisting of$C_{1-3}$alkyl, OH, O($C_{1-4}$alkyl), $NH_2$, NH($C_{1-4}$alkyl), N($C_{1-4}$alkyl)$_2$, halo, CN, $NO_2$, $CO_2H$, $CO_2(C_{1-4}$alkyl), C(O)H, and C(O)($C_{1-4}$alkyl);

Y is selected from the group consisting of CR$^b$R$^c$, $C_{2-6}$alkylene and $C_{2-6}$alkenylene, wherein said alkylene and alkenylene linkers can be optionally interrupted by O, S, or NR$^c$;

Z is selected from the group consisting of O, S, NR$^c$, C=O, O(C=O), (C=O)O, NR$^c$(C=O) or (C=O)NR$^c$;

or a pharmaceutically acceptable salt thereof.

3. The compound according to claim 2, wherein X is selected from the group consisting of O, N—OH and N—OCH$_3$, or a pharmaceutically acceptable salt thereof.

4. The compound according to claim 3, wherein $R^3$ is selected from the group consisting of chloro, bromo, iodo, cyano, nitro, C(=O)$R^a$, $C_{1-10}$alkyl, aryl and heteroaryl wherein said alkyl, aryl and heteroaryl groups are either unsubstituted or independently substituted with 1, 2 or 3 groups selected from fluoro, NR$^a$R$^c$, OR$^a$, YR$^d$, and ZYR$^d$; or a pharmaceutically acceptable salt thereof.

5. The compound according to claim 4, wherein $R^4$ and $R^5$ are each independently selected from the group consisting of hydrogen and fluoro, or a pharmaceutically acceptable salt thereof.

6. The compound according to claim 5, wherein $R^6$ is $NH_2$, or a pharmaceutically acceptable salt thereof.

7. The compound according to claim 6, wherein $R^7$ is selected from the group consisting of hydrogen, $NH_2$, fluoro, cliloro, bromo, nitro, cyano, and $CH_3$; or a pharmaceutically acceptable salt thereof.

8. A compound according to claim 7 selected from the group consisting of:
7,8-diamino-9a-butyl-6-fluoro-4-methyl-1,2,9,9a-tetrahydro-3H-fluoren-3-one;
7-amino-9a-butyl-6-fluoro-4-nitro-1,2,9,9a-tetrahydro-3H-fluoren-3-one;
4-acetyl-7-amino-8-bromo-9a-butyl-6-fluoro-1,2,9,9a-tetrahydro-3H-fluoren-3-one;
7-amino-4,6-dibromo-9a-butyl-1,2,9,9a-tetrahydro-3H-fluoren-3-one;
7-amino-4,8-dibromo-9a-butyl-1,2,9,9a-tetrahydro-3H-fluoren-3-one;
7-amino-4-bromo-9a-butyl-8-chloro-6-fluoro-1,2,9,9a-tetrahydro-3H-fluoren-3-one;
7-amino-9a-butyl-4,8-dichloro-6-fluoro-1,2,9,9a-tetrahydro-3H-fluoren-3-one;
7-amino-9a-butyl-8-chloro-6-fluoro-4-iodo-1,2,9,9a-tetrahydro-3H-fluoren-3-one;
7-amino-9a-butyl-8-chloro-6-fluoro-4-(2-furyl)-1,2,9,9a-tetrahydro-3H-fluoren-3-one;
7-amino-4,8-dibromo-9a-butyl-6-fluoro-1,2,9,9a-tetrahydro-3H-fluoren-3-one;
7-amino-9a-butyl-6-fluoro-4-methyl-1,2,9,9a-tetrahydro-3H-fluoren-3-one;
7-amino-8-bromo-9a-butyl-6-fluoro-4-methyl-1,2,9,9a-tetrahydro-3H-fluoren-3-one;
7-amino-9a-butyl-6-fluoro-4-methyl-8-nitro-1,2,9,9a-tetrahydro-3H-fluoren-3-one;
7-amino-4-bromo-9a-butyl-6-fluoro-1,2,9,9a-tetrahydro-3H-fluoren-3-one;

7-amino-4-bromo-9a-butyl-6,8-difluoro-1,2,9,9a-tetrahydro-3H-fluoren-3-one;
7-amino-9a-butyl-6,8-difluoro-4-(trifluoromethyl)-1,2,9,9a-tetrahydro-3H-fluoren-3-one;
7-amino-9a-butyl-4-ethyl-6,8-difluoro-1,2,9,9a-tetrahydro-3H-fluoren-3-one;
7-amino-4-bromo-9a-butyl-6-fluoro-8-methyl-1,2,9,9a-tetrahydro-3H-fluoren-3-one;
7-amino-4-bromo-8-methyl-9a-propyl-1,2,9,9a-tetrahydro-3H-fluoren-3-one;
7-amino-4-bromo-9a-butyl-8-methyl-1,2,9,9a-tetrahydro-3H-fluoren-3-one;
7-amino-9a-butyl-8-methyl-4-trifluoromethyl-1,2,9,9a-tetrahydro-3H-fluoren-3-one;
7-amino-8-bromo-9a-ethyl-4-methyl-1,2,9,9a-tetrahydro-3H-fluoren-3-one;
7-amino-8-cyano-9a-ethyl-4-methyl-1,2,9,9a-tetrahydro-3H-fluoren-3-one;
7-amino-4,9a-diethyl-6-fluoro-1,2,9,9a-tetrahydro-3H-fluoren-3-one;
7-amino-4-bromo-9a-ethyl-6-fluoro-1,2,9,9a-tetrahydro-3H-fluoren-3-one;
7-amino-9a-butyl-4-ethyl-6-fluoro-1,2,9,9a-tetrahydro-3H-fluoren-3-one;
7-amino-4,9a-diethyl-6-fluoro-8-methyl-1,2,9,9a-tetrahydro-3H-fluoren-3-one;
7-amino-4-chloro-9a-ethyl-6-fluoro-8-methyl-1,2,9,9a-tetrahydro-3H-fluoren-3-one;
7-amino-4-bromo-9a-ethyl-6-fluoro-8-methyl-1,2,9,9a-tetrahydro-3H-fluoren-3-one;
7-amino-9a-butyl-6-fluoro-4,8-dimethyl-1,2,9,9a-tetrahydro-3H-fluoren-3-one;
7-amino-9a-butyl-4-ethyl-6-fluoro-8-methyl-1,2,9,9a-tetrahydro-3H-fluoren-3-one;
7-amino-9a-butyl-4-chloro-6-fluoro-8-methyl-1,2,9,9a-tetrahydro-3H-fluoren-3-one;
7-amino-9a-butyl-4-cyano-6-fluoro-8-methyl-1,2,9,9a-tetrahydro-3H-fluoren-3-one;
7-amino-9a-butyl-8-methyl-6-fluoro-4-trifluoromethyl-1,2,9,9a-tetrahydro-3H-fluoren-3-one;
7-amino-9a-ethyl-6,8-difluoro-4-methyl-1,2,9,9a-tetrahydro-3H-fluoren-3-one;
7-amino-4,9a-diethyl-6,8-difluoro-1,2,9,9a-tetrahydro-3H-fluoren-3-one;
7-amino-4-bromo-9a-ethyl-6,8-difluoro-1,2,9,9a-tetrahydro-3H-fluoren-3-one;
7-amino-9a-ethyl-6,8-difluoro-4-trifluoromethyl-1,2,9,9a-tetrahydro-3H-fluoren-3-one;
7-amino-9a-butyl-6,8-difluoro-4-methyl-1,2,9,9a-tetrahydro-3H-fluoren-3-one;
7-amino-8-chloro-9a-ethyl-6-fluoro-4-methyl-1,2,9,9a-tetrahydro-3H-fluoren-3-one;
7-amino-8-chloro-4,9a-diethyl-6-fluoro-1,2,9,9a-tetrahydro-3H-fluoren-3-one;
7-amino-4,8-dichloro-9a-ethyl-6-fluoro-1,2,9,9a-tetrahydro-3H-fluoren-3-one
7-amino-4-bromo-8-chloro-9a-ethyl-6-fluoro-1,2,9,9a-tetrahydro-3H-fluoren-3-one;
7-amino-8-chloro-9a-ethyl-6-fluoro-4-iodo-1,2,9,9a-tetrahydro-3H-fluoren-3-one;
7-amino-8-chloro-9a-ethyl-6-fluoro-4-(2-furyl)-1,2,9,9a-tetrahydro-3H-fluoren-3-one;
7-amino-8-chloro-6-fluoro-4-methyl-9a-propyl-1,2,9,9a-tetrahydro-3H-fluoren-3-one;
7-amino-8-chloro-4-ethyl-6-fluoro-9a-propyl-1,2,9,9a-tetrahydro-3H-fluoren-3-one;
7-amino-4,8-dichloro-6-fluoro-9a-propyl-1,2,9,9a-tetrahydro-3H-fluoren-3-one;
7-amino-4-bromo-8-chloro-6-fluoro-9a-propyl-1,2,9,9a-tetrahydro-3H-fluoren-3-one;
7-amino-8-chloro-6-fluoro-4-iodo-9a-propyl-1,2,9,9a-tetrahydro-3H-fluoren-3-one;
7-amino-8-chloro-6-fluoro-4-(2-furyl)-9a-propyl-1,2,9,9a-tetrahydro-3H-fluoren-3-one;
7-amino-9a-butyl-8-chloro-6-fluoro-4-methyl-1,2,9,9a-tetrahydro-3H-fluoren-3-one;
7-amino-9a-butyl-8-chloro-4-ethyl-6-fluoro-1,2,9,9a-tetrahydro-3H-fluoren-3-one;
4-acetyl-7-amino-9a-butyl-8-chloro-6-fluoro-1,2,9,9a-tetrahydro-3H-fluoren-3-one;
7-amino-8-bromo-9a-ethyl-6-fluoro-4-methyl-1,2,9,9a-tetrahydro-3H-fluoren-3-one;
7-amino-8-bromo-4,9a-diethyl-6-fluoro-1,2,9,9a-tetrahydro-3H-fluoren-3-one;
7-amino-4,8-dibromo-9a-ethyl-6-fluoro-1,2,9,9a-tetrahydro-3H-fluoren-3-one;
7-amino-8-bromo-9a-butyl-4-ethyl-6-fluoro-1,2,9,9a-tetrahydro-3H-fluoren-3-one;
7-amino-9a-ethyl-6-fluoro-4-methyl-8-nitro-1,2,9,9a-tetrahydro-3H-fluoren-3-one;
7-amino-4,9a-diethyl-6-fluoro-8-nitro-1,2,9,9a-tetrahydro-3H-fluoren-3-one;
7-amino-9a-butyl-4-ethyl-6-fluoro-8-nitro-1,2,9,9a-tetrahydro-3H-fluoren-3-one;
7,8-diamino-9a-butyl-4-ethyl-6-fluoro-1,2,9,9a-tetrahydro-3H-fluoren-3-one;
and the pharmaceutically acceptable salts thereof.

9. A pharmaceutical composition comprising a compound according to claim 1 and a pharmaceutically acceptable carrier.

10. A process for making a pharmaceutical composition comprising combining a compound according to claim 1 and a pharmaceutically acceptable carrier.

11. A method of eliciting an estrogen receptor modulating effect in a mammal in need thereof, comprising administering to the mammal a therapeutically effective amount of a compound according to claim 1.

12. The method according to claim 11 wherein the estrogen receptor modulation effect is an estrogen receptor agonizing effect.

13. The method according to claim 12 wherein the estrogen receptor agonizing effect is an ER-β receptor agonizing effect.

14. A method of treating a disease in a mammal in need thereof by administering to the mammal a therapeutically effective amount of a compound according to claim 1, wherein said disease is: bone loss, bone fractures, osteoporosis, metastaic bone disease, Paget's disease, periodontal disease, cartilage degeneration, endometriosis, uterine fibroid disease, hot flashes, increased levels of LDL cholesterol, cardiovascular disease, impairment of cognitive functioning, cerebral degenerative disorders, restenosis, gynecomastia, vascular smooth muscle cell proliferation, obesity, incontinence, anxiety, depression, an estrogen dependent cancer.

15. The method of claim 14 wherein the disease is hot flashes.

16. The method of claim 14 wherein the disease is depression.

17. A method of treating an estrogen dependent cancer in a mammal in need thereof by administering to the mammal a therapeutically effective amount of a compound according to claim 1.

18. A pharmaceutical composition comprising a compound of claim 1 and another agent selected from: an organic bisphosphonate; a cathepsin K inhibitor; an estrogen; an estrogen receptor modulator; an androgen receptor modulator; an inhibitor of osteoclast proton ATPase; an inhibitor of HMG-CoA reductase; an integrin receptor antagonist; an osteoblast anabolic agent; calcitonin; Vitamin D; a synthetic Vitamin D analogue; or a selective serotonin reuptake inhibitor; or a pharmaceutically acceptable salt or mixture thereof.

19. A method of treating hot flashes comprising administering to a mammal in need thereof a compound of claim 1 and another agent selected from: an organic bisphosphonate; a cathepsin K inhibitor; an estrogen; an estrogen receptor modulator; an androgen receptor modulator; an inhibitor of osteoclast proton ATPase; an inhibitor of HMG-CoA reductase; an integrin receptor antagonist; an osteoblast anabolic agent; calcitonin; Vitamin D; a synthetic Vitamin D analogue; or a selective serotonin reuptake inhibitor; or a pharmaceutically acceptable salt or mixture thereof.

20. A method of treating depression comprising administering to a mammal in need thereof a compound of claim 1 and another agent selected from: an organic bisphosphonate; a cathepsin K inhibitor; an estrogen; an estrogen receptor modulator; an androgen receptor modulator; an inhibitor of osteoclast proton ATPase; an inhibitor of HMG-CoA reductase; an integrin receptor antagonist; an osteoblast anabolic agent; calcitonin; Vitamin D; a synthetic Vitamin D analogue; or a selective serotonin reuptake inhibitor; or a pharmaceutically acceptable salt or mixture thereof.

21. A method of treating an estrogen dependent cancer comprising administering to a mammal in need thereof a compound of claim 1 and another agent selected from: an organic bisphosphonate; a cathepsin K inhibitor; an estrogen; an estrogen receptor modulator; an androgen receptor modulator; an inhibitor of osteoclast proton ATPase; an inhibitor of HMG-CoA reductase; an integrin receptor antagonist; an osteoblast anabolic agent; calcitonin; Vitamin D; a synthetic Vitamin D analogue; or a selective serotonin reuptake inhibitor; or a pharmaceutically acceptable salt or mixture thereof.

22. A method of lowering cholesterol comprising administering to a mammal in need thereof a compound of claim 1 and another agent selected from: an organic bisphosphonate; a cathepsin K inhibitor; an estrogen; an estrogen receptor modulator; an androgen receptor modulator; an inhibitor of osteoclast proton ATPase; an inhibitor of HMG-CoA reductase; an integrin receptor antagonist; an osteoblast anabolic agent; calcitonin; Vitamin D; a synthetic Vitamin D analogue; or a selective serotonin reuptake inhibitor; or a pharmaceutically acceptable salt or mixture thereof.

\* \* \* \* \*